United States Patent
Kano et al.

(10) Patent No.: US 11,038,885 B2
(45) Date of Patent: Jun. 15, 2021

(54) ID ACQUISITION TERMINAL APPARATUS AND METHOD AND INFORMATION PROCESSING APPARATUS AND METHOD

(71) Applicant: SONY CORPORATION, Tokyo (JP)

(72) Inventors: Shinya Kano, Tokyo (JP); Yoshinori Takagi, Tokyo (JP); Gakuho Fukushi, Kanagawa (JP); Ryu Narusawa, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 436 days.

(21) Appl. No.: 15/776,812

(22) PCT Filed: Nov. 21, 2016

(86) PCT No.: PCT/JP2016/084383
§ 371 (c)(1),
(2) Date: May 17, 2018

(87) PCT Pub. No.: WO2017/094538
PCT Pub. Date: Jun. 8, 2017

(65) Prior Publication Data
US 2018/0375864 A1    Dec. 27, 2018

(30) Foreign Application Priority Data

Dec. 3, 2015    (JP) .............................. JP2015-236451

(51) Int. Cl.
*H04L 29/06*    (2006.01)
*G06F 21/41*    (2013.01)
(Continued)

(52) U.S. Cl.
CPC .......... *H04L 63/0884* (2013.01); *G06F 21/41* (2013.01); *G06Q 50/22* (2013.01);
(Continued)

(58) Field of Classification Search
CPC ............. H04L 63/0884; H04L 63/0853; H04L 63/083; G16H 10/60; G06F 21/41; G06Q 50/22
See application file for complete search history.

(56) References Cited

U.S. PATENT DOCUMENTS 7,870,614 B1 *    1/2011    Duhaime ............. G06Q 20/383
                                                726/28
9,641,503 B2 *    5/2017    Mehta ................. H04L 63/0815
(Continued)

FOREIGN PATENT DOCUMENTS

JP    2002-230156 A    8/2002
JP    2002-351997 A    12/2002
(Continued)

OTHER PUBLICATIONS

Guillen et al., Accessing to electronic medical history using a mobility intra hospital system, Dec. 2011, Annual International Conference of the IEEE Engineering in Medicine and Biology Society, pp. 3546-3549 (Year: 2011).*

(Continued)

*Primary Examiner* — Kenneth W Chang
(74) *Attorney, Agent, or Firm* — Chip Law Group

(57) ABSTRACT

The present technology relates to an ID acquisition terminal apparatus and method, an information processing apparatus and method, and a program by which the convenience can be improved.
A service A auxiliary system includes a communication unit that acquires a nonstandard ID different from a standard ID, which is used upon provision of a predetermined service, and authentication information, an authentication processing unit that performs an authentication process of the nonstandard ID with authentication information, and a table management unit that reads out the standard ID recorded in an associated relationship with the nonstandard ID. Upon uti-
(Continued)

lization of a service in which an other-service IC card is used, the nonstandard ID and the authentication information read out from the other-service IC card are acquired by the communication unit of the service A auxiliary system, and an authentication process and reading out of the standard ID are performed. The present technology can be applied to a service provision system.

19 Claims, 36 Drawing Sheets

(51) Int. Cl.
    *G06Q 50/22* (2018.01)
    *G16H 40/67* (2018.01)
    *G16H 10/60* (2018.01)

(52) U.S. Cl.
    CPC ............. *G16H 10/60* (2018.01); *G16H 40/67* (2018.01); *H04L 63/0853* (2013.01); *H04L 63/083* (2013.01)

(56) References Cited

U.S. PATENT DOCUMENTS

| | | | | |
|---|---|---|---|---|
| 2002/0083014 A1* | 6/2002 | Brickell | ............... | G06Q 20/206 705/76 |
| 2008/0189793 A1* | 8/2008 | Kirkup | ................. | G06F 21/604 726/27 |
| 2009/0144200 A1 | 6/2009 | Yoshioka | | |
| 2009/0295569 A1* | 12/2009 | Corwin | ................. | G16H 10/65 340/539.12 |
| 2013/0111353 A1* | 5/2013 | Ueda | ..................... | G16H 30/20 715/748 |
| 2014/0089001 A1* | 3/2014 | Macoviak | ............ | G06Q 30/018 705/2 |
| 2015/0051919 A1 | 2/2015 | Fukushi et al. | | |
| 2016/0034642 A1* | 2/2016 | Ehrhart | ................. | G16H 10/60 705/3 |

FOREIGN PATENT DOCUMENTS

| | | |
|---|---|---|
| JP | 2003-132022 A | 5/2003 |
| JP | 2008-310574 A | 12/2008 |
| JP | 2009-140057 A | 6/2009 |
| JP | 2011-233110 A | 11/2011 |
| JP | 2012-068838 A | 4/2012 |
| JP | 2014-106839 A | 6/2014 |
| WO | 2013/161458 A1 | 10/2013 |

OTHER PUBLICATIONS

International Search Report and Written Opinion of PCT Application No. PCT/JP2016/084383, dated Feb. 21, 2017, 17 pages of ISRWO.

* cited by examiner

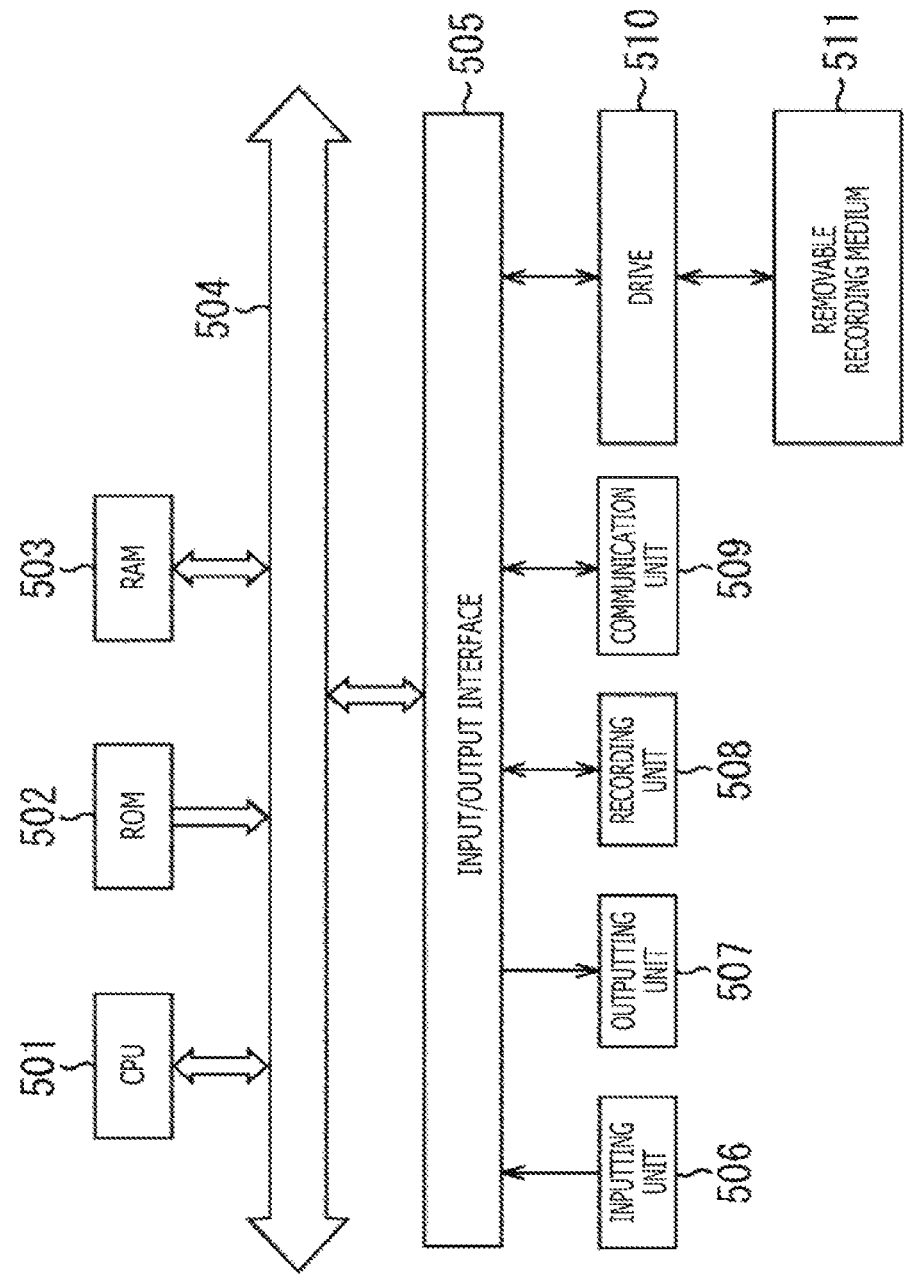

ID ACQUISITION TERMINAL APPARATUS AND METHOD AND INFORMATION PROCESSING APPARATUS AND METHOD

CROSS REFERENCE TO RELATED APPLICATIONS

This application is a U.S. National Phase of International Patent Application No. PCT/JP2016/084383 filed on Nov. 21, 2016, which claims priority benefit of Japanese Patent Application No. JP 2015-236451 filed in the Japan Patent Office on Dec. 3, 2015. Each of the above-referenced applications is hereby incorporated herein by reference in its entirety.

TECHNICAL FIELD

The present technology relates to an ID acquisition terminal apparatus and method, an information processing apparatus and method, and a program, and particularly to an ID acquisition terminal apparatus and method, an information processing apparatus and method, and a program by which the convenience can be improved.

BACKGROUND ART

In the past, in the case in which a user intends to utilize a predetermined service, upon new registration into the service, either the service issues ID information or the user selects free ID information has been determined ID information to be utilized in the service. For example, in the case in which the user selects free ID information, if ID information selected by the user does not overlap in the service, then the ID information is registered as useable ID information.

After the ID information is registered in this manner, the user will utilize the service using the registered ID information.

In particular, for example, in an electronic medication notebook service, upon new registration into the service, ID information that does not overlap in the service is issued, and the ID information is written into a card for exclusive use that is standardly utilized by the service. Then, the user can utilize the service by using the card.

However, in the meantime, there are many cases in which a user has some other ID cards such as a driver's license, a My Number card and so forth, and it is the current situation that also there are many persons who feel it cumbersome to own and manage several ID cards.

Therefore, as a system that manages ID information to be utilized in a service, a technology has been proposed in which a common authentication server retains common authentication IDs and common authentication information of users and manages user IDs and passwords of each of a plurality of services in an associated relationship with the common authentication IDs (for example, refer to PTL 1).

In this technology, in the case in which the user tries to utilize a demanded service, after the common authentication server authenticates the user on the basis of the common authentication ID and the common authentication information, it reads out the user ID and the password for the designated service and requests authentication to a utilization service authentication server for the service. Then, if the user is authenticated by the utilization service authentication server, then the user is enabled to utilize the service.

CITATION LIST

Patent Literature

[PTL 1]
JP 2003-132022A

SUMMARY

Technical Problem

In the technology described above, although, if authentication of the user is performed, then a terminal operated by the user and a service system are placed into a coupled state, some other information than the user ID is sometimes necessitated when the user utilizes the service. However, such a case as just described is not supposed in the technology described above. Therefore, it becomes necessary for the user to further use a card for exclusive use or the like after the authentication or input necessary information, and this is inconvenient.

The present technology has been made in view of such a situation as described above and makes it possible to improve the convenience.

Solution to Problem

An ID acquisition terminal apparatus of a first aspect of the present technology is an ID acquisition terminal apparatus connected to a medication history information management apparatus and an intermediate information management apparatus through a communication network, the ID acquisition terminal apparatus including a communication unit that transmits and receives information, an acquisition unit that acquires ID information and service utilization additional information, and a control unit that controls the communication unit and the acquisition unit. In the case where a standard ID as the ID information and first service utilization additional information are acquired by the acquisition unit, the control unit executes a process for transmitting the standard ID and the first service utilization additional information from the communication unit to the medication history information management apparatus. In the case where a nonstandard ID as the ID information and second service utilization additional information are acquired by the acquisition unit, the control unit executes a process for transmitting the nonstandard ID from the communication unit to the intermediate information management apparatus, a process for receiving the standard ID associated with the nonstandard ID and third service utilization additional information from the intermediate information management apparatus by the communication unit, and a process for transmitting the standard ID, the second service utilization additional information, and the third service utilization additional information from the communication unit.

In the case where the nonstandard ID and the third service utilization additional information are acquired by the acquisition unit, the control unit may perform a process for transmitting the nonstandard ID and the third service utilization additional information to the intermediate information management apparatus.

The acquisition unit may acquire the standard ID or the nonstandard ID and the service utilization additional information from an IC card.

An ID acquisition method or a program of the first aspect of the present technology is an ID acquisition method or a program by an ID acquisition terminal apparatus that is connected to a medication history information management apparatus and an intermediate information management apparatus through a communication network and includes a communication unit that transmits and receives information, an acquisition unit that acquires ID information and service utilization additional information, and a control unit that controls the communication unit and the acquisition unit. In the case where a standard ID as the ID information and first service utilization additional information are acquired by the acquisition unit, the control unit executes a process for transmitting the standard ID and the first service utilization additional information from the communication unit to the medication history information management apparatus. In the case where a nonstandard ID as the ID information and second service utilization additional information are acquired by the acquisition unit, the control unit executes a process for transmitting the nonstandard ID from the communication unit to the intermediate information management apparatus, a process for receiving the standard ID associated with the nonstandard ID and third service utilization additional information from the intermediate information management apparatus by the communication unit, and a process for transmitting the standard ID, the second service utilization additional information, and the third service utilization additional information from the communication unit.

In the first aspect of the present technology, in the ID acquisition terminal apparatus that is connected to a medication history information management apparatus and an intermediate information management apparatus through a communication network and includes a communication unit that transmits and receives information, an acquisition unit that acquires ID information and service utilization additional information, and a control unit that controls the communication unit and the acquisition unit. In the case where a standard ID as the ID information and first service utilization additional information are acquired by the acquisition unit, the control unit executes a process for transmitting the standard ID and the first service utilization additional information from the communication unit to the medication history information management apparatus. In the case where a nonstandard ID as the ID information and second service utilization additional information are acquired by the acquisition unit, the control unit executes a process for transmitting the nonstandard ID from the communication unit to the intermediate information management apparatus, a process for receiving the standard ID associated with the nonstandard ID and third service utilization additional information from the intermediate information management apparatus by the communication unit, and a process for transmitting the standard ID, the second service utilization additional information, and the third service utilization additional information from the communication unit.

An information processing apparatus of a second aspect of the present technology includes an acquisition unit that acquires nonstandard ID information different from ID information, which is used upon provision of a given service, and authentication information, an authentication processing unit that performs an authentication process of the nonstandard ID information with the authentication information, a recording unit that records the nonstandard ID information, the ID information, and service utilization additional information that is used upon provision of the service in an associated relationship with each other, and a management unit that acquires the ID information and the service utilization additional information associated with the nonstandard ID information from the recording unit.

The acquisition unit may acquire information for obtaining the service utilization additional information that is newer, and the management unit may update the service utilization additional information recorded in the recording unit based on the information for obtaining the service utilization additional information that is newer.

The acquisition unit may acquire the ID information and the service utilization additional information, and the management unit may specify a newer one from between the service utilization additional information acquired by the acquisition unit and the service utilization additional information recorded in the recording unit and either update the service utilization additional information recorded in the recording unit or control update of the ID information by the acquisition unit and the service utilization additional information of an acquisition source of the service utilization additional information.

The recording unit may record the nonstandard ID information, the ID information, and service utilization additional information difference information for obtaining part of the service utilization additional information in an associated relationship with each other and the acquisition unit may acquire the nonstandard ID information, the authentication information, and service utilization additional information corresponding information for obtaining part of the service utilization additional information upon provision of the service. The information processing apparatus may further include a control unit that generates the service utilization additional information based on the service utilization additional information difference information and the service utilization additional information corresponding information.

In the case where part of the nonstandard ID information recorded in an acquisition source of the nonstandard ID information by the acquisition unit changes by reissuance, the management unit may compare the nonstandard ID information acquired by the acquisition unit and the nonstandard ID information recorded in the recording unit with each other and update the nonstandard ID information recorded in the recording unit in response to a result of the comparison.

An information processing method and a program of the second aspect of the present technology includes the steps of acquiring nonstandard ID information different from ID information, which is used upon provision of a given service, and authentication information, performing an authentication process of the nonstandard ID information with the authentication information, and acquiring, from a recording unit that records the nonstandard ID information, the ID information, and service utilization additional information that is used upon provision of the service in an associated relationship with each other, the ID information and the service utilization additional information associated with the nonstandard ID information.

In the second aspect of the present technology, nonstandard ID information different from ID information, which is used upon provision of a given service, and authentication information are acquired, and an authentication process of the nonstandard ID information is performed with the authentication information. Then, from a recording unit in which the nonstandard ID information, the ID information, and service utilization additional information that is used upon provision of the service are recorded in an associated relationship with each other, the ID information and the service utilization additional information associated with the nonstandard ID information are acquired.

An information processing apparatus of a third aspect of the present technology includes an acquisition unit that acquires nonstandard ID information different from ID information that is used upon provision of a given service from an other-service provision apparatus that provides a different service different from the given service, a management unit that reads out the ID information recorded in an associated relationship with the nonstandard ID information, and a process execution unit that executes, in the case where execution of a process for providing the given service permitted to the different service is requested from the other-service provision apparatus, a process according to the request using the ID information.

The acquisition unit may acquire authentication information together with the nonstandard ID information from the other-service provision apparatus, and the information processing apparatus may further include an authentication processing unit that performs an authentication process of the nonstandard ID information with the authentication information.

The information processing apparatus may further include a recording unit that records other-service access permission information set by a user and indicative of whether or not access of the different service to the given service is to be permitted, and a control unit that permits the access of the other-service provision apparatus based on the other-service access permission information.

An information processing method of the third aspect of the present technology includes the steps of acquiring nonstandard ID information different from ID information that is used upon provision of a given service from an other-service provision apparatus that provides a different service different from the given service, reading out the ID information recorded in an associated relationship with the nonstandard ID information, and executing, in the case where execution of a process for providing the given service permitted to the different service is requested from the other-service provision apparatus, a process according to the request using the ID information.

In the third aspect of the present technology, nonstandard ID information different from ID information that is used upon provision of a given service is acquired from an other-service provision apparatus that provides a different service different from the given service, and the ID information recorded in an associated relationship with the nonstandard ID information is read out. Further, in the case where execution of a process for providing the given service permitted to the different service is requested from the other-service provision apparatus, a process according to the request is executed using the ID information.

An information processing apparatus of a fourth aspect of the present technology includes an acquisition unit that acquires nonstandard ID information different from ID information to be used upon provision of a given service from an other-service provision apparatus that provides a different service different from the given service, an other-service management unit that manages access information for allowing the different service to access the given service, and a service management unit that reads out, in the case where the nonstandard ID information acquired by the acquisition unit is supplied to the service management unit together with a request for access to the given service based on the access information from the service management unit, the ID information recorded in an associated relationship with the nonstandard ID information and executes, using the ID information, a process according to a request for execution of a process for providing the given service permitted to the different service.

The acquisition unit may acquire authentication information together with the nonstandard ID information from the other-service provision apparatus, and the information processing apparatus may further include an authentication processing unit that performs an authentication process of the nonstandard ID information based on library information common to the individual services and the authentication information.

The service management unit may manage other-service access permission information set by a user and indicative of whether or not access of the different service to the given service is permitted and permit access to the other-service provision apparatus based on the other-service access permission information.

An information processing method of the fourth aspect of the present technology is an information processing method for an information processing apparatus that includes an acquisition unit that acquires nonstandard ID information different from ID information to be used upon provision of a given service from an other-service provision apparatus that provides a different service different from the given service, an other-service management unit that manages access information for allowing the different service to access the given service, and a service management unit that reads out, in the case where the nonstandard ID information acquired by the acquisition unit is supplied to the service management unit together with a request for access to the given service based on the access information from the service management unit, the ID information recorded in an associated relationship with the nonstandard ID information and executes, using the ID information, a process according to a request for execution of a process for providing the given service permitted to the different service. The information processing method includes the steps of by the acquisition unit, acquiring the nonstandard ID information from the other-service provision apparatus, by the other-service management unit, requesting access to the given service based on the access information to the service management unit and supplying the nonstandard ID information acquired by the acquisition unit to the service management unit, and by the service management unit, reading out the ID information recorded in an associated relationship with the nonstandard ID information and executing, using the ID information, a process according to a request from the other-service provision apparatus for executing a process for providing the given service permitted to the different service.

In the fourth aspect of the present technology, the nonstandard ID information different from the ID information to be used upon provision of a given service is acquired from an other-service provision apparatus that provides a different service different from the given service, and access information for allowing the different service to access the given service is managed. Further, in the case where the acquired nonstandard ID information is supplied together with a request for access to the given service based on the access information, the ID information recorded in an associated relationship with the nonstandard ID information is read out, and using the ID information, a process according to a request from the other-service provision apparatus for executing a process for providing the given service permitted to the different service is executed.

Advantageous Effect of Invention

With the first to fourth aspects of the present technology, the convenience can be improved.

It is to be noted that the effect described here is not necessarily restrictive and the effect may be any one of the effects described in the present disclosure.

BRIEF DESCRIPTION OF DRAWINGS

FIG. 38 is a view depicting an example of a configuration of a computer.

DESCRIPTION OF EMBODIMENTS

In the following, embodiments to which the present technology is applied are described with reference to the drawings.

First Embodiment

<Overview of Present Technology>

The present technology improves the convenience upon service utilization by making it possible, in the case in which provision of a predetermined service is to be received, to receive provision of the service even if not only ID information for exclusive use for the service but also ID information for utilization of some other-service are used.

Figure 1:
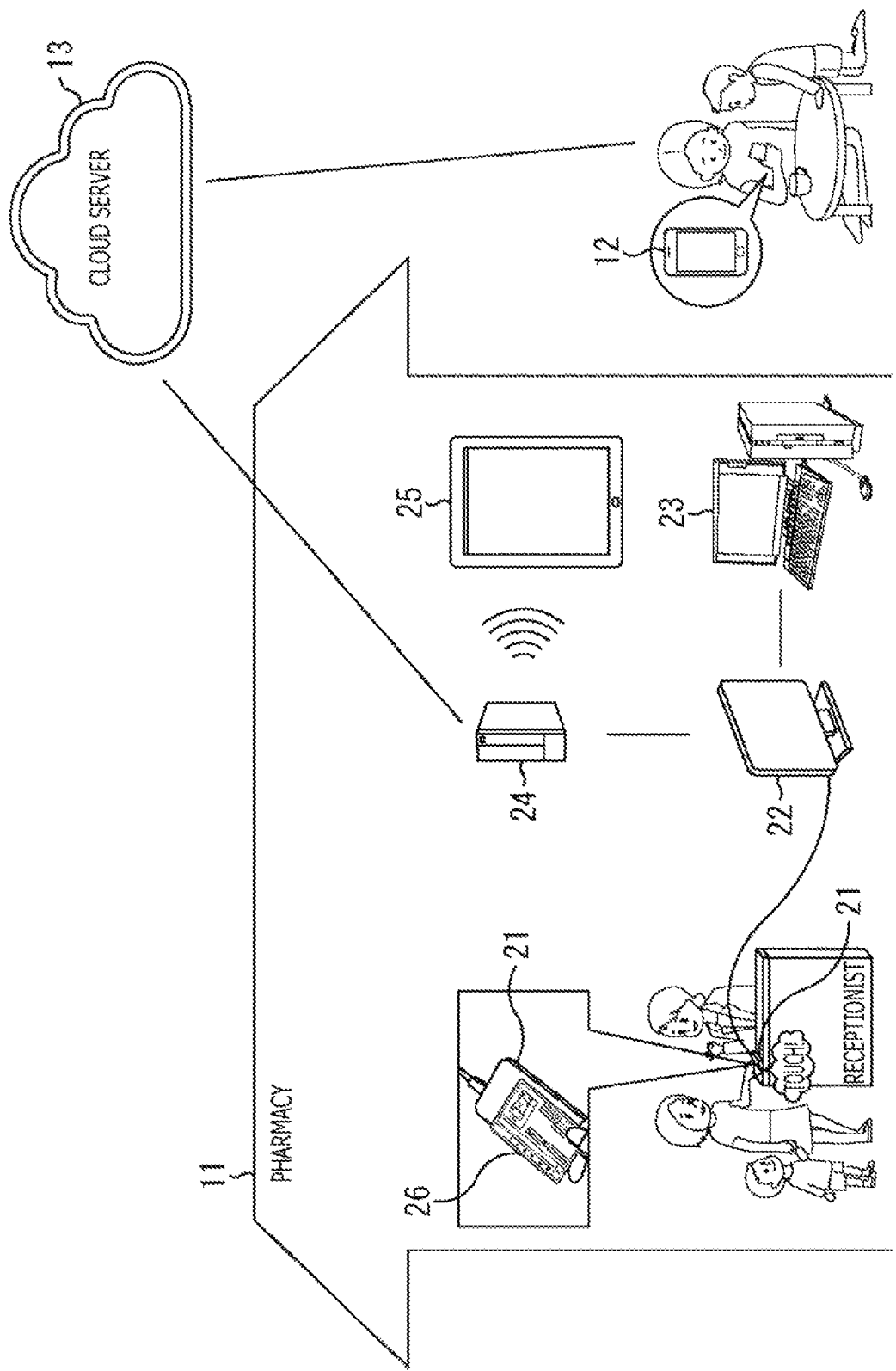
FIG. 1 is a view illustrating an overview of the present technology.

In particular, the present technology can be applied, for example, to a system depicted in FIG. 1 and so forth.

In FIG. 1, the user would utilize a system installed in a pharmacy 11 or utilizes an own portable telephone set 12 or the like when the user is at home to receive provision of a service from a cloud server 13. At this time, the service provided to the user is, for example, a browsing service of medication history information that is a history of medicines disposed for the user.

In the pharmacy 11, for example, a card reader 21, a computer 22, a receipt computer 23, a router 24, and a tablet type terminal apparatus 25 are provided.

For example, medication history information of the user is inputted to the receipt computer 23 and is transmitted from the receipt computer 23 to the cloud server 13 through the computer 22 and the router 24, and the medication history information is managed by the cloud server 13. For example, in the cloud server 13, ID information for exclusive use for a service for uniquely specifying the user, and the medication history information are managed in an associated relationship with each other.

Further, upon browsing of the medication history information, for example, if the user holds an IC card for exclusive use for the service over the card reader 21, then the card reader 21 reads out the ID information for exclusive use for the service from the IC card and supplies it to the computer 22. The computer 22 supplies the ID information supplied from the card reader 21 to the tablet type terminal apparatus 25 through the router 24.

Then, the tablet type terminal apparatus 25 transmits the ID information to the cloud server 13 through the router 24 and requests transmission of medication history information.

In response to this, the medication history information is transmitted from the cloud server 13, and the tablet type terminal apparatus 25 receives the medication history information from the cloud server 13 through the router 24 and displays it. When the medication history information is displayed in this manner, the user, a pharmacist or the like who is in the pharmacy 11 can browse the medication history information.

Incidentally, while generally there are many services provided by servers or the like, if an IC card for exclusive use for each service is necessitated, then management and so forth of IC cards are complicated. Therefore, the present technology makes it possible to browse medication history information even if an IC card 26 for utilization of some other-service is used.

Here, the IC card 26 for utilization of some other-service is, for example, a driver's license, a My Number card, a passport, a health insurance card or the like.

In this case, if the user holds the IC card 26, which is a driver's license or a My Number card, over the card reader 21, then the medication history information can be read through the tablet type terminal apparatus 25 similarly as in the case in which an IC card for exclusive use is held over. In short, provision of a service can be received from the cloud server 13.

<Example of Configuration of Service Provision System>

Now, a more particular example of a configuration of the service provision system by which provision of a service can be received even if such an IC card for exclusive use for some other-service is utilized is described.

Figure 2:
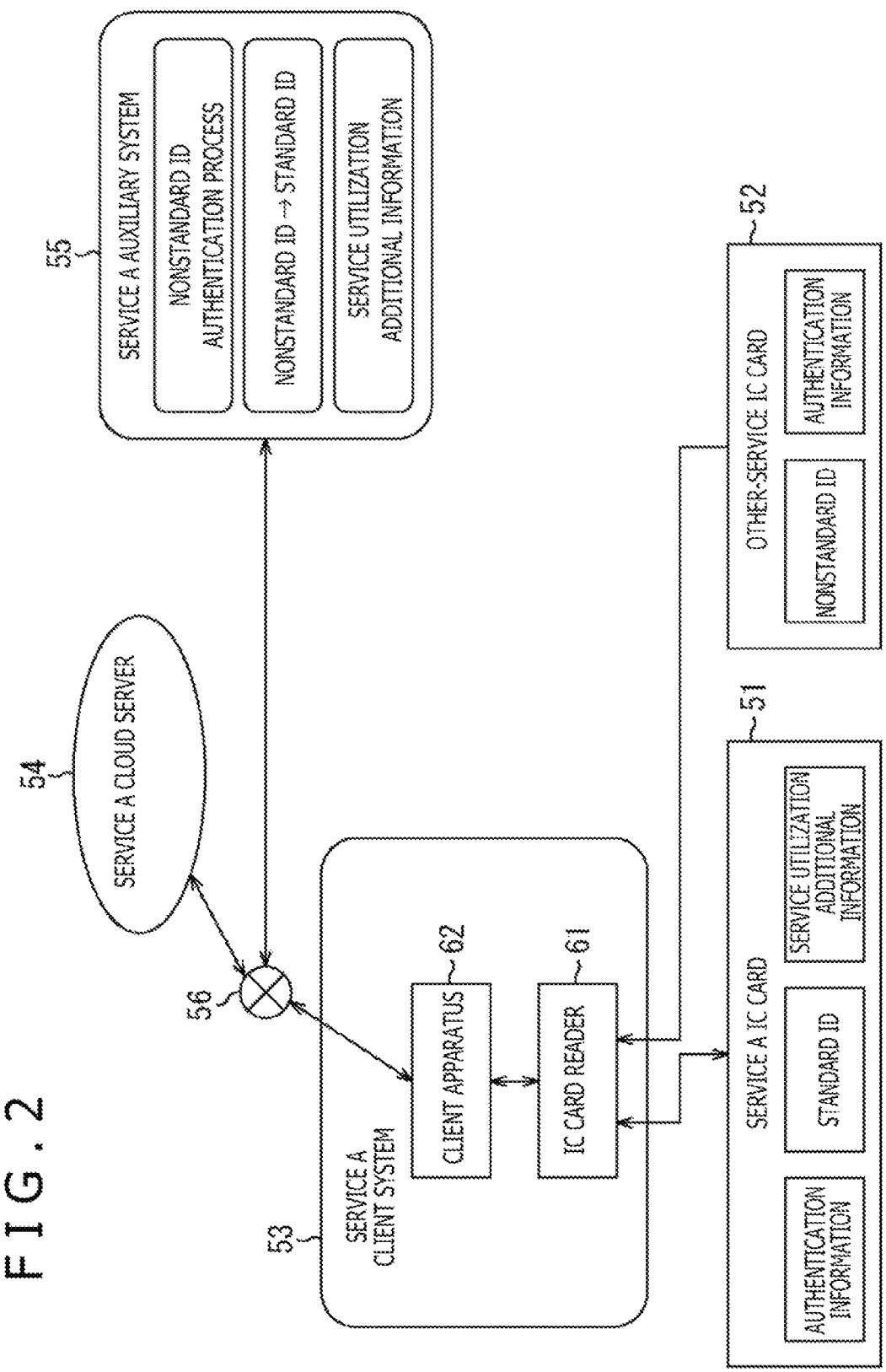
FIG. 2 is a view depicting an example of a configuration of a service provision system.

FIG. 2 is a view depicting an example of a configuration of the service provision system to which the present technology is applied.

The service provision system depicted in FIG. 2 is a system for allowing a user or the like to utilize a predetermined service A.

This service provision system includes a service A IC card 51, an other-service IC card 52, a service A client system 53, a service A cloud server 54, and a service A auxiliary system 55.

In the service provision system, the service A client system 53 to service A auxiliary system 55 are connected to each other through a communication network 56 such as the Internet. It is to be noted that the communication network 56 is a communication network configured from a wired communication network, a wireless communication network, or both of the networks.

In this example, the other-service IC card 52, the service A client system 53, and the service A cloud server 54 correspond to the IC card 26, the pharmacy 11, and the cloud server 13 depicted in FIG. 1, respectively.

Further, while it is described also here that the service A provided by the service A cloud server 54 is browsing of medication history information or the like, the substance of the service A to be provided by the service A cloud server 54 may be any substance.

In the following description, the service A is referred to simply as service, and when the term service is used simply, this signifies a service provided by the service A cloud server 54.

The service A IC card 51 is an IC card for exclusive use for allowing its user to receive provision of the service from the service A cloud server 54. The service A IC card 51 is issued to each user, and the user will receive provision of the service basically using the service A IC card 51 possessed thereby.

For example, in the service A IC card 51, a standard ID that is ID information with which the user can be identified uniquely by the service A cloud server 54, service utilization additional information that is necessitated for the user to receive provision of the service and authentication information that is used for authentication of the user are recorded.

For example, while the service utilization additional information may be any information, it is assumed here that the service utilization additional information is information relating to the user such as the name, the birth date, an address, an insurance card number, sexuality, and a hash value of the insurance card number of the user.

The other-service IC card 52 is an IC card that is used when the user tries to receive provision of a different service different from the service provided by the service A cloud server 54, and is a driver's license, a My Number card, a passport, a health insurance card or the like.

For example, in the other-service IC card 52, at least a nonstandard ID that is ID information with which the user can be identified uniquely in a different service and authentication information for performing authentication of the user are recorded. Further, in the other-service IC card 52, also information necessary for the utilization of a different service, for example, information relating to the user such as the name, the birth date, and an address of the user, and so forth are recorded as occasion demands.

The service A client system 53 includes an IC card reader 61 and a client apparatus 62, and is utilized when the service is provided to the user. Especially, the IC card reader 61 corresponds to the card reader 21 depicted in FIG. 1 and the client apparatus 62 corresponds to part or all of the computer 22 to tablet type terminal apparatus 25 depicted in FIG. 1.

The service A cloud server 54 retains medication history information of the user in an associated with the standard ID, and suitably provides the medication history information to provide the service to the user.

The service A auxiliary system 55 is a system that performs an auxiliary process for service provision such as authentication or the like when the user tries to utilize the other-service IC card 52 to receive provision of the service.

In such a service provision system as described above, for example, after the standard ID and the authentication information are read out from the service A IC card 51 by the IC card reader 61, the client apparatus 62 generates new medication history information in response to an inputting operation by a pharmacist or the like.

Then, the client apparatus 62 transmits the standard ID read out by the IC card reader 61 and the generated new medication history information to the service A cloud server 54 through the communication network 56 so as to be recorded. The service A cloud server 54 records the received standard ID and new medication history information in an associated relationship with each other in response to an instruction of the client apparatus 62. At this time, authentication of the user specified by the standard ID, namely, of the service A IC card 51, is performed depending upon the authentication information as occasion demands.

Further, upon browsing of medication history information, for example, if the user holds the service A IC card 51 over the IC card reader 61, then the IC card reader 61 reads out the standard ID, the authentication information, and the service utilization additional information from the service A IC card 51 and supplies them to the client apparatus 62.

Consequently, the client apparatus 62 transmits a transmission request of medication history information to the service A cloud server 54 through the communication network 56 together with the standard ID and the authentication information supplied from the IC card reader 61. At this time, the client apparatus 62 transmits also the service utilization additional information to the service A cloud server 54 as occasion demands.

When the service A cloud server 54 receives the transmission request from the client apparatus 62, it performs authentication suitably and transmits the medication history information associated with the standard ID received together with the transmission request to the client apparatus 62 through the communication network 56.

Then, the client apparatus 62 displays the medication history information received from the service A cloud server 54 and part of the read out service utilization additional information, for example, the name of the user or the like, such that the medication history information can be browsed. Consequently, the user or the like can receive provision of the service.

It is to be noted that, upon provision of the service, the service utilization additional information is sometimes used in the service A cloud server 54. For example, in the client apparatus 62, in the case in which information relating to the user is managed by a patient ID with which the user can be identified uniquely in the service A client system 53, the service utilization additional information is used when the user receives provision of the service for the first time.

In particular, a hash number or the like of an insurance card number as the service utilization additional information is utilized as service utilization additional information in order to confirm, for example, the association between the patient ID and the standard ID, namely, that the ID information of them is ID information of the same user.

Further, also the service utilization additional information may be transmitted from the client apparatus 62 to the service A cloud server 54 such that the service A cloud server 54 generates display data for displaying information relating to the user such as medication history information, the name or the like from the service utilization additional information and the medication history information.

In the service A cloud server 54, the process for providing a service is executed using the standard ID and the service utilization additional information as keys in such a manner as described above.

On the other hand, in the case where the user receives provision of the service using the other-service IC card 52 that is not for exclusive use for the service A, registration of the other-service IC card 52 in advance is necessitated.

Upon registration, for example, if the user holds the other-service IC card 52 over the IC card reader 61, then the IC card reader 61 reads out and supplies a nonstandard ID and authentication information from the other-service IC card 52 to the client apparatus 62.

Consequently, the client apparatus 62 transmits the nonstandard ID and the authentication information supplied from the IC card reader 61 to the service A auxiliary system 55 through the communication network 56. At this time, the nonstandard ID and the authentication information may otherwise be transmitted from the client apparatus 62 to the service A auxiliary system 55 through the service A cloud server 54.

After the service A auxiliary system 55 receives the nonstandard ID and the authentication information, it authenticates the user identified by the nonstandard ID, namely, the other-service IC card 52, on the basis of the authentication information.

If it is confirmed as a result of the authentication that the other-service IC card 52 is a legitimate one, then the service A auxiliary system 55 receives issuance of a standard ID from the service A cloud server 54 and generates and records an ID correspondence table in which the standard ID and the nonstandard ID are associated with each other. Further, the service A auxiliary system 55 acquires and records the service utilization additional information from the client apparatus 62, and registration of the other-service IC card 52 is completed.

After registration is completed, the service A auxiliary system 55 can obtain the standard ID from the nonstandard ID read out from the other-service IC card 52 using the ID correspondence table. Further, since also the service utilization additional information is recorded, the standard ID and the service utilization additional information can be supplied to the service A cloud server 54. Consequently, a service can be provided to the user who possesses the registered other-service IC card 52.

In this manner, the service A auxiliary system 55 has a function for performing an authentication process of a nonstandard ID and an ID reading out process for reading out a standard ID from the nonstandard ID, and records the service utilization additional information.

It is to be noted that the service A auxiliary system 55 may be an apparatus different from the service A cloud server 54 as depicted in FIG. 2 or may be a same apparatus as the service A cloud server 54. Further, the service A auxiliary system 55 may be connected to the service A cloud server 54 through the communication network 56 or may be connected directly to the service A cloud server 54.

Furthermore, while an example is described here in which a standard ID or a nonstandard ID that is ID information necessary to receive provision of a service is read out from the service A IC card 51 or the other-service IC card 52, the acquisition source of the ID information may not be an IC card. For example, a standard ID or a nonstandard ID may be inputted by a user or the like or may be acquired from some other arbitrary medium or apparatus such as a portable telephone set.

Further, an apparatus such as a portable telephone set corresponding to the service A IC card 51 or the other-service IC card 52 may communicate with the service A cloud server 54 or the service A auxiliary system 55 through the communication network 56 without the intervention of the service A client system 53.

<Example of Configuration of Client Apparatus>

Now, an example of a more detailed configuration of the client apparatus 62, the service A cloud server 54, and the service A auxiliary system 55 is described.

First, the client apparatus 62 is described.

Figure 3:
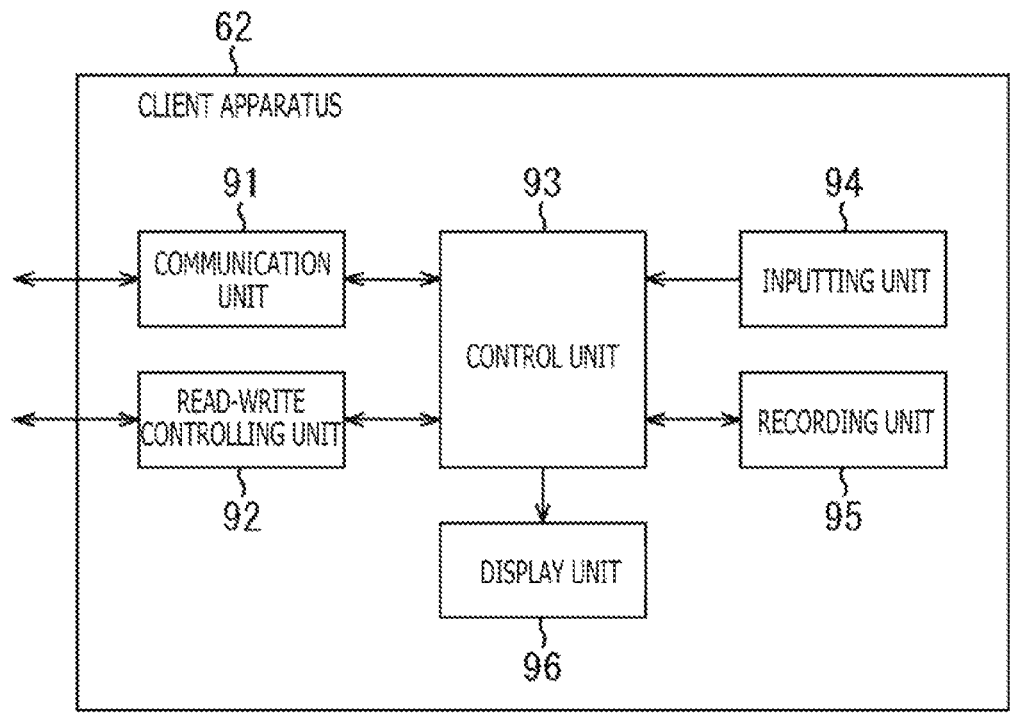
FIG. 3 is a view depicting an example of a configuration of a client apparatus.

FIG. 3 is a view depicting an example of a more detailed configuration of the client apparatus 62. It is to be noted that, while the client apparatus 62 here is formed as one apparatus, the client apparatus 62 may otherwise be configured from a plurality of apparatus.

The client apparatus 62 depicted in FIG. 3 includes a communication unit 91, a read-write controlling unit 92, a control unit 93, an inputting unit 94, a recording unit 95, and a display unit 96.

The communication unit 91 transmits various kinds of information supplied from the control unit 93 to various apparatus of the service provision system through the communication network 56, or receives and supplies information transmitted thereto from the apparatus to the control unit 93.

The read-write controlling unit 92 controls the IC card reader 61 to read out necessary information from the service A IC card 51 or the other-service IC card 52 and write information in the service A IC card 51.

The control unit 93 controls the components of the client apparatus 62. The inputting unit 94 is configured, for example, from a touch panel superposed on the display unit 96, a mouse, a button or the like, and supplies a signal corresponding to an operation thereof by the user to the control unit 93.

The recording unit 95 records various kinds of information supplied from the control unit 93 and supplies the recorded information to the control unit 93. The display unit 96 is configured, for example, from a liquid crystal display unit, and displays an image or the like under the control of the control unit 93.

<Example of Configuration of Service a Cloud Server>

Figure 4:
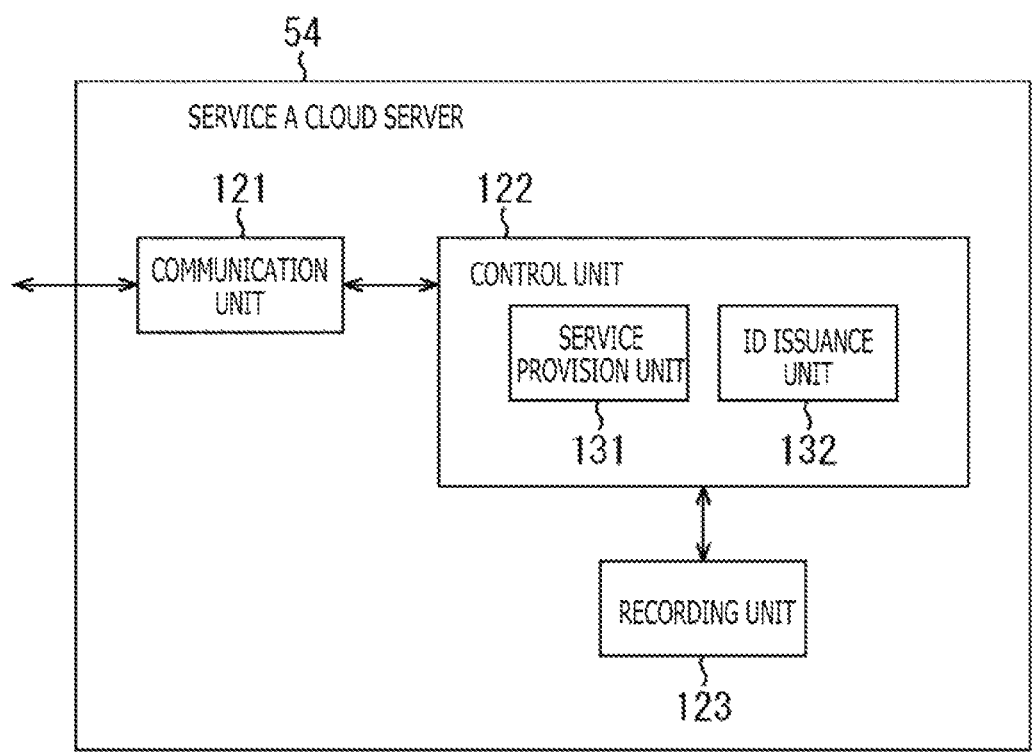
FIG. 4 is a view depicting an example of a configuration of a service A cloud server.

FIG. 4 is a view depicting an example of a more detailed configuration of the service A cloud server 54. It is to be noted, while the service A cloud server 54 here is configured from a single information processing apparatus, the service A cloud server 54 may otherwise be configured from a plurality of apparatus.

The service A cloud server 54 includes a communication unit 121, a control unit 122, and a recording unit 123.

The communication unit 121 transmits various kinds of information supplied from the control unit 122 to the individual apparatus of the service provision system through the communication network 56, and receives information transmitted from the apparatus and supplies the received information to the control unit 122.

The control unit 122 controls the components of the service A cloud server 54. The control unit 122 includes a service provision unit 131 and an ID issuance unit 132.

The service provision unit 131 executes various processes for providing a service by the service A cloud server 54. The ID issuance unit 132 generates a standard ID to perform issuance of the standard ID.

The recording unit 123 records various kinds of information supplied from the control unit 122 and supplies the recorded information to the control unit 122.

<Example of Configuration of Service a Auxiliary System>

Figure 5:
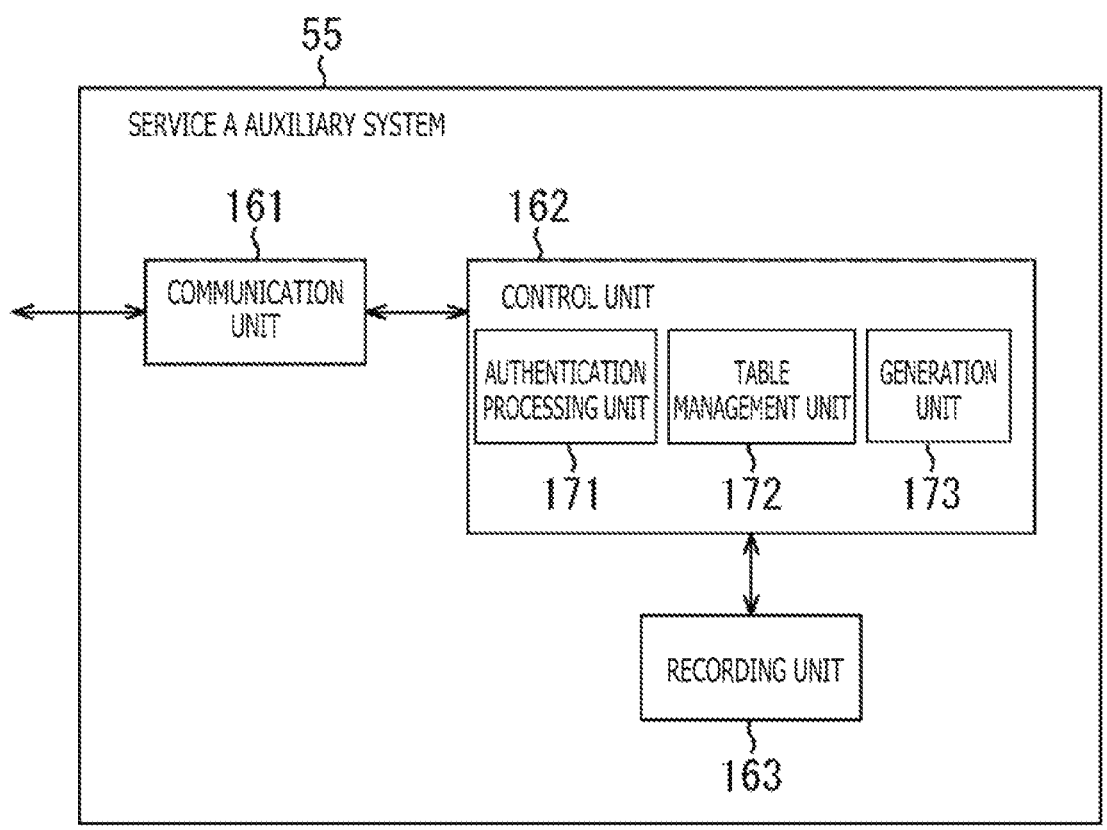
FIG. 5 is a view depicting an example of a configuration of a service A auxiliary system.

FIG. 5 is a view depicting an example of a more detailed configuration of the service A auxiliary system 55. While the service A auxiliary system 55 here is one information processing apparatus, the service A auxiliary system 55 may otherwise be configured from a plurality of apparatus or may be configured as part of the service A cloud server 54.

The service A auxiliary system 55 includes a communication unit 161, a control unit 162, and a recording unit 163.

The communication unit 161 transmits various kinds of information supplied from the control unit 162 to the individual apparatus of the service provision system through the communication network 56, or receives information transmitted thereto from the apparatus and supplies the received information to the control unit 162. In other words, the communication unit 161 acquires various kinds of information through the communication network 56 or supplies various kinds of information.

The control unit 162 controls the components of the service A auxiliary system 55. The control unit 162 includes an authentication processing unit 171, a table management unit 172, and a generation unit 173.

The authentication processing unit 171 performs an authentication process of the other-service IC card 52 (nonstandard ID). In particular, in the authentication process, authentication of whether the other-service IC card 52 is a legitimate card, namely, whether the user indicated by the nonstandard ID is a legitimate user, is performed.

The table management unit 172 performs management of an ID correspondence table such as an ID reading out process of the standard ID associated with the nonstandard ID using the ID correspondence table described above. The generation unit 173 generates service utilization additional information on the basis of information acquired from the client apparatus 62.

The recording unit 163 records various kinds of information supplied from the control unit 162 or supplies the recorded information to the control unit 162.

Figure 6:
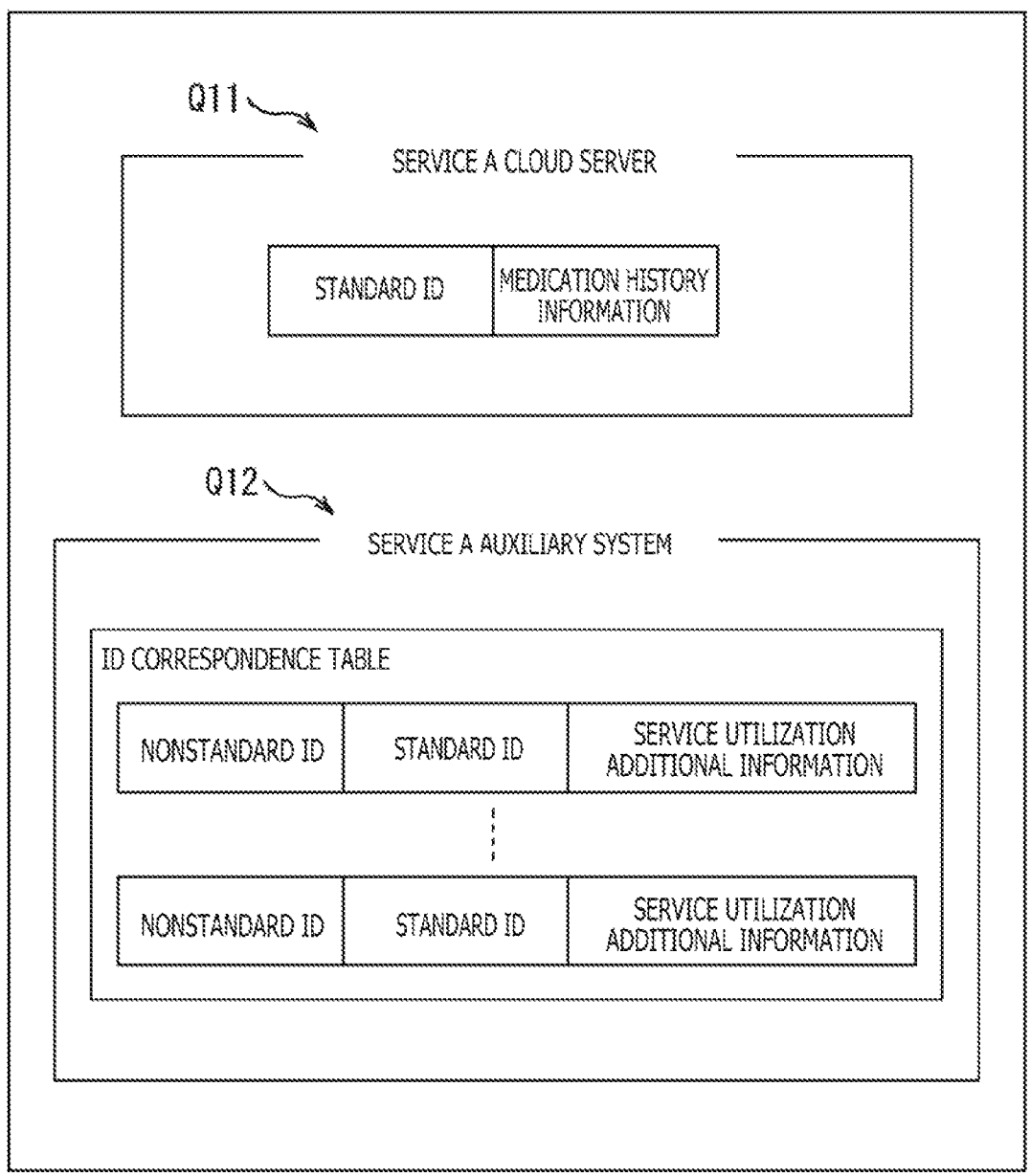
FIG. 6 is a view illustrating information managed by the service A cloud server and the service A auxiliary system.

Further, at least information depicted in FIG. 6 is recorded in the recording unit 123 of the service A cloud server 54 described hereinabove and the recording unit 163 of the service A auxiliary system 55.

In particular, as indicated by an arrow mark Q11 of FIG. 6, a standard ID of each user and medication history information of each user are recorded in an associated relationship with each other in the recording unit 123 of the service A cloud server 54.

Further, as indicated by an arrow mark Q12, an ID correspondence table indicative of a combination of a nonstandard ID and a standard ID associated with the nonstandard ID is recorded in the recording unit 163 of the service A auxiliary system 55.

It is to be noted that also information indicative of a type of the other-service IC card 52 may be recorded in an associated relationship with the nonstandard ID in the ID correspondence table such that it can be distinguished of which other-service IC card 52 the nonstandard ID is. In this case, even when a same nonstandard ID is recorded in an other-service IC card 52 of a different type, a correct standard ID can be obtained from the information indicating the type and the nonstandard ID. Further, while a method for reading out a standard ID corresponding to a nonstandard ID using the ID correspondence table is described here, the standard ID may otherwise be obtained by arithmetic operation or the like for the nonstandard ID.

Furthermore, in the ID correspondence table, also service utilization additional information is recorded in an associated relationship with the standard ID.

This service utilization additional information is utilized when the user receives provision of a service using the nonstandard ID, and it is originally desirable that the service utilization additional information is recorded in the other-service IC card 52. However, since there is also a case in which service utilization additional information cannot be recorded in the other-service IC card 52, the service utilization additional information here is recorded in the recording unit 163. It is to be noted that, in the case where the service utilization additional information can be recorded into the other-service IC card 52, the service utilization additional information may be recorded into the other-service IC card 52.

Incidentally, in the case where the user receives provision of a service using the service A IC card 51, the user would hold the service A IC card 51 over the IC card reader 61 as described above. Consequently, the read-write controlling unit 92 of the client apparatus 62 acquires a standard ID, authentication information, and service utilization additional information from the service A IC card 51 through the IC card reader 61 and supplies them to the control unit 93.

Then, the control unit 93 supplies a transmission request of medication history information together with the standard ID, the authentication information, and the service utilization additional information supplied from the read-write controlling unit 92 to the communication unit 91, and the communication unit 91 transmits the standard ID, the authentication information, the service utilization additional information, and the transmission request to the service A cloud server 54 through the communication network 56. It is to be noted that the service utilization additional information may be transmitted to the service A cloud server 54 as occasion demands and may not necessarily be transmitted.

Further, since the service A cloud server 54 transmits medication history information and service utilization additional information to the client apparatus 62 in response to the transmission request, the communication unit 91 of the client apparatus 62 receives the medication history information and the service utilization additional information transmitted thereto and supplies them to the control unit 93. Then, the control unit 93 suitably processes the medication history information and the service utilization additional information obtained in this manner and then supplies them to the display unit 96 so as to be displayed or the like thereby to provide a service to the user.

<Process Upon Registration of Other-Service IC Card>

Subsequently, operation of the service provision system depicted in FIG. 2 is described.

First, a process performed upon registration of the other-service IC card 52 is described with reference to a flow chart of FIG. 7. In particular, a registration request process by the service A client system 53, a registration process by the service A auxiliary system 55, and an issuance process by the service A cloud server 54 are described.

For example, in the case where a user who does not receive issuance of a service A IC card 51 intends to receive provision of a service utilizing the other-service IC card 52, the user would go to a pharmacy or the like in which the service A client system 53 is installed and request registration of the other-service IC card 52. An employee of the pharmacy or the like who receives the request will operate the inputting unit 94 of the client apparatus 62 to input information necessary for generation of service utilization additional information.

Consequently, at step S11, the control unit 93 acquires information inputted by the employee or the like for generating service utilization additional information in response to a signal supplied from the inputting unit 94. For example, the information for generating service utilization additional information is information relating to the user itself such as the name, the birth date, an address, sexuality, an insurance card number and so forth of the user.

It is to be noted that, in the following, the information for generating service utilization additional information is referred to also as input information. Further, as the acquisition method of the input information, the input information may be acquired not by an inputting operation for the inputting unit 94, but may be acquired from some other apparatus through the communication network 56 or may be read out partly or entirely from the other-service IC card 52. Furthermore, not the input information may be acquired but the service utilization additional information itself may be acquired.

After the information for generating service utilization additional information is inputted, the user would hold the other-service IC card 52 possessed thereby over the IC card reader 61.

Consequently, at step S12, the IC card reader 61 acquires the nonstandard ID and the authentication information from the other-service IC card 52 under the control of the read-write controlling unit 92 and supplies them to the read-write controlling unit 92. In other words, the nonstandard ID and the authentication information are read out.

The read-write controlling unit 92 supplies the nonstandard ID and the authentication information supplied from the IC card reader 61 to the communication unit 91 through the control unit 93. Further, the control unit 93 supplies also the acquired input information to the communication unit 91.

At step S13, the communication unit 91 transmits the nonstandard ID, the authentication information, and the input information to the service A auxiliary system 55 through the communication network 56.

After the nonstandard ID and the authentication information are transmitted in this manner, at step S21, the communication unit 161 of the service A auxiliary system 55 receives the nonstandard ID, the authentication information, and the input information transmitted thereto from the client apparatus 62 and supplies them to the control unit 162.

At step S22, the authentication processing unit 171 of the control unit 162 performs an authentication process of the other-service IC card 52 on the basis of the received authentication information.

In particular, for example, in the other-service IC card 52, predetermined data to be used for authentication and signature information obtained from the predetermined data are recorded as authentication information. Further, the service A auxiliary system 55 acquires a public key for authentication in advance from a business operator or the like who manages the other-service IC card 52 such as an issuance source or the like of the other-service IC card 52 and retains them.

In such a case as described above, the authentication processing unit 171 performs a hash operation for predetermined data as the authentication information and decodes a hash value obtained as a result of the hash operation with the public key acquired in advance. Then, the authentication processing unit 171 compares a value obtained by the decoding and the signature information as the authentication information with each other and decides, in the case where they coincide with each other, that the other-service IC card 52 is authenticated, in other words, that the other-service IC card 52 is a legitimate one.

At step S23, the authentication processing unit 171 decides whether or not the other-service IC card 52 is authenticated.

In the case where it is decided at step S23 that the other-service IC card 52 is not authenticated, in other words, in the case where it is decided that the other-service IC card 52 is not a legitimate one, the control unit 162 generates response information that the service cannot be utilized with the other-service IC card 52.

Then, the control unit 162 supplies the generated response information to the communication unit 161, and the processing advances to step S24.

At step S24, the communication unit 161 transmits the response information supplied from the control unit 162 and representing that the service cannot be utilized to the client apparatus 62 through the communication network 56, and the registration process comes to an end.

In contrast, in the case where it is decided at step S23 that the other-service IC card 52 is authenticated, in other words, in the case where it is decided that the other-service IC card 52 is a legitimate one, the control unit 162 supplies an issuance request of a standard ID to the communication unit 161, and the processing advances to step S25.

At step S25, the communication unit 161 transmits the issuance request supplied from the control unit 162 to the service A cloud server 54 through the communication network 56.

Consequently, at step S51, the communication unit 121 of the service A cloud server 54 receives the issuance request of a standard ID transmitted from the service A auxiliary system 55 and supplies it to the control unit 122.

At step S52, the ID issuance unit 132 of the control unit 122 issues a standard ID in response to the issuance request. At this time, the ID issuance unit 132 refers to the standard IDs recorded in the recording unit 123 as occasion demands to issue a standard ID such that this may not overlap.

Further, the ID issuance unit 132 supplies the standard ID to the recording unit 123 so as to be recorded as occasion demands and supplies the standard ID to the communication unit 121.

At step S53, the communication unit 121 transmits the standard ID supplied from the ID issuance unit 132 to the service A auxiliary system 55 through the communication network 56, and the issuance process comes to an end.

It is to be noted that, while an example in which a standard ID is issued by the service A cloud server 54 is described here, a standard ID may be issued otherwise by the service A auxiliary system 55 or a standard that does not overlap may be inputted by a user or the like.

After the standard ID is issued, at step S26, the communication unit 161 of the service A auxiliary system 55 receives the standard ID transmitted from the service A cloud server 54 and supplies it to the control unit 162.

At step S27, the table management unit 172 registers the nonstandard ID received at step S21 and the standard ID received at step S26 in an associated relationship with each other.

In particular, the table management unit 172 generates an ID correspondence table including the nonstandard ID and the standard ID associated with each other and supplies the ID correspondence table to the recording unit 163 so as to be recorded thereby to register the set of the nonstandard ID and standard ID associated with each other.

It is to be noted that, while an example in which the nonstandard ID is recorded as it is in an associated relationship with a standard ID into an ID correspondence table is described here, a hash value of the nonstandard value may be determined such that the resulting hash value and the standard ID are recorded in an associated relationship with each other into an ID correspondence table. In such a case as just described, upon reading out of the standard ID corresponding to the nonstandard ID, hash operation is performed for the nonstandard ID to perform reading out of the standard ID.

At step S28, the generation unit 173 generates service utilization additional information on the basis of the input information received at step S21.

For example, the generation unit 173 suitably extracts necessary information or the like from the input information to make information configuring service utilization additional information or processes the information such as to perform hash operation for the extracted information as occasion demands to make information that configures service utilization additional information.

At step S29, the table management unit 172 registers the generated service utilization additional information. In particular, the table management unit 172 supplies the service utilization additional information to the recording unit 163 such that the service utilization additional information is recorded in an associated relationship with the standard ID received at step S26 into the ID correspondence table of the recording unit 163. Consequently, the nonstandard ID, standard ID, and the service utilization additional information are recorded in an associated relationship with each other into the ID correspondence table.

Further, the control unit 162 generates response information that registration of the other-service IC card 52 is completed and supplies it to the communication unit 161.

At step S30, the communication unit 161 transmits response information that registration is completed to the service A client system 53 through the communication network 56, and the registration process comes to an end.

Further, after the process at step S24 or S30 is performed and response information is transmitted, at step S14, the communication unit 91 of the client apparatus 62 configuring the service A client system 53 receives the response information transmitted thereto from the service A auxiliary system 55 and supplies it to the control unit 93.

At step S15, the control unit 93 supplies the response information supplied from the communication unit 91 to the display unit 96 so as to be displayed, and the registration request process comes to an end.

By this process, the response information that registration is completed or the response information that the service cannot be utilized is displayed on the display unit 96. If the registration information that registration is completed is displayed and the registration is completed, then the user can thereafter utilize the service utilizing the registered other-service IC card 52.

In the service provision system, after authentication of the other-service IC card 52 is performed, a standard ID is issued newly to the user, and the standard ID and the nonstandard ID recorded in the other-service IC card 52 are recorded in an associated relationship with each other and also service utilization additional information is recorded in such a manner as described above.

Consequently, the user can utilize a service using the other-service IC card 52 possessed already without receiving issuance of the service A IC card 51, and the convenience can be improved. Especially, by recording also the service utilization additional information into the service A auxiliary system 55 in advance, even in the case where, upon utilization of a service, not only the standard ID but also other information, namely, service utilization additional information, are necessitated, the user can receive provision of the service without inputting the service utilization additional information every time.

According to the present technology, it becomes possible to use, for example, the other-service IC card 52 possessed already by a user as a card for providing an aimed new service without having any influence on an existing service for which the other-service IC card 52 is utilized.

Especially, in the case where the other-service IC card 52 is a public card that has a facial photograph of a user and can be utilized as an identification document like a driver's license or a My Number card, the card can be prevented from being utilized by a user other than the principal.

Furthermore, also in the case where the other-service IC card 52 is a non-writable card like an IC driver's license, by using the present technology, the other-service IC card 52 can be utilized as a card for a different service. Especially, as regards sensitive information, for example, like an electronic medication notebook, since it is emphasized to disclose it only to the principal or a third party admitted by the principal, such a function as described above is significant.

<Process Upon Service Utilization in which Other-Service IC Card is Used>

Now, a process performed when a user utilizes the other-service IC card 52 registered already to receive provision of a service is described.

First, a service utilization process performed by the service A client system 53 is described with reference to a flow chart of FIG. 8.

In the case where a user intends to receive provision of a service, the user would hold the other-service IC card 52 over the IC card reader 61.

Consequently, processes at steps S81 and S82 are performed such that nonstandard ID and authentication information read out from the other-service IC card 52 are transmitted to the service A auxiliary system 55. It is to be noted that the processes at steps S81 and S82 are similar to the processes at steps S12 and S13 of FIG. 7 individually, and therefore, description of them is omitted. However, at step S82, transmission of input information is not performed.

After the nonstandard ID and the authentication information are transmitted to the service A auxiliary system 55, the service A auxiliary system 55 performs an authentication process based on the authentication information, and in the case where the other-service IC card 52 is authenticated, the user can utilize the service. In contrast, in the case where the other-service IC card 52 is not authenticated, response information that the service cannot be utilized is transmitted from the service A auxiliary system 55.

At step S83, the control unit 93 decides whether or not the service can be utilized. For example, in the case where response information that the service cannot be utilized is transmitted from the service A auxiliary system 55, it is decided that the service cannot be utilized.

In the case where it is decided at step S83 that the service can be utilized, at step S84, the client apparatus 62 executes a process for receiving provision of the service, and the service utilization process comes to an end.

In particular, for example, the communication unit 91 receives display data of medication history information transmitted from the service A cloud server 54 and supplies the display data to the control unit 93, and the control unit 93 supplies the display data to the display unit 96 such that the display unit 96 displays the medication history information.

On the other hand, in the case where it is decided at step S83 that the service cannot be utilized, at step S85, the communication unit 91 receives the response information transmitted from the service A auxiliary system 55 and representing that the service cannot be utilized and supplies the response information to the control unit 93.

At step S86, the control unit 93 supplies the response information supplied from the communication unit 91 and representing that the service cannot be utilized to the display unit 96 so as to be displayed, and the service utilization process comes to an end.

The service A client system 53 acquires a nonstandard ID and authentication information from the other-service IC card 52 and transmits them to the service A auxiliary system 55 in such a manner as described above. Consequently, the user can receive provision of the service from the service A cloud server 54 without the necessity for a cumbersome operation such as inputting of additional information or the like.

By making it possible to receive provision of a service even if the other-service IC card 52 registered already in this manner, the convenience can be improved.

Figure 8:
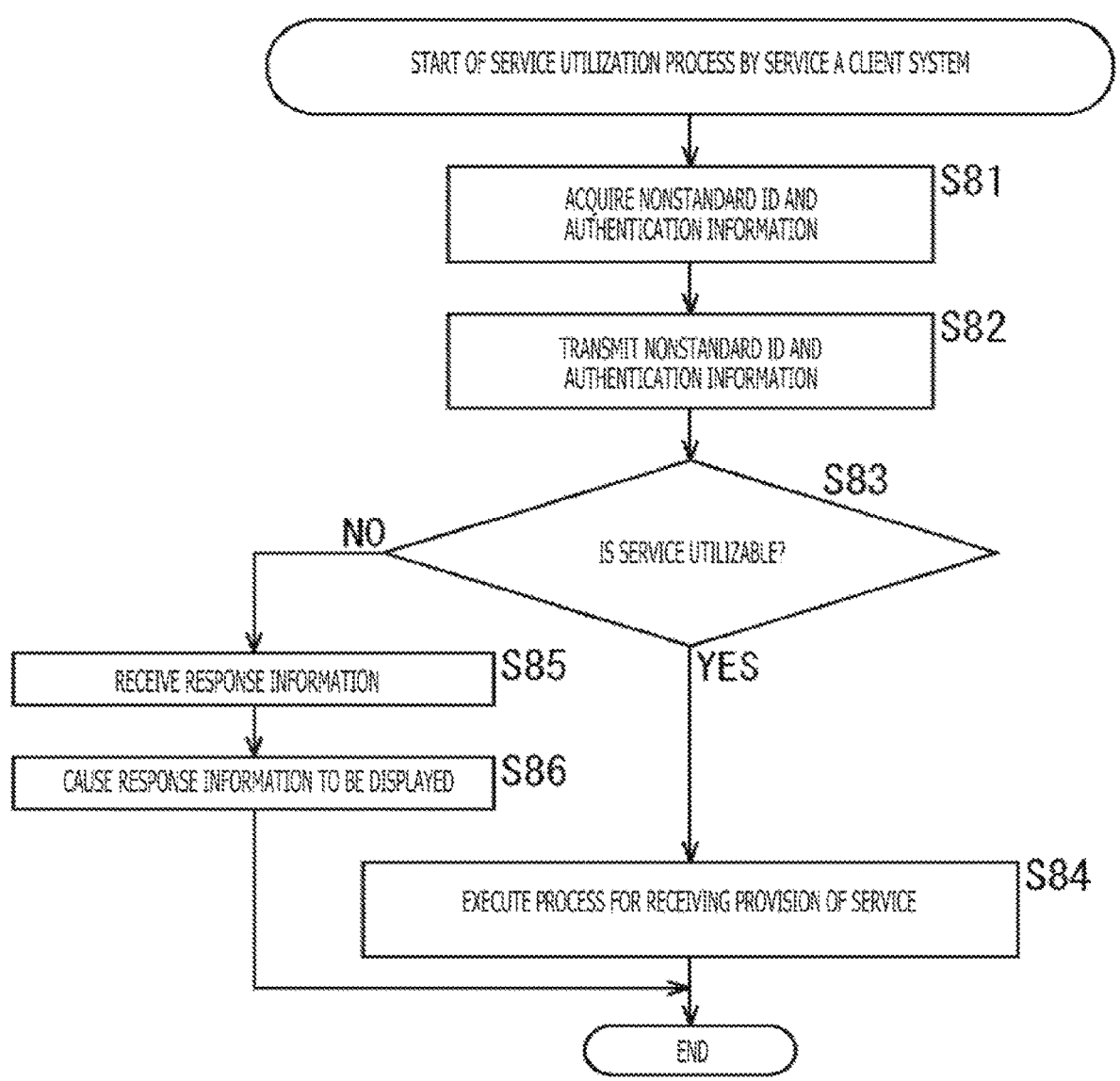
FIG. 8 is a flow chart illustrating a service utilization process.

Now, a process performed by the service A auxiliary system 55 and the service A cloud server 54 when the service utilization process described hereinabove with reference to FIG. 8 is described. In particular, a service provision auxiliary process by the service A auxiliary system 55 and a service provision process by the service A cloud server 54 are described below with reference to a flow chart of FIG. 9.

Figure 7:
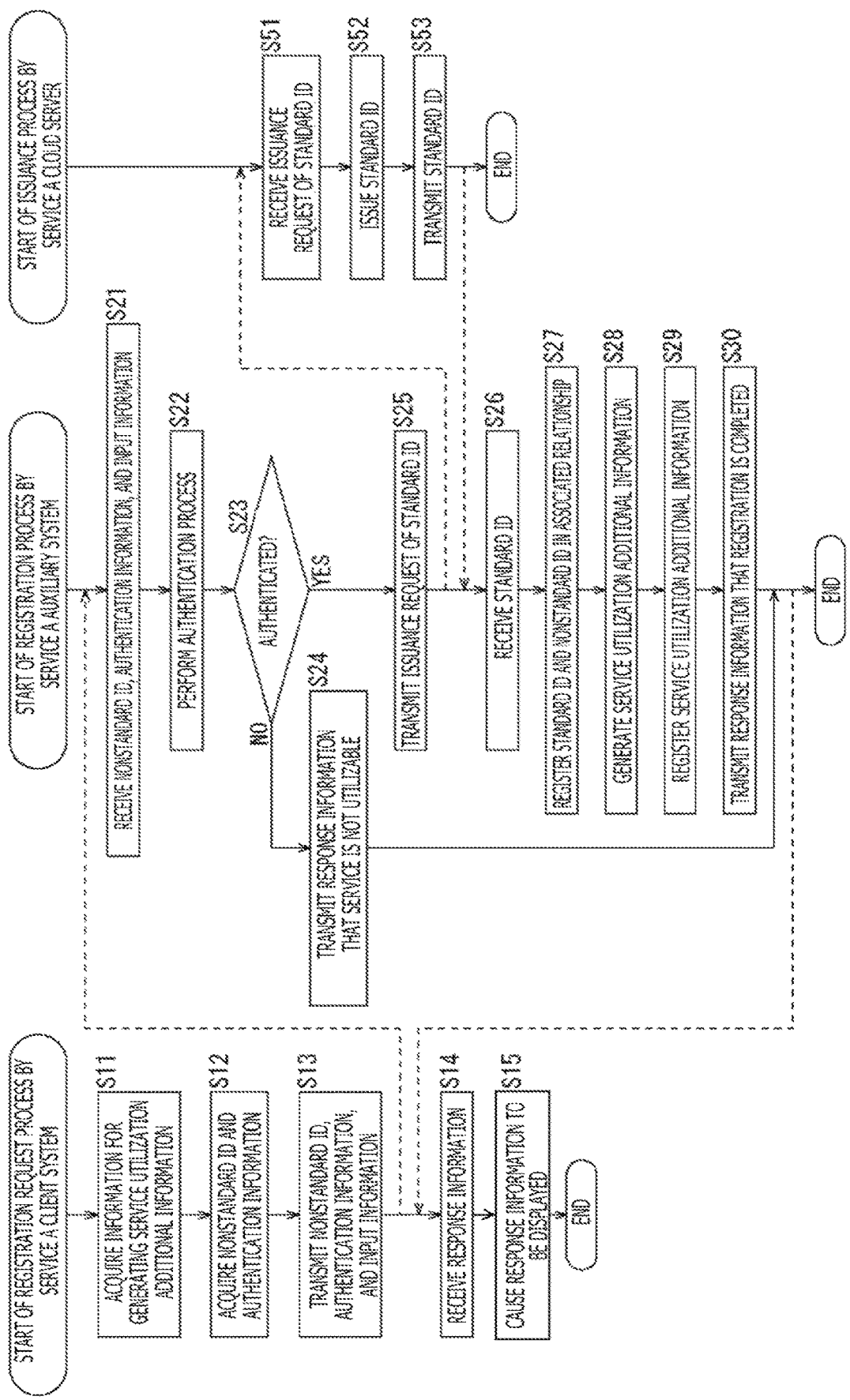
FIG. 7 is a flow chart illustrating a registration request process, a registration process, and an issuance process.

It is to be noted that processes at steps S111 to S114 are similar to the processes at steps S21 to S24 of FIG. 7 individually, and therefore, description of them is omitted. However, at step S111, input information is not received.

In the case where it is decided at step S113 that the other-service IC card 52 is authenticated, at step S115, the table management unit 172 reads out, from the ID correspondence table recorded in the recording unit 163, the standard ID issued to the user identified with the nonstandard ID received at step S111. In other words, the standard ID associated with the nonstandard ID is read out.

At step S116, the table management unit 172 acquires service utilization additional information.

In particular, the table management unit 172 reads out, from the ID correspondence table of the recording unit 163, service utilization additional information recorded in an associated relationship with the standard ID obtained at step S115. Then, the control unit 162 supplies the standard ID and the service utilization additional information to the communication unit 161.

At step S117, the communication unit 161 transmits the standard ID and the service utilization additional information supplied from the control unit 162 to the service A cloud server 54 through the communication network 56. Further, the control unit 162 controls the communication unit 161 to instruct the service A cloud server 54 to access to the service A client system 53, namely, to provide a service.

After the standard ID and the service utilization additional information are transmitted in this manner, the service provision auxiliary process comes to an end.

Further, at step S141, the communication unit 121 of the service A cloud server 54 receives the standard ID and the service utilization additional information transmitted from the service A auxiliary system 55 and supplies them to the control unit 122.

Then at step S142, the service provision unit 131 provides the service on the basis of the standard ID and the service utilization additional information supplied from the communication unit 121, and the service provision process comes to an end.

In particular, for example, the service provision unit 131 reads out medication history information recorded in an associated relationship with the standard ID from the recording unit 123 and generates, from the medication history information and the service utilization additional information, display data of an image, in which the medication history information and the name and so forth of the user as the service utilization additional information are to be displayed. Further, the service provision unit 131 supplies the generated display data to the communication unit 121 and causes the display data to be transmitted to the service A client system 53 designated by the service A auxiliary system 55.

It is to be noted that an example in which the service A cloud server 54 receives a designation of the service A client system 53 that is a service provision destination from the service A auxiliary system 55 is described here. However, the service A cloud server 54 may receive the nonstandard ID and the authentication information from the service A client system 53 and instruct the service A auxiliary system 55 to perform an authentication process and supply of the standard ID and the service utilization additional information.

The service A auxiliary system 55 performs an authentication process based on authentication information and acquires a standard ID and service utilization additional information on the basis of the nonstandard ID in such a manner as described above. Consequently, a service can be provided also to a user who possesses the other-service IC card 52 using the standard ID and the service utilization additional information, and the convenience can be improved.

<Modification 1 to First Embodiment>
<Service Utilization Additional Information>

It is to be noted that, in the foregoing, an example in which service utilization additional information is recorded as it is in the service A auxiliary system 55 is described. However, some of other-service IC cards 52 such as, for example, a My Number card has information recorded therein, which can be utilized as part or all of the service utilization additional information such as a kanji full name or a kana full name, the birth date or the like.

Therefore, information that is recorded in an other-service IC card 52 and can be utilized as part or all of the service utilization additional information may be used as service utilization additional information corresponding information such that service utilization additional information is generated using the service utilization additional information corresponding information.

Figure 10:
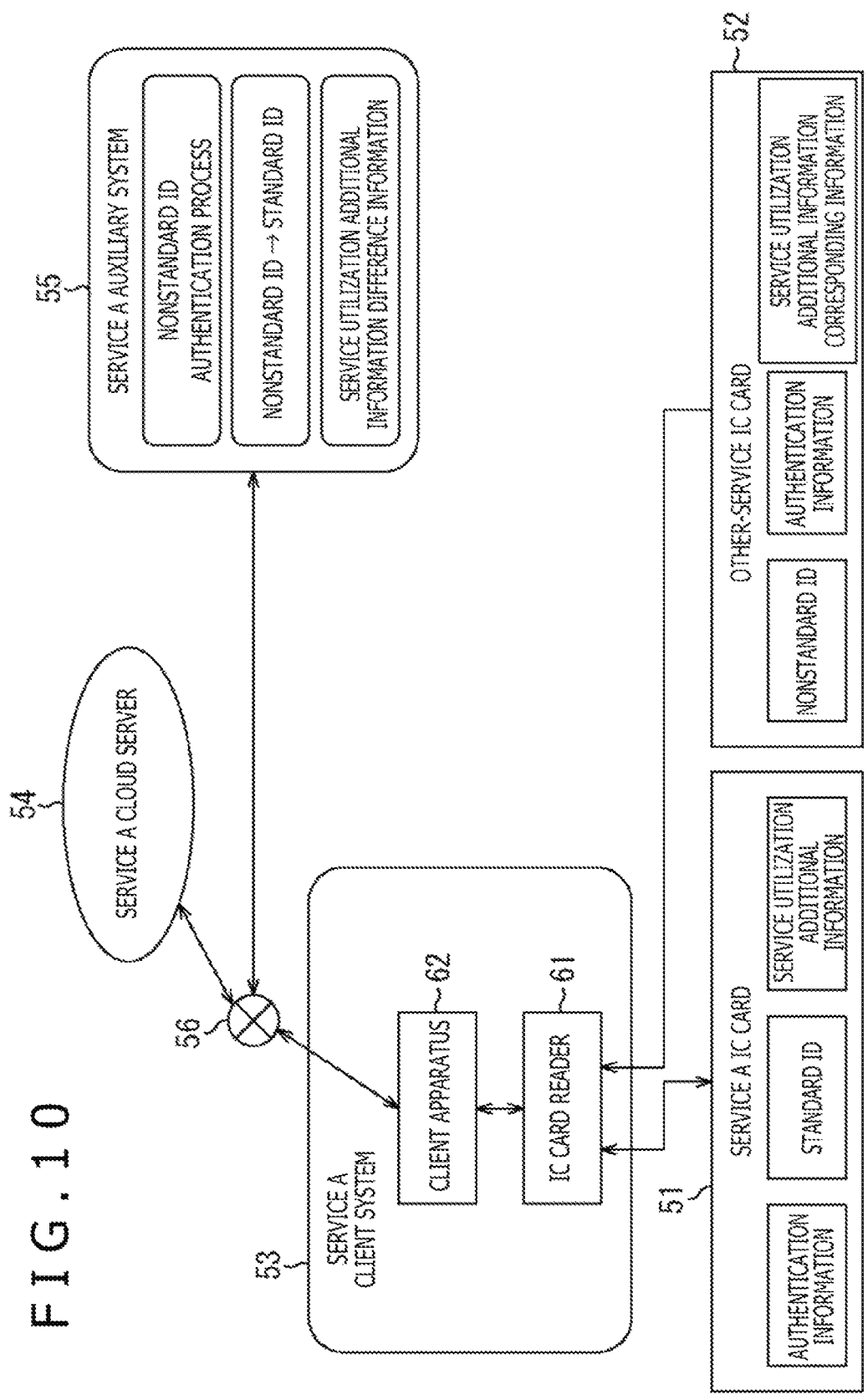
FIG. 10 is a view depicting an example of a configuration of a service provision system.

In such a case as just described, for example, as depicted in FIG. 10, in the service provision system, service utilization additional information difference information that is information obtained by removing service utilization additional information corresponding information from the service utilization additional information is recorded into the service A auxiliary system 55. It is to be noted that, in FIG. 10, portions corresponding to those in the case in FIG. 2 are denoted by the same reference characters, and description of the same is omitted.

In this example, in the case where the user is to receive provision of a service utilizing an other-service IC card 52, service utilization additional information is generated from the service utilization additional information corresponding information recorded in the other-service IC card 52 and the service utilization additional information difference information recorded in the service A auxiliary system 55 and is utilized for provision of the service.

It is to be noted that, when information corresponding to the service utilization additional information is all recorded in an other-service IC card 52, service utilization additional information difference information is not recorded into the service A auxiliary system 55. On the other hand, when information that can be utilized as the service utilization additional information is recorded not at all in the other-service IC card 52, the service utilization additional information is recorded into the service A auxiliary system 55.

<Process Upon Registration of Other-Service IC Card>

Now, operation of the service provision system that is performed in the case where service utilization additional information difference information is recorded into the service A auxiliary system 55 is described.

First, a registration request process by the service A client system 53 and a registration process by the service A auxiliary system 55 are described with reference to a flow chart of FIG. 11.

Similarly as in the case described, for example, with reference to FIG. 7, a user who does not receive issuance of a service A IC card 51 would go to a pharmacy intending to receive provision of a service utilizing an other-service IC card 52 and request registration of the other-service IC card 52. Then, an employee of the pharmacy who receives the request would operate the inputting unit 94 of the client apparatus 62 to input information necessary for generation of service utilization additional information.

Consequently, at step S171, the control unit 93 acquires information for generating service utilization additional information inputted by the employee or the like in response to a signal supplied from the inputting unit 94. In other words, the input information is acquired.

Further, the user would hold the other-service IC card 52 possessed thereby over the IC card reader 61.

Consequently, at step S172, the IC card reader 61 acquires a nonstandard ID, authentication information, and service utilization additional information corresponding information from the other-service IC card 52 under the control of the read-write controlling unit 92 and supplies them to the read-write controlling unit 92.

It is to be noted that, although, in the case where information that can become service utilization additional information corresponding information is specifiable, it is made possible to read out only the information, which becomes service utilization additional information corresponding information, from the other-service IC card 52, in the case where the information that becomes service utilization additional information corresponding information cannot be specified, all information that can become service utilization additional information corresponding information is read out. In short, information relating to the user itself including service utilization additional information corresponding information is read out from the other-service IC card 52.

Further, from a communication format with the other-service IC card 52, for example, from a format of polling or from a structure of information, identification information or the like recorded in the other-service IC card 52, it is possible to specify of which type the other-service IC card 52 is like a driver's license or what the information recorded in the other-service IC card 52 is. In the following, the description is continued assuming that each piece of information recorded in the other-service IC card 52 is specifiable.

The read-write controlling unit 92 supplies the nonstandard ID, the authentication information, and the service utilization additional information corresponding information supplied from the IC card reader 61 to the communication unit 91 through the control unit 93. Further, the control unit 93 supplies the acquired input information to the communication unit 91.

At step S173, the communication unit 91 transmits the nonstandard ID, the authentication information, the service utilization additional information corresponding information, and the input information to the service A auxiliary system 55 through the communication network 56.

Consequently, at step S201, the communication unit 161 of the service A auxiliary system 55 receives the nonstandard ID, the authentication information, the service utilization additional information corresponding information, and the input information transmitted thereto from the client apparatus 62 and supplies them to the control unit 162.

After the nonstandard ID, the authentication information, the service utilization additional information corresponding information, and the input information are received, processes at steps S202 to S207 are executed. However, since the processes are similar to the processes at steps S22 to S27 of FIG. 7, description of them is omitted. Further, if an issuance request is transmitted at step S205, then the service A cloud server 54 performs the issuance process described hereinabove with reference to FIG. 7.

At step S208, the generation unit 173 generates service utilization additional information difference information on the basis of the service utilization additional information corresponding information and the input information received at step S201.

In particular, the generation unit 173 determines the remainder when the service utilization additional information corresponding information is excluded (removed) from within the input information as service utilization additional information difference information.

At step S209, the table management unit 172 registers the generated service utilization additional information difference information. In particular, the table management unit 172 supplies the service utilization additional information difference information to the recording unit 163 such that the service utilization additional information difference information is recorded in an associated relationship with the standard ID received at step S206 and included in the ID correspondence table.

After the service utilization additional information difference information is registered, a process at step S210 is performed and then the registration process comes to an end. However, since the process at step S201 is similar to the process at step S30 of FIG. 7, description of it is omitted.

Further, after the process at step S210 is performed, in the service A client system 53, processes at steps S174 and S175 are executed and the registration request process comes to an end. However, since the processes are similar to the processes at steps S14 and S15 of FIG. 7, description of them is omitted.

In this manner, the service A auxiliary system 55 does not register service utilization additional information as it is but registers only service utilization additional information difference information in the service utilization additional information from which the service utilization additional information corresponding information recorded in the other-service IC card 52 is excluded. Consequently, the amount of information to be recorded and retained in the service A auxiliary system 55 can be reduced, and also personal information to be managed by the service A auxiliary system 55 can be reduced.

<Process Upon Service Utilization Using Other-Service IC Card>

Figure 11:
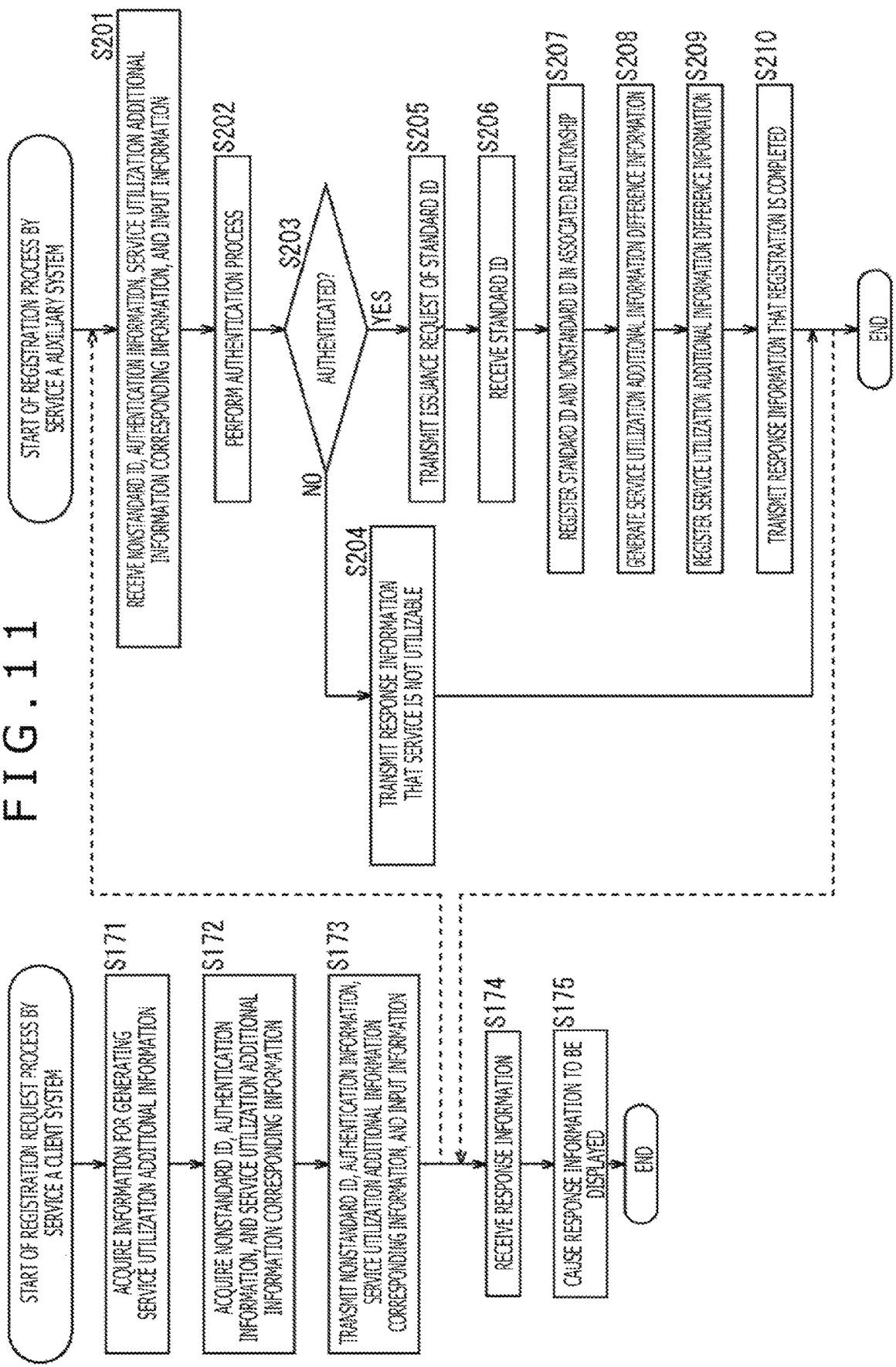
FIG. 11 is a flow chart illustrating a registration request process and a registration process.

Now, a process performed when a user receives provision of a service utilizing a registered other-service IC card 52 after the process described hereinabove with reference to FIG. 11 is performed is described.

First, a service utilization process performed by the service A client system 53 is described with reference to a flow chart of FIG. 12.

In the case where a user intends to receive provision of a service, the user would hold the other-service IC card 52 over the IC card reader 61.

Consequently, processes at steps S241 and S242 are performed and a nonstandard ID, authentication information, and service utilization additional information corresponding information read out from the other-service IC card 52 are transmitted to the service A auxiliary system 55. It is to be noted that, since the processes at steps S241 and S242 are similar to the processes at steps S172 and S173 of FIG. 11 individually, description of them is omitted. However, at step S242, transmission of the input information is not performed.

Further, after the nonstandard ID, the authentication information, and the service utilization additional information corresponding information are transmitted to the service A auxiliary system 55, processes at steps S243 to S246 are performed and the service utilization process comes to an end. However, since the processes are similar to the processes at steps S83 to S86 of FIG. 8, description of them is omitted.

In this manner, in the case where service utilization additional information corresponding information is recorded in the other-service IC card 52, upon service utilization, the service utilization additional information corresponding information is read out from the other-service IC card 52.

Figure 12:
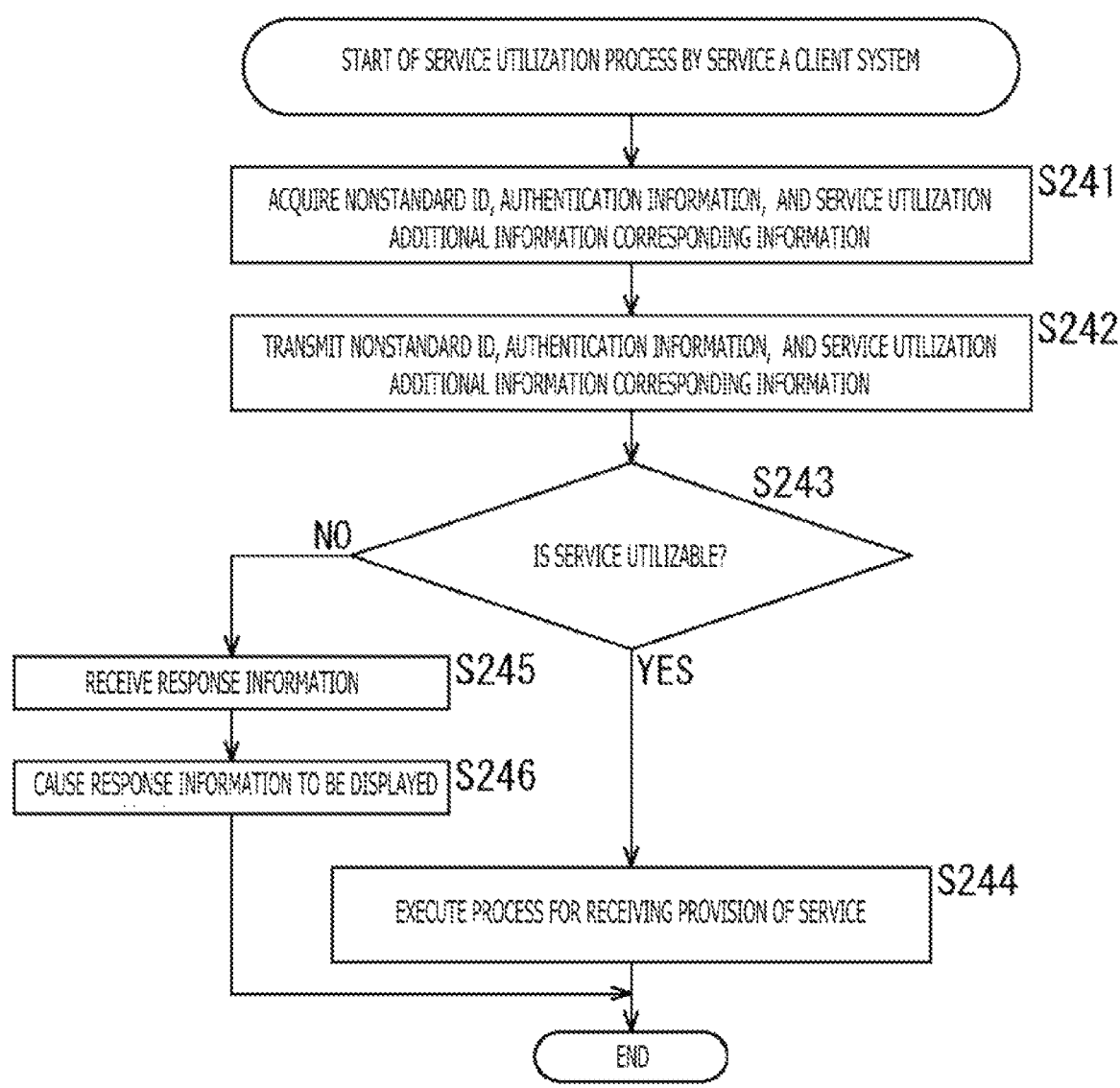
FIG. 12 is a flow chart illustrating a service utilization process.
Figure 13:
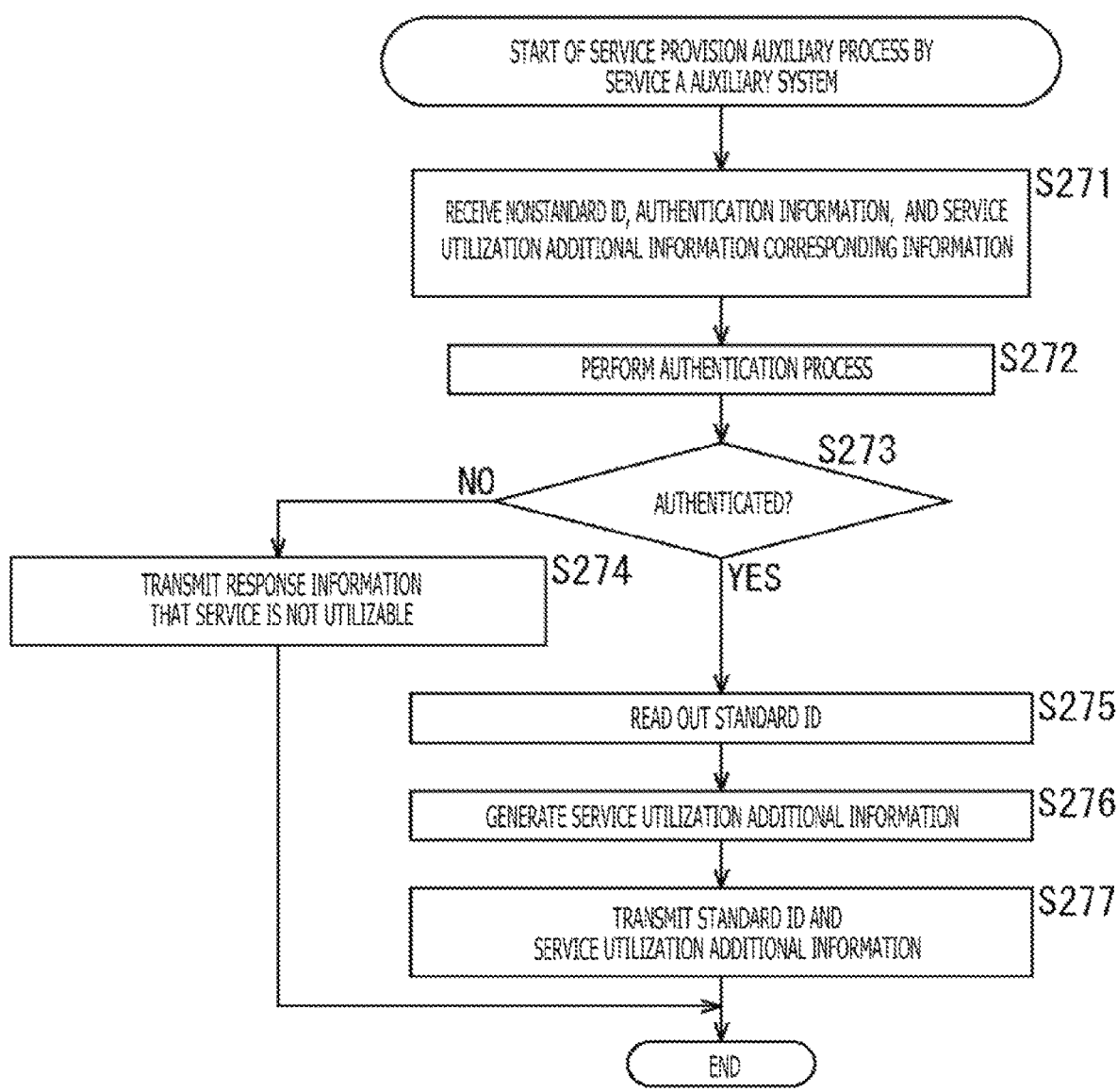
FIG. 13 is a flow chart illustrating a service provision auxiliary process.

Now, a process performed by the service A auxiliary system 55 when the service utilization process described hereinabove with reference to FIG. 12 is performed is described. In particular, a service provision auxiliary process by the service A auxiliary system 55 is described below with reference to a flow chart of FIG. 13.

At step S271, the communication unit 161 receives the nonstandard ID, the authentication information, and the service utilization additional information corresponding information transmitted thereto from the service A client system 53 by the process at step S242 of FIG. 12 and supplies them to the control unit 162.

Figure 9:
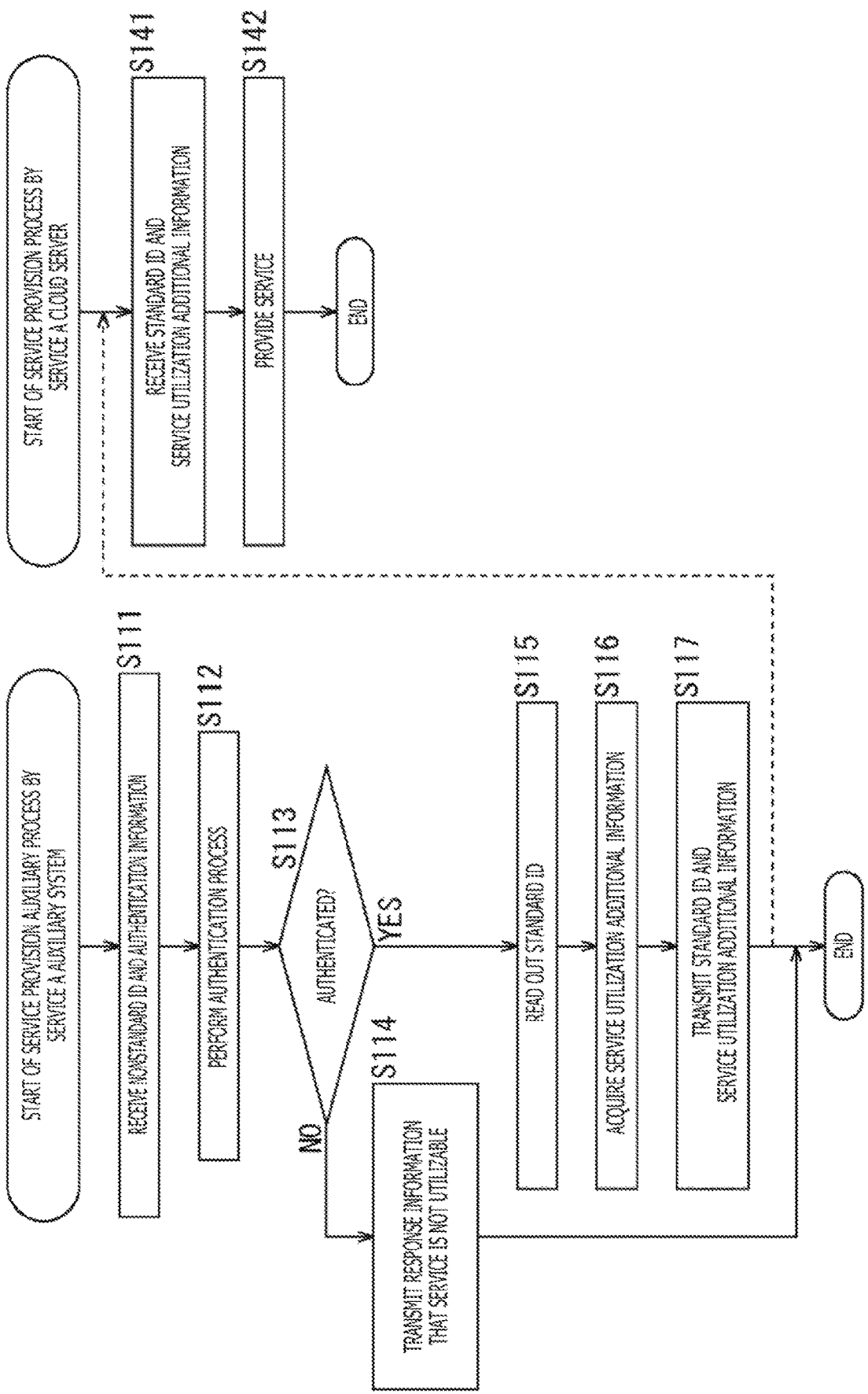
FIG. 9 is a flow chart illustrating a service provision auxiliary process and a service provision process.

Further, although processes at steps S272 to S275 are performed after the process at step S271, since the processes are similar to the processes at steps S112 to S115 of FIG. 9 individually, description of them is omitted.

At step S276, the control unit 162 generates service utilization additional information.

In particular, the table management unit 172 of the control unit 162 reads out the service utilization additional information difference information recorded in an associated relationship with the standard ID obtained at step S275 from the ID correspondence table of the recording unit 163. Then, the control unit 162 combines the read out service utilization additional information difference information and the service utilization additional information corresponding information received at step S271 and determines them as service utilization additional information.

It is to be noted that, while an example is described here in which service utilization additional information corresponding information and service utilization additional information difference information are combined to generate service utilization additional information, such information may be suitably subjected to conversion, arithmetic operation or the like to generate service utilization additional information.

In particular, the service utilization additional information corresponding information or the service utilization additional information difference information may be any information if part of the service utilization additional information can be obtained from the information. Accordingly, for example, information obtained by carrying out a conversion process or the like for the service utilization additional information corresponding information and information obtained by carrying out a conversion process or the like for the service utilization additional information difference information may be combined to generate service utilization additional information.

After the service utilization additional information is obtained in this manner, a process at step S277 is performed and the service provision auxiliary process comes to an end. However, since the process at step S277 is similar to the process at step S117 of FIG. 9, description of it is omitted. Further, after the process at step S277 is performed, the service A cloud server 54 performs a process similar to the service provision process described hereinabove with reference to FIG. 9.

The service A auxiliary system 55 acquires service utilization additional information corresponding information from the service A client system 53 and combines the service utilization additional information corresponding information with the service utilization additional information difference information recorded in the service A auxiliary system 55 itself to obtain service utilization additional information in such a manner as described above. Consequently, the information amount of information to be recorded in the service A auxiliary system 55 can be reduced. Further, since information is recorded divisionally into the service A auxiliary system 55 and the other-service IC card 52, also the security can be improved.

It is to be noted that the service A client system 53 may acquire a standard ID and service utilization additional information or the standard ID and the service utilization additional information difference information from the service A auxiliary system 55. In such a case as just described, at step S277, the standard ID and the service utilization additional information are transmitted to the service A client system 53, and in the service A client system 53, the communication unit 91 receives and supplies the standard ID and the service utilization additional information to the control unit 93.

Here, in the case where not service utilization additional information but service utilization additional information difference information is received, the control unit 93 generates service utilization additional information from the service utilization additional information difference information and the service utilization additional information corresponding information. Then, the control unit 93 supplies the standard ID and the service utilization additional information to the communication unit 91 so as to be transmitted to the service A cloud server 54 and receives provision of the service from the service A cloud server 54. Further, in this case, at step S242 of FIG. 12, the service utilization additional information corresponding information may not be transmitted.

<Modification 2 to First Embodiment>
<Service Utilization Additional Information>

Incidentally, in the first embodiment described above, in the service provision system, a user who receives provision of a service can use both the service A IC card 51 and the other-service IC card 52.

Here, although service utilization additional information such as, for example, an insurance card number or the like is recorded in the service A IC card 51, for the convenience when the other-service IC card 52 is utilized, the service utilization additional information such as an insurance card number or the like is recorded also in the service A auxiliary system 55. In short, the service utilization additional information is in a state in which it is recorded in both the service A IC card 51 and the service A auxiliary system 55.

Therefore, in the case where part of the service utilization additional information, for example, an insurance card number of the like is subject to some change, it is necessary to update both the service utilization additional information in the service A IC card 51 and the service utilization additional information in the service A auxiliary system 55. Further, in this case, even when only the service utilization additional information in one of them can be updated, it is preferable to provide a service using the latest service utilization additional information as far as possible.

Therefore, the latest service utilization additional information may be generated from the service utilization additional information in the service A IC card 51 and the service utilization additional information in the service A auxiliary system 55 such that a service is provided using the service utilization additional information, or the service utilization additional information may be updated suitably.

Figure 14:
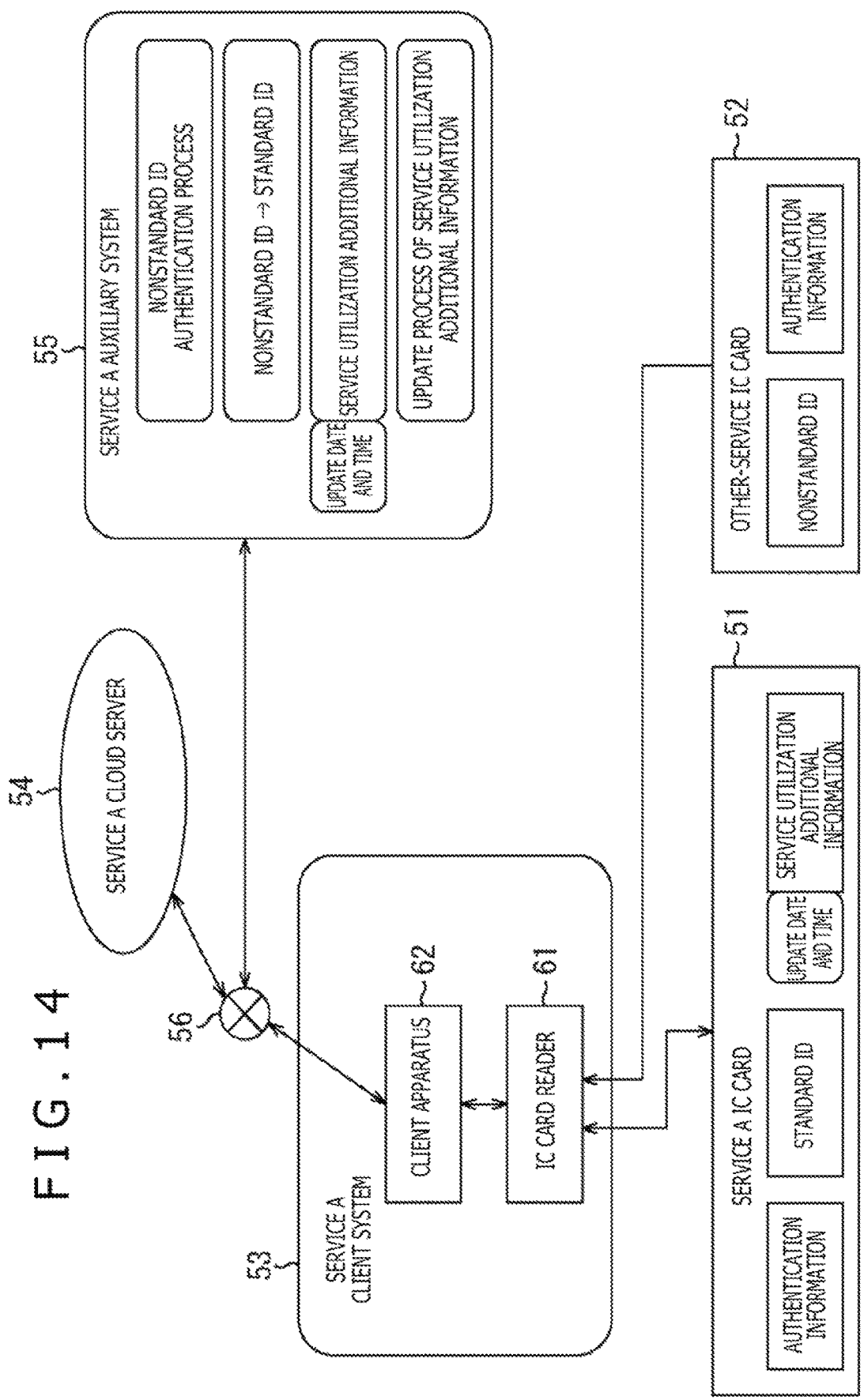
FIG. 14 is a view depicting an example of a configuration of a service provision system.

In such a case as described above, the service provision system is configured, for example, in such a manner as depicted in FIG. 14. It is to be noted that, in FIG. 14, portions corresponding to those in the case of FIG. 2 are denoted by the same reference characters, and description of the same is omitted suitably.

In this example, in the service A IC card 51, information (hereinafter referred to simply also as update date and time) indicative of update date and time of service utilization additional information is recorded in an associated relationship with the service utilization additional information.

Similarly, also in the service A auxiliary system 55, service utilization additional information and update date and time of the service utilization additional information are recorded in an associated relationship with each other. More particularly, in the service A auxiliary system 55, a nonstandard ID, a standard ID, update date and time, and service utilization additional information are recorded in an associated relationship with each other in the ID correspondence table. Further, the service A auxiliary system 55 has also a function for executing an update process for updating service utilization additional information.

In such a service provision system as described above, a case may be applicable in which, for example, the other-service IC card 52 is utilized to update the service utilization additional information in the service A auxiliary system 55. Further, in such a case as just described, when the user receives provision of a service utilizing the service A IC card 51 at a later date, the service utilization additional information in the service A IC card 51 can be updated as occasion demands.

For example, for the specification regarding whether there is the necessity to update the service utilization additional information in the service A IC card 51, in short, whether the service utilization additional information is the latest service utilization additional information, the update date and time recorded together with the service utilization additional information may be used. Alternatively, the specification regarding whether the service utilization additional information is the latest, in short, newer service utilization additional information, may be performed by designation by an inputting operation by the user or the like or may be performed on the basis of an information structure, identification information or the like of the service utilization additional information. For example, in such a case that, every time service utilization information is updated, part of it is incremented, by comparing the service utilization additional information with each other, it is possible to specify which service utilization additional information is the latest.

Furthermore, in the case in which a service is utilized using the service A IC card 51 in which the latest service utilization additional information is recorded, it is possible to update the service utilization additional information in the service A auxiliary system 55 using the service utilization additional information in the service A IC card 51.

It is to be noted here that an example in which the service utilization additional information in the service A IC card 51 is updated to the latest service utilization additional information, namely, to newer service utilization additional information is described. However, the updating is not limited to this, and naturally also it is possible to update service utilization additional information of some other apparatus such as a portable telephone set or the like that has a standard ID or service utilization additional information recorded and can utilize the service A.

Further, in the following, description is given taking a case in which service utilization additional information is recorded in the service A auxiliary system 55 as an example. However, also in the case in which service utilization additional information difference information is recorded in the service A auxiliary system 55, it is possible to update the service utilization additional information difference information in the service A auxiliary system 55 to the latest service utilization additional information difference information or to update the service utilization additional information in the service A IC card 51 to the latest service utilization additional information by a similar process.

<Update of Service Utilization Additional Information Upon Use of Other-Service IC Card>

Now, a process performed in the case where service utilization additional information is updated to the latest service utilization additional information is described. First, a process performed in the case where a user utilizes the other-service IC card 52 to update the service utilization additional information in the service A auxiliary system 55 is described.

Figure 15:
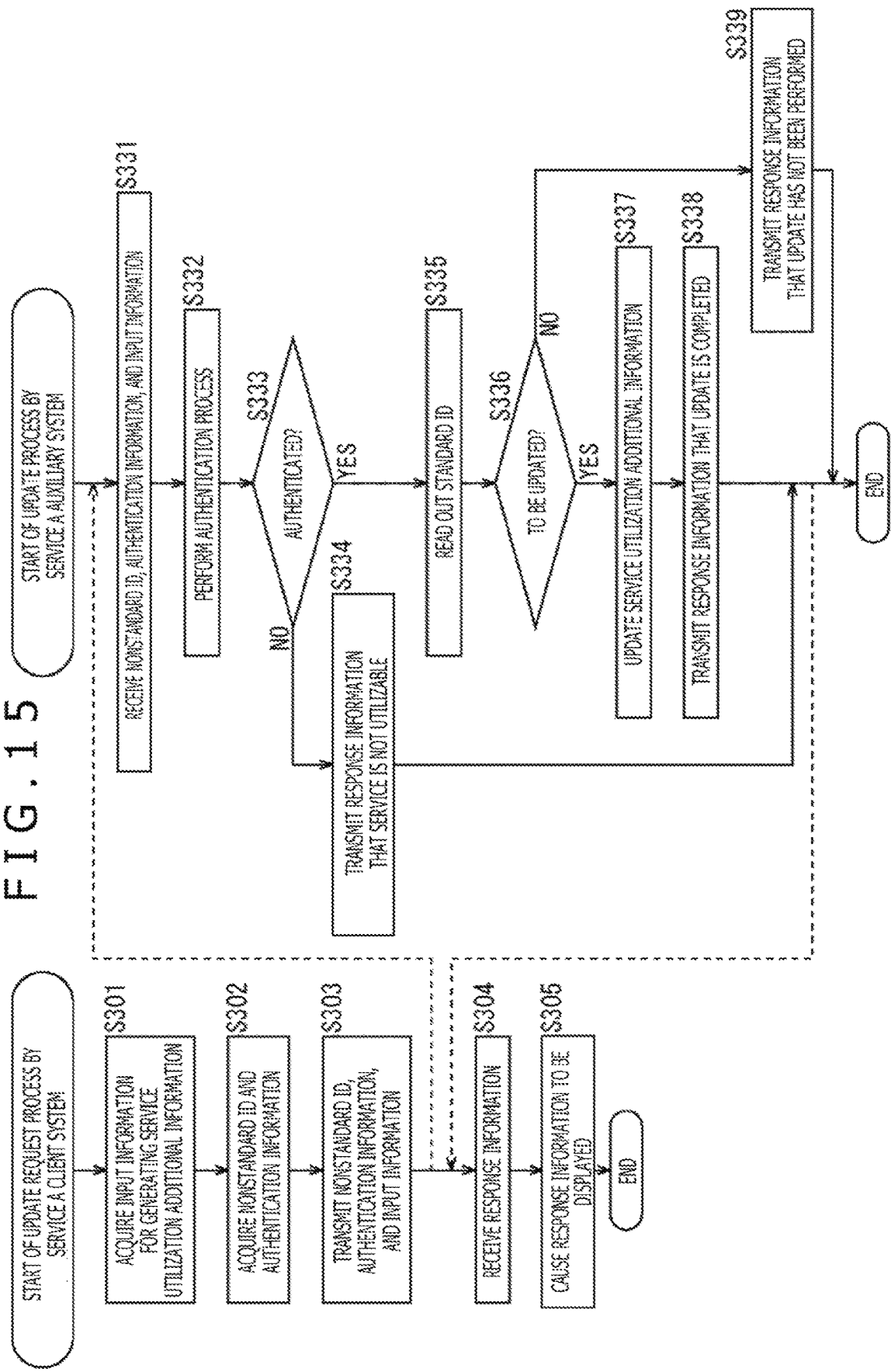
FIG. 15 is a flow chart illustrating an update request process and an update process.

In particular, an update request process by the service A client system 53 and an update process by the service A auxiliary system 55 are described below with reference to a flow chart of FIG. 15.

In this case, the user would go to a pharmacy or the like and request an update of service utilization additional information. An employee of the pharmacy or the like who receives the request would operate the inputting unit 94 of the client apparatus 62 to input information necessary for generation of the latest service utilization additional information.

Consequently, at step S301, the control unit 93 acquires input information inputted by the employee or the like for generating newer, namely, the latest, service utilization additional information in response to a signal supplied from the inputting unit 94.

It is to be noted that, as the acquisition method of input information, input information may be acquired not by an inputting operation by the inputting unit 94 but from some other apparatus or the like through the communication network 56, or part or all of input information may be read out from the other-service IC card 52. Alternatively, information for obtaining the latest service utilization additional information may be acquired as input information like that only an update portion of the service utilization additional information is acquired as input information.

After information for generating service utilization additional information is inputted, the user would hold the other-service IC card 52 possessed thereby over the IC card reader 61.

Consequently, processes at steps S302 and S303 are performed and the nonstandard ID, the authentication information, and the input information are transmitted to the service A auxiliary system 55. Since those processes are similar to the processes at steps S12 and S13 of FIG. 7, description of them is omitted.

When the nonstandard ID, the authentication information, and the input information are transmitted, the communication unit 161 of the service A auxiliary system 55 receives the nonstandard ID, the authentication information, and the input information transmitted thereto from the client apparatus 62 and supplies them to the control unit 162 at step S331.

Thereafter, processes at steps S332 to S335 are performed. However, since the processes are similar to the processes at steps S112 to S115 of FIG. 9, description of them is omitted.

After the standard ID is obtained at step S335, the table management unit 172 acquires update date and time and service utilization additional information recorded in an associated relationship with the obtained standard ID in the ID correspondence table of the recording unit 163. Further, the generation unit 173 generates the latest service utilization additional information from the input information received by the process at step S331.

At step S336, the table management unit 172 decides whether or not the service utilization additional information is to be updated.

In particular, for example, the table management unit 172 compares the service utilization additional information generated by the generation unit 173 and the service utilization additional information acquired from the ID correspondence table with each other and decides, in the case where the compared service utilization additional information does not coincide, that the service utilization additional information is to be updated. Alternatively, for example, in the case where the update date and time read out together with the service utilization additional information from the ID correspondence table is a date before a predetermined date such as current date and time, the table management unit 172 may determine that the service utilization additional information is to be updated.

Furthermore, although an example in which the service A auxiliary system 55 decides whether or not to update is described, alternatively, for example, a dialog screen image regarding whether updating is to be performed may be displayed on the display unit 96 of the client apparatus 62 in response to a result of the decision by the service A auxiliary system 55. In this case, for example, in the case where update is instructed finally by the user, a pharmacist or the like, it may be decided at step S336 that update is to be performed.

In the case where it is decided at step S336 that the service utilization additional information is to be updated, the table management unit 172 updates the service utilization additional information recorded in the ID correspondence table of the recording unit 163 at step S337. In particular, the table management unit 172 updates the service utilization additional information recorded in an associated relationship with the standard ID in the ID correspondence table by replacing the same with the latest service utilization additional information obtained from the input information received at step S331 and updates also the update date and time recorded in an associated relationship with the standard ID to the current date and time.

After the control unit 162 updates the service utilization additional information, it generates response information that update is completed and supplies the response information to the communication unit 161.

At step S338, the communication unit 161 transmits the response information supplied from the control unit 162 and representing that update is completed to the service A client system 53 through the communication network 56, and the update process comes to an end.

On the other hand, in the case where it is decided at step S336 that service utilization additional information is not to be updated, the control unit 162 generates response information representing that update is not performed and supplies the response information to the communication unit 161, whereafter the processing advances to step S339.

At step S339, the communication unit 161 transmits the response information supplied thereto from the control unit 162 and representing that update is not performed to the service A client system 53 through the communication network 56, and the update process comes to an end.

However, when response information is transmitted at step S334, S338, or S339, the communication unit 91 of the service A client system 53 receives the response information transmitted from the service A auxiliary system 55 and supplies the response information to the control unit 93 at step S304.

At step S305, the control unit 93 supplies the response information supplied thereto from the communication unit 91 to the display unit 96 so as to be displayed, and the update request process comes to an end.

By this process, the response information that the service cannot be utilized, the response information that update is completed or the response information that update is not performed is displayed on the display unit 96.

In the service provision system, the other-service IC card 52 can be utilized to update the service utilization additional information in the service A auxiliary system 55 to the latest service utilization additional information in such a manner as described above. Consequently, a service can be provided more appropriately to the user.

It is to be noted that, in the case where the service utilization additional information difference information is updated to the latest service utilization additional information difference information in the service A auxiliary system 55, for example, at step S301, input information from which at least service utilization additional information difference information can be obtained is acquired, and this input information is transmitted at step S303. Then, in the service A auxiliary system 55, processes similar to those in the case where the service utilization additional information is updated are performed to update the service utilization additional information difference information.

Now, a process by which service utilization additional information is updated as occasion demands in the case where the user uses the service A IC card 51 to utilize a service is described.

In particular, a service utilization process by the service A client system 53 and a service provision auxiliary process by the service A auxiliary system 55 are described.

First, the service utilization process by the service A client system 53 is described with reference to a flow chart of FIG. 16.

In the case where the user is to use the service A IC card 51 to utilize a service, the user would go to a pharmacy or the like and hold the service A IC card 51 possessed thereby over the IC card reader 61.

Consequently, at step S371, the IC card reader 61 acquires a standard ID, authentication information, service utilization additional information, and update date and time from the service A IC card 51 and supplies them to the read-write controlling unit 92 under the control of the read-write controlling unit 92.

The read-write controlling unit 92 supplies the standard ID, the authentication information, the service utilization additional information, and the update date and time supplied from the IC card reader 61 to the communication unit 91 through the control unit 93.

At step S372, the communication unit 91 transmits the standard ID, the authentication information, the service utilization additional information, and the update date and time to the service A auxiliary system 55 through the communication network 56.

After the standard ID, the authentication information, the service utilization additional information, and the update date and time are transmitted in this manner, the service A auxiliary system 55 performs an authentication process and decides whether or not there is the necessity to update the service utilization additional information.

For example, in the case where an authentication process is performed and the authentication results in success, the user can utilize the service. In contrast, in the case where the authentication results in failure, response information that the service cannot be utilized is transmitted from the service A auxiliary system 55.

At step S373, the control unit 93 decides whether or not the service can be utilized. For example, in the case where response information that the service cannot be utilized is transmitted from the service A auxiliary system 55, the control unit 93 decides that the service cannot be utilized.

In the case where it is decided at step S373 that the service can be utilized, the client apparatus 62 executes a process for receiving provision of a service at step S374. It is to be noted that, since the process at step S374 is similar to the process at step S84 of FIG. 8, description of it is omitted.

At step S375, the control unit 93 decides whether or not an update request is transmitted thereto. This update request is transmitted together with the latest service utilization additional information from the service A auxiliary system 55 when it is decided in the service A auxiliary system 55 that the service utilization additional information recorded in the service A IC card 51 is not the latest service utilization additional information.

In the case where it is decided at step S375 that an update request is not transmitted, the service utilization additional information in the service A IC card 51 is the latest service utilization additional information and there is no necessity to update, the processes at steps S376 and S377 are skipped and the service utilization process comes to an end.

In contrast, in the case where it is decided at step S375 that an update request is transmitted, the communication unit 91 receives the update request and the latest service utilization additional information transmitted from the service A auxiliary system 55 and supplies them to the control unit 93 at step S376.

Further, in response to the update request, the control unit 93 supplies the latest service utilization additional information received at step S376 to the read-write controlling unit 92 and instructs the read-write controlling unit 92 to write the latest service utilization additional information into the service A IC card 51.

It is to be noted that whether or not the latest service utilization additional information is to be written into the service A IC card 51, in short, whether or not the service utilization additional information is to be updated, may be determined finally by an input instruction by the user, a pharmacist or the like. Alternatively, only an update portion of the service utilization additional information may be received from the service A auxiliary system 55.

At step S377, the read-write controlling unit 92 updates the service utilization additional information in the service A IC card 51 on the basis of the service utilization additional information supplied from the control unit 93, and the service utilization process comes to an end.

In particular, the read-write controlling unit 92 supplies the service utilization additional information to the IC card reader 61 such that the service utilization additional information in the service A IC card 51 is updated and the update date and time associated with the service utilization additional information is updated to the current date and time.

On the other hand, in the case where it is decided at step S373 that the service cannot be utilized, processes at steps S378 and S379 are performed, and the service utilization process comes to an end. However, since the processes are similar to the processes at steps S85 and S86 of FIG. 8, description of them is omitted.

The service A client system 53 updates the service utilization additional information in the service A IC card 51 in accordance with an update request in such a manner as described above. Consequently, it is made possible to use the latest service utilization additional information, and as a result, a service can be provided more appropriately to the user.

Now, the service provision auxiliary process by the service A auxiliary system 55 is described with reference to a flow chart of FIG. 17. This service provision auxiliary process is executed when the service utilization process described hereinabove with reference to FIG. 16 is performed by the service A client system 53.

Figure 16:
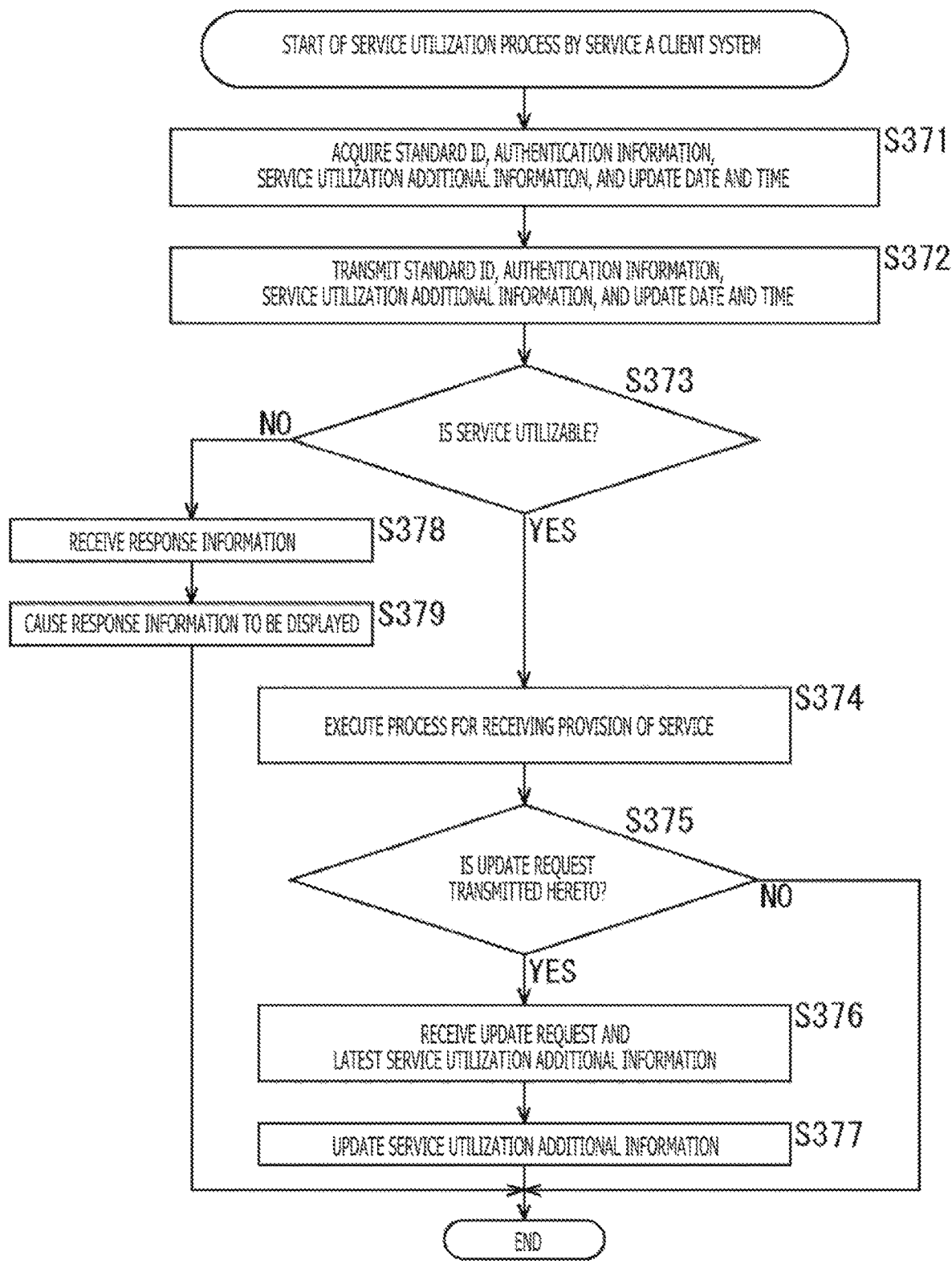
FIG. 16 is a flow chart illustrating a service utilization process.
Figure 17:
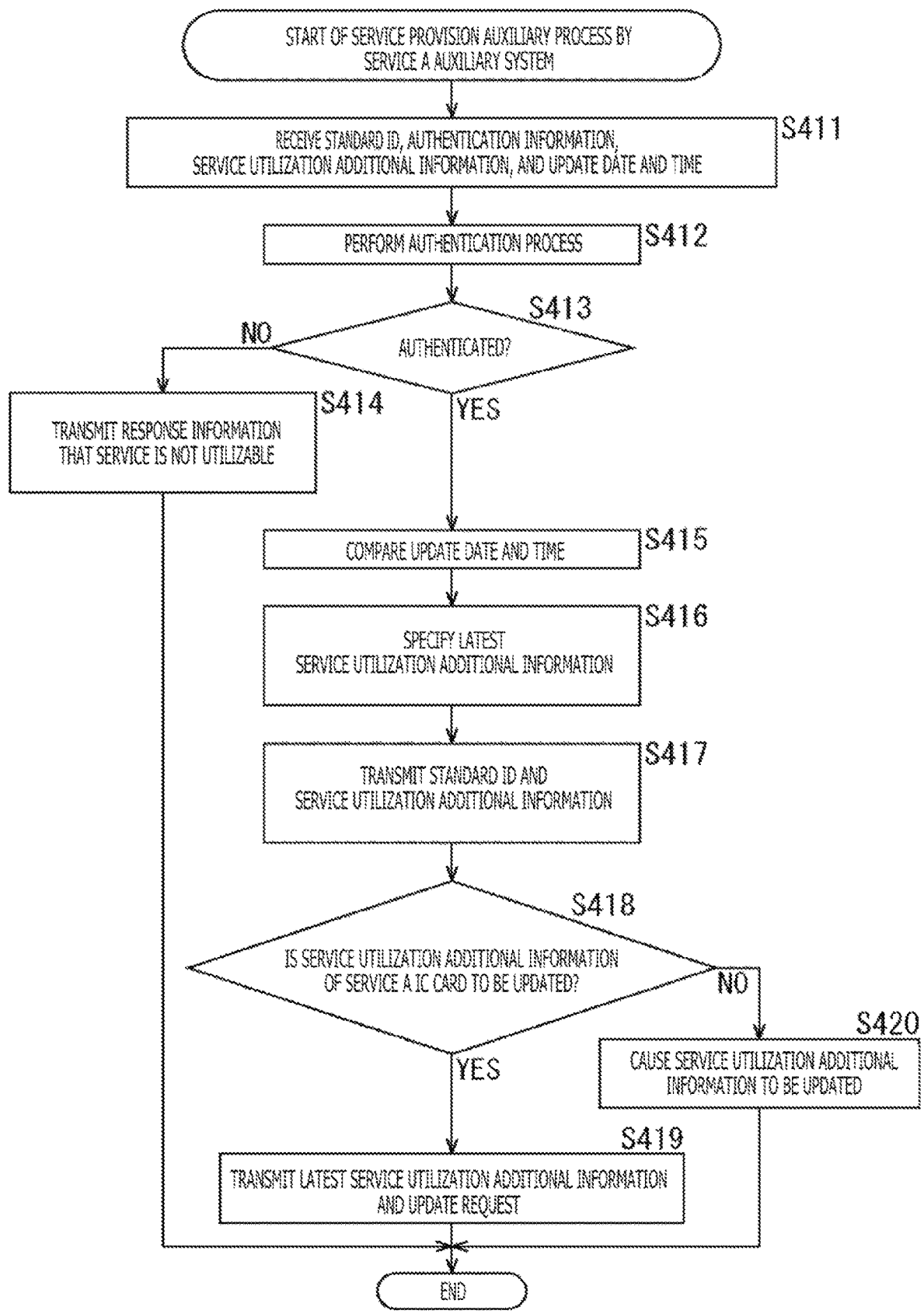
FIG. 17 is a flow chart illustrating a service provision auxiliary process.

At step S411, the communication unit 161 receives the standard ID, the authentication information, the service utilization additional information, and the update date and time transmitted from the service A client system 53 by the process at step S372 of FIG. 16 and supplies them to the control unit 162.

Thereafter, processes at steps S412 to S414 are executed. However, since the processes are similar to the processes at steps S22 to S24 of FIG. 7, description of them is omitted.

On the other hand, if it is decided at step S413 that the authentication results in success, the table management unit 172 compares the update date and time of the service utilization additional information at step S415.

In particular, the table management unit 172 reads out service utilization additional information and update date and time recorded in the ID correspondence table of the recording unit 163 in an associated relationship with the standard ID received at step S411 and compares the update date and time with the update date and time received at step S411.

At step S416, the table management unit 172 specifies the latest service utilization additional information from a result of the comparison of the update date and time. In this case, the service utilization additional information whose update date and time is newer, namely, is nearer to the current date and time, is determined as the latest service utilization additional information.

The control unit 162 supplies the latest service utilization additional information and the standard ID received at step S411 to the communication unit 161.

At step S417, the communication unit 161 transmits the standard ID and the service utilization additional information supplied from the control unit 162 to the service A cloud server 54 through the communication network 56. Further, the control unit 162 controls the communication unit 161 to instruct the service A cloud server 54 to access the service A client system 53, namely, to provide a service. Consequently, the service A cloud server 54 performs a process similar to the service provision process described hereinabove with reference to FIG. 9 and a service is provided to the user or the like.

At step S418, the table management unit 172 decides whether or not the service utilization additional information in the service A IC card 51 is to be updated. For example, in the case where it is decided at step S416 that the service utilization additional information recorded in the ID correspondence table of the recording unit 163 is the latest service utilization additional information, it is decided at step S418 that the service utilization additional information in the service A IC card 51 is to be updated.

In the case where it is decided at step S418 that the service utilization additional information in the service A IC card 51 is to be updated, the table management unit 172 supplies the latest service utilization additional information and an update request for requesting update of the service utilization additional information to the communication unit 161, and the processing advances to step S419.

The table management unit 172 causes the communication unit 161 to transmit the latest service utilization additional information and the update request to the service A client system 53 to control update to the latest service utilization additional information in the service A IC card 51 that is an acquisition source of the standard ID or the service utilization additional information received at step S411.

At step S419, the communication unit 161 transmits the latest service utilization additional information and the update request supplied from the table management unit 172 to the service A client system 53 through the communication network 56, and the service provision auxiliary process comes to an end. In this case, in the service utilization process described hereinabove with reference to FIG. 16, processes at steps S376 and S377 are performed.

It is to be noted that, while an example in which the latest service utilization additional information is transmitted together with the update request is described here, only an update portion for updating to the latest service utilization additional information may otherwise be transmitted.

On the other hand, in the case where it is decided at step S418 that the service utilization additional information in the service A IC card 51 is not to be updated, the processing advances to step S420.

At step S420, the table management unit 172 supplies the latest service utilization additional information received at step S411 to the recording unit 163 such that the service utilization additional information recorded in an associated relationship with the standard ID in the ID correspondence table is updated. Further, at this time, the table management unit 172 causes also the update date and time associated with the standard ID to be updated to the current date and time.

It is to be noted that, when both the service utilization additional information in the service A auxiliary system 55 and the service utilization additional information in the service A IC card 51 are the latest service utilization additional information, update of the service utilization additional information is not performed.

After the service utilization additional information in the recording unit 163 is updated in this manner, the service provision auxiliary process comes to an end.

The service A auxiliary system 55 specifies which one of the service utilization additional information in the service A auxiliary system 55 and the service utilization additional information in the service A IC card 51 is the latest service utilization additional information and updates the service utilization additional information as occasion demands in such a manner as described above.

Consequently, it can be made to use the latest service utilization additional information, and as a result, a service can be provided more appropriately to the user. Further, even in the case where the user or the like does not notice that the service utilization additional information in the service A IC card 51 is not the latest service utilization additional information, since the service utilization additional information is updated appropriately, the convenience can be improved further.

It is to be noted here that an example in which a standard ID or service utilization additional information is transmitted directly to the service A auxiliary system 55 at step S372 of FIG. 16 is described here. However, a standard ID or service utilization additional information may be transmitted to the service A cloud server 54 at step S372.

In such a case as just described, for example, an authentication process of the service A IC card 51 using authentication information or a process for providing the service A is performed by the service A cloud server 54. Further, a standard ID, service utilization additional information, update date and time and so forth are supplied from the service A cloud server 54 to the service A auxiliary system 55, and specification of the latest service utilization additional information, update of service utilization additional information and so forth are performed by the service A auxiliary system 55.

<Modification 3 to First Embodiment>
<Update of ID Correspondence Table>

Further, in the case where a driver's license of a vehicle is used as the other-service IC card 52, a license card number recorded on the driver's license is used as a nonstandard ID.

A driver's license has a nature that, in a state in which it is issued first, the lower one digit of its license number is 0, and every time the driver's license is reissued, the lower one digit of the license number is incremented by 1. Therefore, in the case where the license card is used as the other-service IC card 52, if it is made possible to receive, even when the other-service IC card 52 is reissued due to loss or the like and the license number that is a nonstandard ID changes, provision of a service on the basis of the reissued other-service IC card 52, then the convenience can be improved.

Therefore, in the present technology, it is made possible to use a reissued new driver's license as the other-service IC card 52 without the necessity for new registration or the like and it is made unable to use an old driver's license before the reissuance as the other-service IC card 52.

Figure 18:
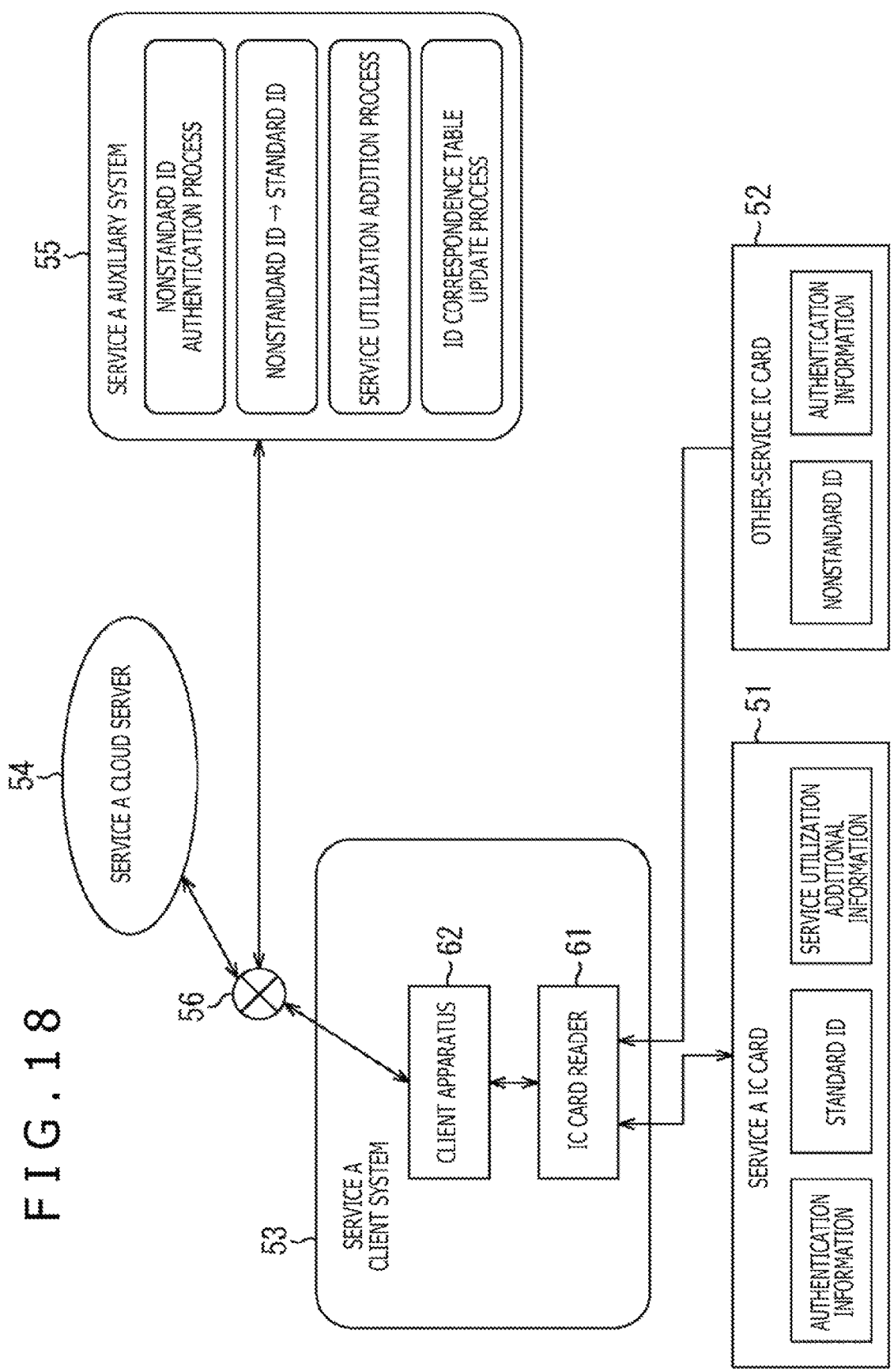
FIG. 18 is a view depicting an example of a configuration of a service provision system.

In such a case as just described, the service provision system is configured, for example, in such a manner as depicted in FIG. 18. It is to be noted that, in FIG. 18, portions corresponding to those in the case of FIG. 2 are denoted by the same reference characters, and description of the same is omitted suitably.

In this example, the service A auxiliary system 55 is additionally provided with a function for performing an update process of updating an ID correspondence table.

It is to be noted that, while the description here is given assuming that the other-service IC card 52 is a driver's license, if part of ID information used as the nonstandard ID like a driver's license irregularly changes in response to reissuance or the like, then the other-service IC card 52 may be any card.

The license number registered in a driver's license as the other-service IC card 52 is numerical value information of 12 digits, and every time the driver's license is reissued, the lower one digit of the driver's license is incremented by one.

Therefore, the service A auxiliary system 55 specifies the other-service IC card 52 is a registered one using the top 11 digits of the nonstandard ID and updates the ID correspondence table suitably in response to the lower one digit of the nonstandard ID.

<Update of ID Correspondence Table Upon Use of Other-Service IC Card>

Now, a process of the service provision system performed in such a case as described above is described.

In this case, in the service provision system, upon registration of the other-service IC card 52, a process similar to the process described hereinabove with reference to FIG. 7 is performed. However, in the case where hashing of a nonstandard ID is performed upon registration of the nonstandard ID, only the top 11 digits of the nonstandard ID are hashed. In particular, information including a hash value of the top 11 digits of the nonstandard ID and a value of the lower one digit of the nonstandard ID and the standard ID are registered in an associated relationship into the ID correspondence table.

Figure 19:
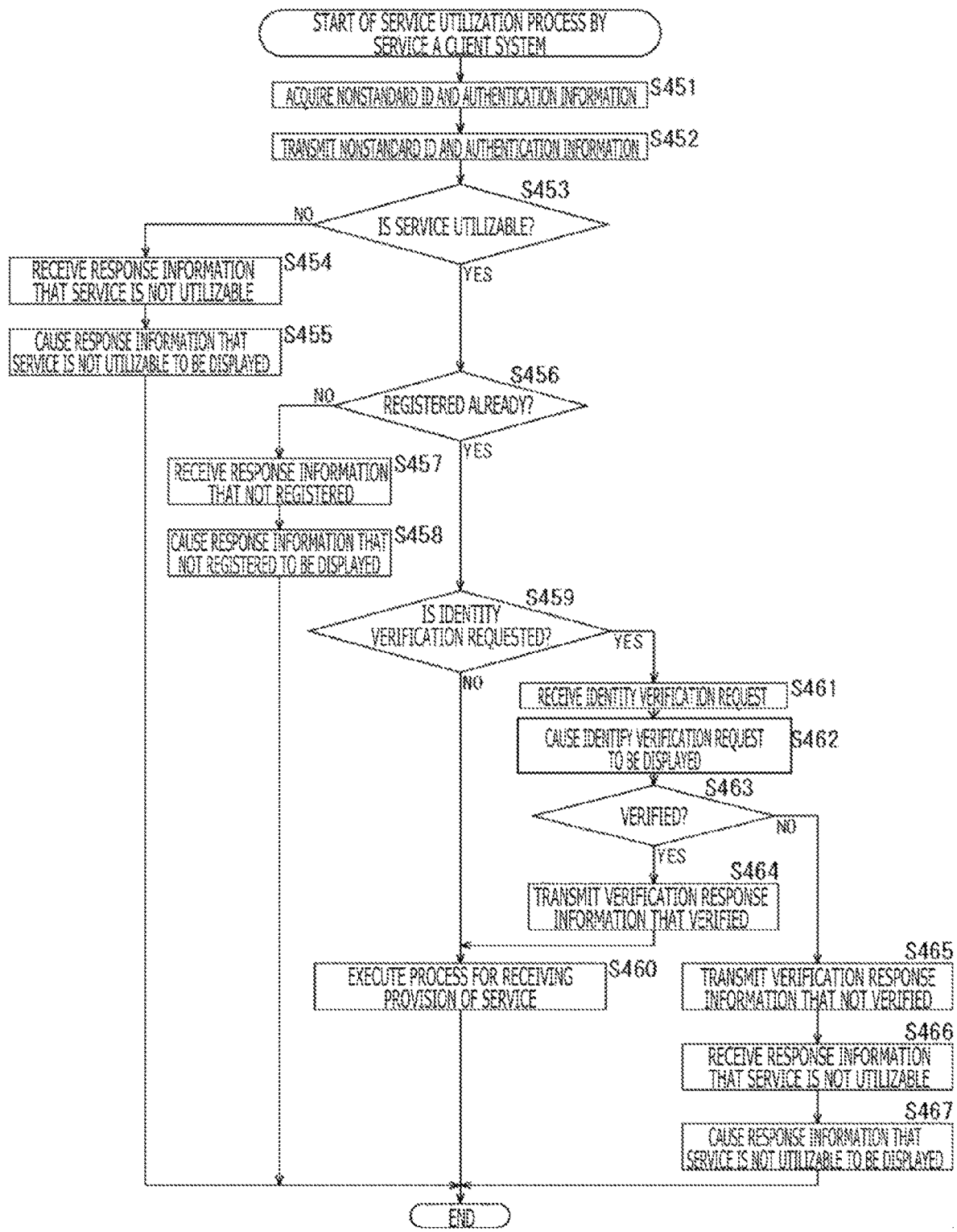
FIG. 19 is a flow chart illustrating a service utilization process.
Figure 20:
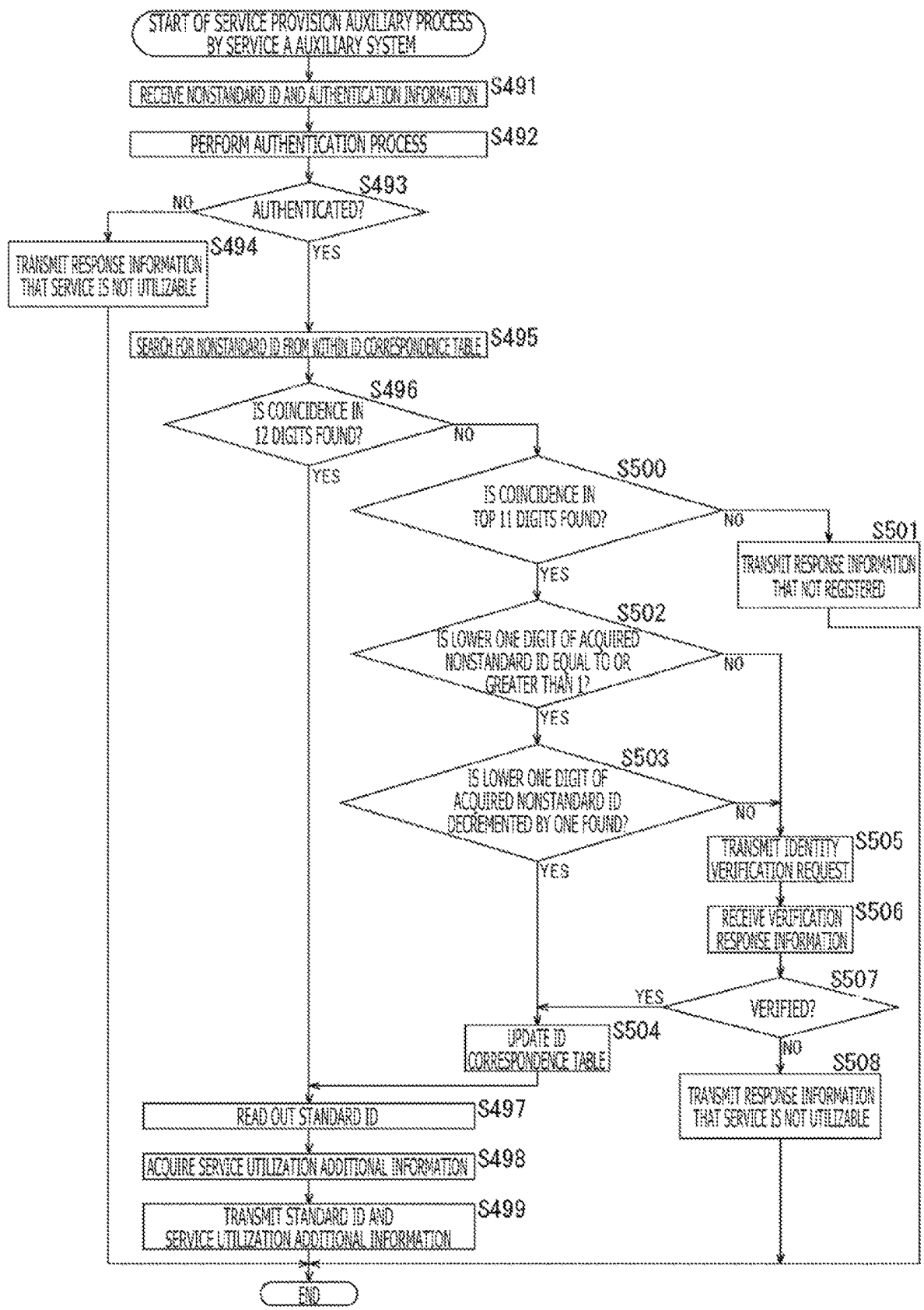
FIG. 20 is a flow chart illustrating a service provision auxiliary process.

Further, in the case where the user utilizes a service using the other-service IC card 52, processes depicted in FIGS. 19 and 20 are performed.

First, a service utilization process by the service A client system 53 is described with reference to a flow chart of FIG. 19. It is to be noted that, since processes at steps S451 to S453 are similar to the processes at steps S81 to S83 of FIG. 8 individually, description of them is omitted.

In the case where it is decided at step S453 that the service cannot be utilized, processes at steps S454 and S455 are executed thereafter and the service utilization process comes to an end. However, since the processes are similar to the processes at steps S85 and S86 of FIG. 8, description of them is omitted. In particular, in the processes, response information that the service cannot be utilized is received and displayed.

In contrast, in the case where it is decided at step S453 that the service can be utilized, the control unit 93 decides at step S456 whether or not the other-service IC card 52 is registered already.

For example, in the service A auxiliary system 55, if authentication of the other-service IC card 52 is performed, then a search is performed in regard to whether the nonstandard ID is registered in the ID correspondence table to specify whether the other-service IC card 52 is registered already. Then, in the case where the other-service IC card 52 is not registered as yet, response information that the other-service IC card 52 is not registered is transmitted from the service A auxiliary system 55.

Thus, in the case where the response information that the other-service IC card 52 is not registered is transmitted from the service A auxiliary system 55, the control unit 93 decides at step S456 that the other-service IC card 52 is not registered.

In the case where it is decided at step S456 that the other-service IC card 52 is not registered, the communication unit 91 receives, at step S457, the response information transmitted from the service A auxiliary system 55 and representing that the other-service IC card 52 is not registered and supplies the response information to the control unit 93.

At step S458, the control unit 93 supplies the response information supplied from the communication unit 91 and representing that the other-service IC card 52 is not registered to the display unit 96 such that the response information is displayed, and the service utilization process comes to an end.

On the other hand, in the case where it is decided at step S456 that the other-service IC card 52 is registered, the control unit 93 decides at step S459 whether or not identity verification is requested from the service A auxiliary system 55.

For example, in the service A auxiliary system 55, although a license number as the nonstandard ID whose top 11 digits coincide is found, in the case where the lower one digit does not coincide, since identity verification is suitably required upon update of the ID correspondence table, an identity verification request is sometimes transmitted to the service A auxiliary system 55. At step S459, in the case where such an identity verification request is transmitted to the service A auxiliary system 55, it is decided that identity verification is requested.

In the case where it is decided at step S459 that identity verification is not requested, the client apparatus 62 executes a process for receiving provision of a service at step S460, and the service utilization process comes to an end. It is to be noted that, at step S460, a process similar to that at step S84 of FIG. 8 is performed.

On the other hand, in the case where it is decided at step S459 that identity verification is requested, the communication unit 91 receives the identity verification request transmitted from the service A auxiliary system 55 and supplies it to the control unit 93 at step S461.

At step S462, the control unit 93 supplies the identify verification request supplied from the communication unit 91 to the display unit 96 so as to be displayed. When the identity verification request is displayed in this manner, an employee or the like of a pharmacy such as a pharmacist or the like who confirms the display would perform identity verification of the user through an identity card or the like and operate the inputting unit 94 to input a result of the verification.

At step S463, the control unit 93 decides on the basis of a signal supplied from the inputting unit 94 in response to the operation of the employee or the like whether or not it is verified that the user is the user itself.

In the case where it is decided at step S463 that it is verified that the user is the user itself, the control unit 93 generates and supplies confirmation response information that the user is verified to the communication unit 91, and the processing advances to step S464.

At step S464, the communication unit 91 transmits the confirmation response information supplied from the control unit 93 and representing that the user is verified to the service A auxiliary system 55 through the communication network 56.

Consequently, in the service A auxiliary system 55, the ID correspondence table is updated, and the user can thereafter receive provision of a service as usual. In particular, when the process at step S464 is performed, the processing thereafter advances to step S460, at which a process for receiving provision of a service is executed.

In contrast, in the case where it is decided at step S463 that the user is not verified, the control unit 93 generates and supplies confirmation response information that the user is not verified to the communication unit 91, whereafter the processing advances to step S465.

At step S465, the communication unit 91 transmits the confirmation response information supplied from the control unit 93 and representing that the user is not verified to the service A auxiliary system 55 through the communication network 56.

Consequently, since response information that the service cannot be utilized is transmitted from the service A auxiliary system 55, the communication unit 91 receives, at step S466, the response information transmitted from the service A auxiliary system 55 and representing that the service cannot be utilized and supplies the response information to the control unit 93.

At step S467, the control unit 93 supplies the response information supplied from the communication unit 91 and representing that the service cannot be utilized to the display unit 96 so as to be displayed, and the service utilization process comes to an end.

The service A client system 53 suitably performs identity verification and performs a process for receiving provision of a service in such a manner as described above. In this manner, in the service provision system, also when the other-service IC card 52 is reissued, the user can receive a service without particularly performing a cumbersome process such as re-registration or the like of the other-service IC card 52. Consequently, the convenience can be improved.

Now, the service provision auxiliary process by the service A auxiliary system 55 is described with reference to a flow chart of FIG. 20. This service provision auxiliary process is executed when the service utilization process described hereinabove with reference to FIG. 19 is performed by the service A client system 53.

It is to be noted that, since processes at steps S491 to S494 are similar to the processes at steps S111 to S114 of FIG. 9 individually, description of them is omitted.

In the case where it is decided at step S493 that the authentication results in success, the table management unit 172 searches, at step S495, for a nonstandard ID coincident with the nonstandard ID received at step S491 from among the nonstandard IDs registered in the ID correspondence table registered in the recording unit 163.

At step S496, the table management unit 172 decides whether or not the nonstandard IDs registered in the ID correspondence table include a nonstandard ID that coincides at all of the 12 digits thereof with the nonstandard ID received at step S491. In other words, it is decided whether or not there exists a nonstandard ID that indicates full coincidence.

In the case where it is decided at step S496 that there exists a nonstandard ID that indicates full coincidence at all of the 12 digits thereof, the table management unit 172 reads out a standard ID associated with the nonstandard ID from the ID correspondence table at step S497.

In this manner, in the case where a nonstandard ID coincides fully, the other-service IC card 52 is same as that as registered and is not subject to reissuance, a process for providing a service as usual is performed thereafter.

In particular, processes at steps S498 and S499 are performed, and the service provision auxiliary process comes to an end. Thereafter, the service A cloud server 54 performs a process similar to the service provision process described hereinabove with reference to FIG. 9. It is to be noted that, since the processes at steps S498 and S499 are similar to the processes at steps S116 and S117 of FIG. 9 individually, description of them is omitted.

In contrast, in the case where it is decided at step S496 that there does not exist a nonstandard ID that coincides at all of the 12 digits thereof, the table management unit 172 decides at step S500 whether or not the nonstandard IDs registered in the ID correspondence table include a nonstandard ID that coincides at the top 11 digits thereof with the nonstandard ID received at step S491. In other words, it is decided whether or not the nonstandard IDs registered in the ID correspondence table include a nonstandard ID that is different, although this is a registered nonstandard ID, at the lower one digit thereof because the driver's license has been reissued as the other-service IC card 52.

In the case where it is decided at step S500 that a nonstandard ID that coincides at the top 11 digits thereof does not exist, since the nonstandard ID is not registered in the ID correspondence table, namely, since the other-service IC card 52 is not a registered one, the control unit 162 generates response information that the other-service IC card 52 is not registered as yet. Then, the control unit 162 supplies the generated response information to the communication unit 161, and the processing advances to step S501.

At step S501, the communication unit 161 transmits the response information supplied from the control unit 162 and representing that the other-service IC card 52 is not registered as yet to the service A client system 53 through the communication network 56, and the service provision auxiliary process comes to an end. In this case, in the service utilization process of FIG. 19, the processes at steps S457 and S458 are performed.

On the other hand, in the case where it is decided at step S500 that a nonstandard ID that coincides at the top 11 digits thereof exists, the table management unit 172 decides at step S502 whether or not the lower one digit of the nonstandard ID received (acquired) at step S491 has a value equal to or higher than 1.

In the case where it is decided at step S502 that the lower one digit is not equal to or higher than 1, namely, that the lower one digit is 0, the processing advances to step S505. In this case, while the other-service IC card 52 that is to be used in order to receive provision of a service this time is one issued for the first time, the other-service IC card 52 registered in the service A auxiliary system 55 is a reissued one. Therefore, use of such an other-service IC card 52 as just described should not be permitted immediately, but such use should be permitted after identity verification is performed.

On the other hand, in the case where it is decided at step S502 that the lower one digit has a value equal to or higher than 1, the processing advances to step S503.

At step S503, the table management unit 172 decides whether or not the value of the lower one digit of the nonstandard ID in the ID correspondence table, which has been decided at step S500 that the top 11 digits coincide, is a value obtained by decrementing the lower one digit of the nonstandard ID received (acquired) at step S491 by 1.

In other words, it is decided whether or not the other-service IC card 52 to be used in order to receive provision of a service this time is a reissued one of the other-service IC card 52 registered in the service A auxiliary system 55.

For example, if the value of the lower one digit of the nonstandard ID received at step S491 is equal to a value obtained by incrementing the lower one digit of the nonstandard ID in the ID correspondence table by 2, then the other-service IC card 52 to be used this time is the registered other-service IC card 52 issued second time. Therefore, use of such an other-service IC card 52 as just described should not be permitted immediately, but the use should be permitted after identity verification is performed.

In contrast, if the value of the lower one digit of the nonstandard ID received at step S491 is equal to a value obtained by incrementing the lower one digit of the nonstandard ID in the ID correspondence table by 1, then the other-service IC card 52 to be used this time is a reissued one of the registered other-service IC card 52. In such a case as just described, if use of the reissued other-service IC card 52 is permitted and the original (old) other-service IC card 52 before the reissuance is disabled from use later, then the convenience can be improved while the security is assured.

In the case where it is decided at step S503 that the nonstandard ID has a lower one digit decremented by one, the table management unit 172 updates the ID correspondence table at step S504.

In particular, the table management unit 172 updates the ID correspondence table by replacing the nonstandard ID, which is registered in the ID correspondence table of the recording unit 163 and is decided at step S500 that the top 11 digits thereof coincide into the nonstandard ID received at step S491. In other words, the table management unit 172 updates the nonstandard ID registered in the ID correspondence table.

By this process, use of the other-service IC card 52 intended to be used this time is performed while the original other-service IC card 52 before the reissuance cannot be used any more.

After the ID correspondence table is updated, the processing advances to step S497, and processes at steps S497 to S499 are performed, whereafter the service provision auxiliary process comes to an end. In other words, a service is provided to the user or the like as usual.

In contrast, in the case where it is decided at step S503 that the nonstandard ID does not have a lower one digit decremented by one, the processing advances to step S505.

In the case where it is decided at step S502 that the lower one digit does not a value equal to or higher than 1 or it is decided at step S503 that the lower one digit does not have a value decremented by one, the communication unit 161 transmits an identity verification request at step S505.

In particular, the control unit 162 generates an identity verification request for requesting confirmation of whether the other-service IC card 52 to be used this time is that of the user itself and supplies the identity verification request to the communication unit 161. The communication unit 161 transmits the identity verification request supplied from the control unit 162 to the service A client system 53 through the communication network 56. In this case, in the service utilization process of FIG. 19, the processes at step S461 and the succeeding steps are performed.

Consequently, confirmation response information is transmitted from the service A client system 53 in response to the identity verification request.

At step S506, the communication unit 161 receives and supplies the confirmation response information transmitted from the service A client system 53 to the control unit 162.

At step S507, the control unit 162 decides whether or not the identity verification results in success on the basis of the confirmation response information supplied from the communication unit 161. Here, in the case where the received confirmation response information is confirmation response information representing that the identity verification results in success, it is decided that the identity verification results in success.

In the case where it is decided at step S507 that the identity verification results in success, the processing advances to step S504, and thereafter, the processes described hereinabove are performed and the service provision auxiliary process comes to an end. In particular, use of the other-service IC card 52 intended to be used this time is permitted, and use of the other-service IC card 52 registered upon registration is disabled.

In this manner, where the other-service IC card 52 or the like that is, although this is of the user itself, not a reissued one from an originally registered one, for example, an other-service IC card 52 issued for the second time or the like, by permitting use of the other-service IC card 52 after identity verification is performed, the convenience can be improved while the security is assured.

On the other hand, in the case where it is decided at step S507 that the identity verification results in failure, namely, in the case where the received confirmation response information is confirmation response information that the identity verification results in failure, the control unit 162 generates and supplies response information that the service cannot be utilized to the communication unit 161.

Then, at step S508, the communication unit 161 transmits the response information supplied from the control unit 162 and representing that the service cannot be utilized to the service A client system 53 through the communication network 56, and the service provision auxiliary process comes to an end. In this case, since the identity verification results in failure, in order to prevent any fraud, use of the other-service IC card 52 intended to be used this time is inhibited.

As described above, in the case where part of a nonstandard ID registered in the other-service IC card 52 that is an acquisition source of the nonstandard ID upon service utilization varies by reissuance, the service A auxiliary system 55 compares the acquired nonstandard ID and the nonstandard ID of the ID correspondence table and suitably updates the ID correspondence table. In particular, the top 11 digits of the nonstandard ID are used to specify whether the other-service IC card 52 is registered already, and the ID correspondence table is suitably updated in response to the lower one digit of the nonstandard ID. Consequently, the convenience can be improved while the security is assured.

Second Embodiment

<Example of Configuration of Service Provision System>

Incidentally, in recent years, various services on a web have become and are becoming utilized by users, and it is anticipated that this trend proceeds also in the future. By integrating information of a plurality of services, new and more convenient functions can be provided to users in the future.

It is a matter of course that, to this end, collaboration of services is required. However, there is the possibility that collaboration of services may be done in a state in which a user does not intend, and when collaboration is to be done, also such a contrivance as to avoid collaboration the user does not intend is demanded.

Therefore, in the present technology, different services in a service provision system are made collaborate with each other to improve the convenience and allow such collaboration to be done in accordance with an intention of its user.

Figure 21:
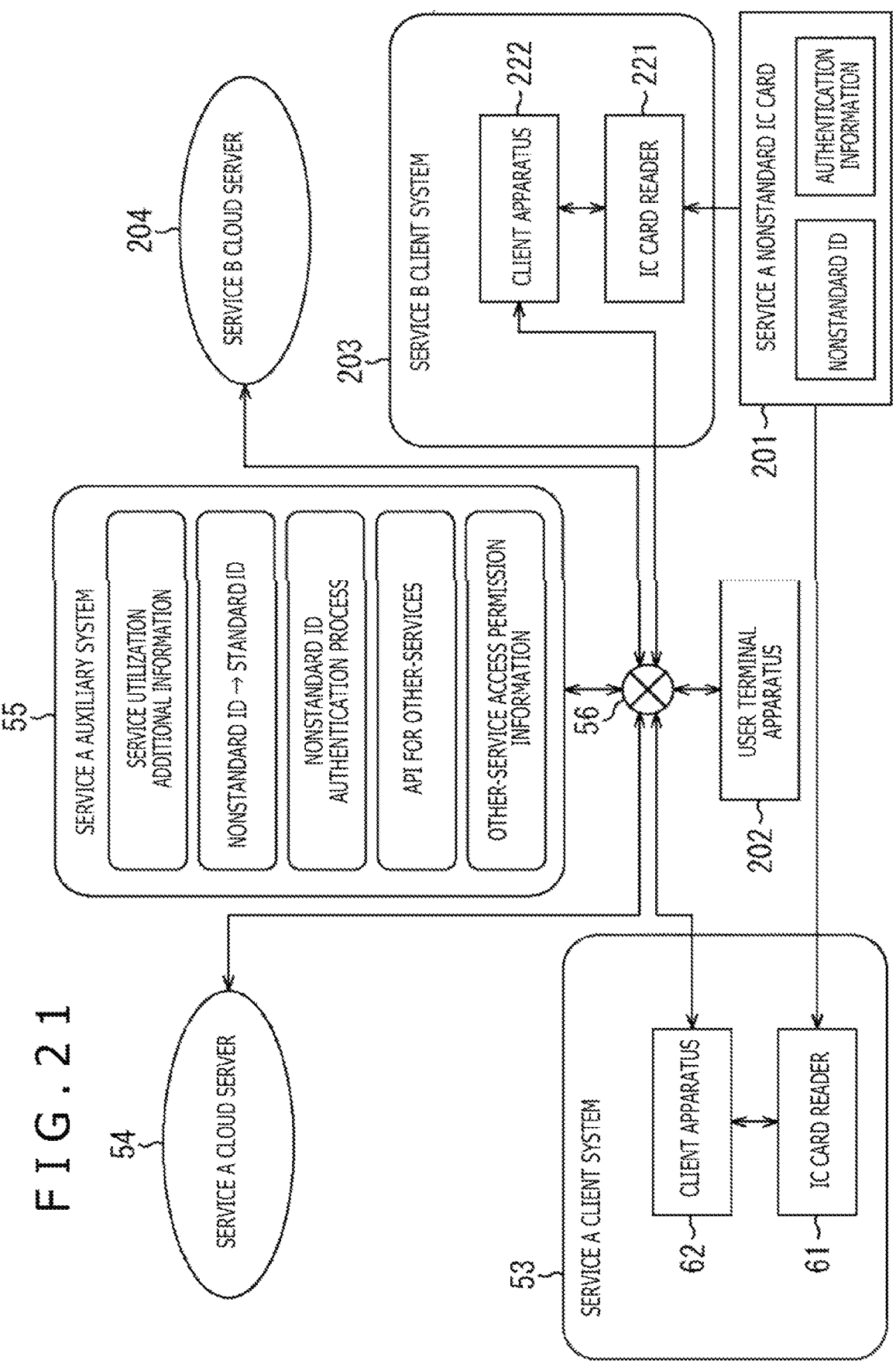
FIG. 21 is a view depicting an example of a configuration of a service provision system.

In such a case as just described, the service provision system is configured, for example, in such a manner as depicted in FIG. 21. It is to be noted that, in FIG. 21, portions corresponding to those in the case of FIG. 2 are denoted by the same reference characters, and description of the same is suitably omitted.

In the service provision system depicted in FIG. 21, the service A described hereinabove with reference to FIG. 2 and a service B different from the service A can be caused to collaborate with each other to provide a service to a user.

In the example of FIG. 21, the service provision system includes a service A nonstandard IC card 201, a user terminal apparatus 202, a service A client system 53, a service A cloud server 54, a service A auxiliary system 55, a service B client system 203, and a service B cloud server 204.

Further, in the service provision system, the user terminal apparatus 202, the service A client system 53, the service A cloud server 54, the service A auxiliary system 55, the service B client system 203, and the service B cloud server 204 are connected to each other through a communication network 56.

The service A nonstandard IC card 201 corresponds to the other-service IC card 52 depicted in FIG. 2 and is an IC card that is not for exclusive use for the service A. In the service A nonstandard IC card 201, at least a nonstandard ID and authentication information are recorded similarly to the other-service IC card 52.

It is to be noted that the service A nonstandard IC card 201 may be an IC card for exclusive use for the service B or may not be an IC card for exclusive use for the service B if it is in a state in which the service B can be utilized. For example, in the case where the service A nonstandard IC card 201 is an IC card for exclusive use for the service B, the nonstandard ID in the service A nonstandard IC card 201 functions as a standard ID for the service B.

The user terminal apparatus 202 is a terminal apparatus that is suitably operated by a user.

Meanwhile, the service B client system 203 includes an IC card reader 221 and a client apparatus 222 and is utilized when the service B is provided to a user. The IC card reader 221 and the client apparatus 222 correspond to the IC card reader 61 and the client apparatus 62, respectively.

The service B cloud server 204 provides the service B to a user, for example, on the basis of a nonstandard ID. Especially, in this example, the service B cloud server 204 performs service provision to a user while suitably collaborating with the service A cloud server 54.

In particular, for example, when the service B cloud server 204 performs provision of the service B, it suitably utilizes medication history information and so forth recorded in the service A cloud server 54.

Upon collaboration with the service A cloud server 54, the service B cloud server 204 requests the service A auxiliary system 55 to execute a process for providing the service A. As a contrivance for this, the service A auxiliary system 55 has an API (Application Programming Interface) for some other-service, in short, in the present example, for the service B, and a list of the same recorded therein.

Here, the API recorded in the service A auxiliary system 55 is a program for implementing (executing) a process for requesting execution of a process for providing the service A to the service A cloud server 54, for example, execution of a process such as extraction of information of a predetermined condition or the like. The API list for the service B is a list of APIs that execute processes permitted to the service B by the service A.

Further, the service A auxiliary system 55 has recorded therein other-service access permission information indicative of whether or not the user permits utilization of the service B, namely, utilization of the API by the service B cloud server 204, such that the service B cloud server 204 can utilize the API only in the case in which the user permits this. In other words, the other-service access permission information is information indicative of whether or not access to the service A, namely, to the service A cloud server 54, by the service B, namely, by the service B cloud server 204, is permitted.

Utilization setting of an API by this other-service access permission information, in short, setting of access permission to the service A, is performed, for example, by a user operating the user terminal apparatus 202. In particular, the user would operate the user terminal apparatus 202 to directly access the service A auxiliary system 55 through the communication network 56 or to access the service A auxiliary system 55 through the communication network 56 and the service A cloud server 54.

Then, the user would operate the user terminal apparatus 202 to input whether or not access to the service A, namely, utilization of the API, is to be permitted to the service B, and the user terminal apparatus 202 transmits a result of the input to the service A auxiliary system 55. The service A auxiliary system 55 generates and records other-service access permission information to the service B in response to the result of the input received from the user terminal apparatus 202.

By making it possible to set permission of access of each of services different from the service A, for each user, in short, for each standard ID, to the service A in this manner, it is possible for information, which is managed by the service A, to prevent from being supplied to some other-service while the user does not intend this. This can improve the security.

It is to be noted that, while it is described here that permission of access is set by the user terminal apparatus 202, setting may be performed otherwise by operating the service A client system 53. Alternatively, the user terminal apparatus 202 or the service A client system 53 may access some other server for exclusive use to perform setting such that a result of the setting is transmitted from the server for exclusive use to the service A auxiliary system 55.

Furthermore, similarly as in the example of FIG. 2, the service A auxiliary system 55 has a function for performing an authentication process of a nonstandard ID and an ID reading out process of a standard ID corresponding to the nonstandard ID and has also service utilization additional information recorded therein.

In the case where the user uses the service A nonstandard IC card 201 to receive provision of the service B, the service B client system 203 reads out the nonstandard ID and the authentication information from the service A nonstandard IC card 201 held over by the user and transmits them to the service B cloud server 204.

Consequently, the service B cloud server 204 transmits, in order to utilize an API for the service B by the service A, the nonstandard ID and the authentication information to the service A auxiliary system 55 so as to be authenticated. Then, in the case where the authentication results in success and access to the service A by the service B is permitted through the other-service access permission information, the service B cloud server 204 receives supply of an API list from the service A auxiliary system 55 and utilizes an API.

It is to be noted that, although an example is described here in which the service A auxiliary system 55 performs authentication of the service A nonstandard IC card 201, the authentication of the service A nonstandard IC card 201 may be performed by the service B cloud server 204 or may be performed by both the service A auxiliary system 55 and the service B cloud server 204.

By configuring the service A auxiliary system 55 to perform authentication of the service A nonstandard IC card 201 in this manner, the security can be improved. In other words, for example, the service A can be prevented from supplying medication history information or the like of a user in error in response to a false nonstandard ID.

As described above, according to the service provision system depicted in FIG. 21, it is possible to allow a plurality of services to collaborate with each other in secure and provide a new function, which is implemented by the service collaboration, to the user in safety.

It is to be noted that an example is described here in which, when a user utilizes the service B, the service B client system 203 and the service B cloud server 204 directly perform information transfer therebetween. However, without being limited to this example, a service B auxiliary system corresponding to the service A auxiliary system 55 may be provided similarly as in the case of the service A.

<Example of Configuration of Client Apparatus>

Now, an example of a more detailed configuration of the client apparatus 222, the service B cloud server 204, and the service A auxiliary system 55 is described.

First, the client apparatus 222 is described.

Figure 22:
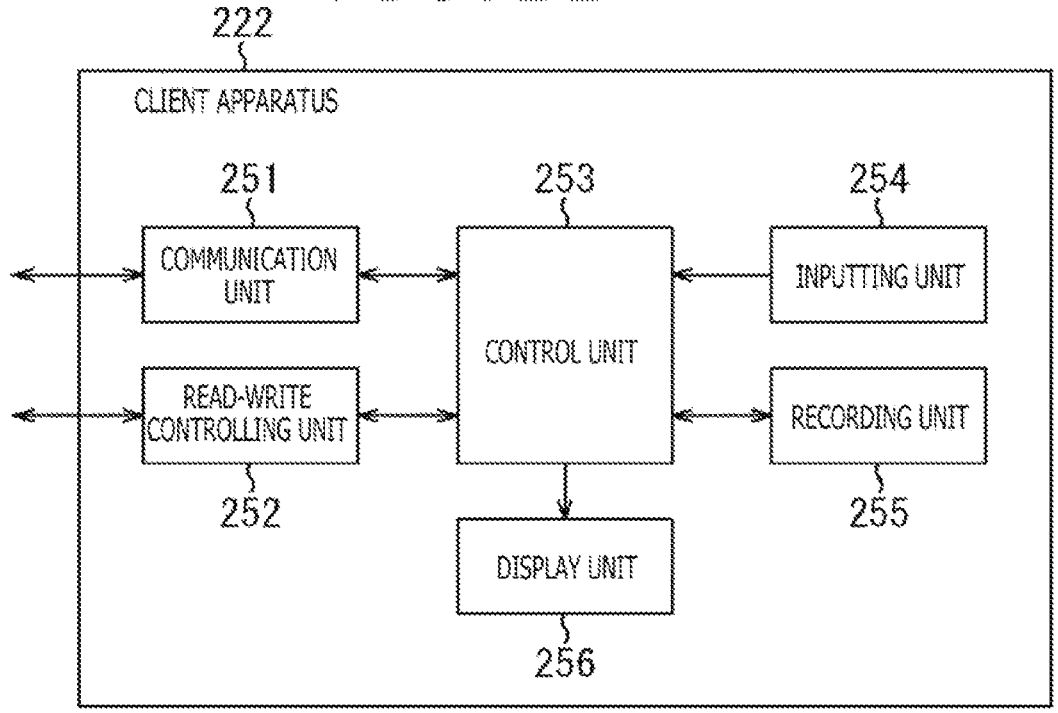
FIG. 22 is a view depicting an example of a configuration of a client apparatus.

FIG. 22 is a view depicting an example of a more detailed configuration of the client apparatus 222. It is to be noted that, while the client apparatus 222 here is a single apparatus, the client apparatus 222 may otherwise be configured from a plurality of apparatus.

The client apparatus 222 depicted in FIG. 22 includes a communication unit 251, a read-write controlling unit 252, a control unit 253, an inputting unit 254, a recording unit 255, and a display unit 256.

It is to be noted that, since the communication unit 251 to the display unit 256 are similar to the communication unit 91 to the display unit 96 of the client apparatus 62 individually, description of them is omitted.

<Example of Configuration of Service B Cloud Server>

Figure 23:
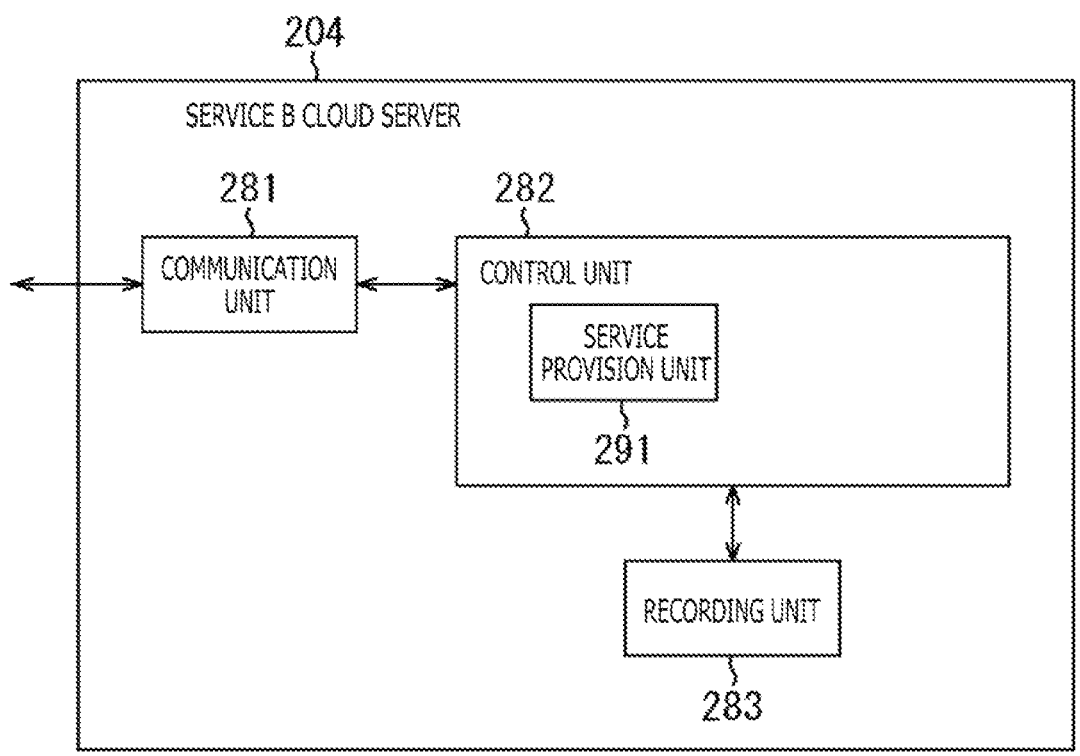
FIG. 23 is a view depicting an example of a configuration of a service B cloud server.

Meanwhile, the service B cloud server 204 is configured, for example, in such a manner as depicted in FIG. 23.

The service B cloud server 204 includes a communication unit 281, a control unit 282, and a recording unit 283. It is to be noted that, since the communication unit 281 to the recording unit 283 are similar to the communication unit 121 to the recording unit 123 of the service A cloud server 54 individually, description of them is suitably omitted.

The control unit 282 includes a service provision unit 291 similar to the service provision unit 131 provided in the control unit 122 of the service A cloud server 54.

Further, for example, in the recording unit 283, information relating to a user, which is required for provision of the service B, and so forth are recorded in an associated relationship with a nonstandard ID for each user.

<Example of Configuration of Service a Auxiliary System>

Figure 24:
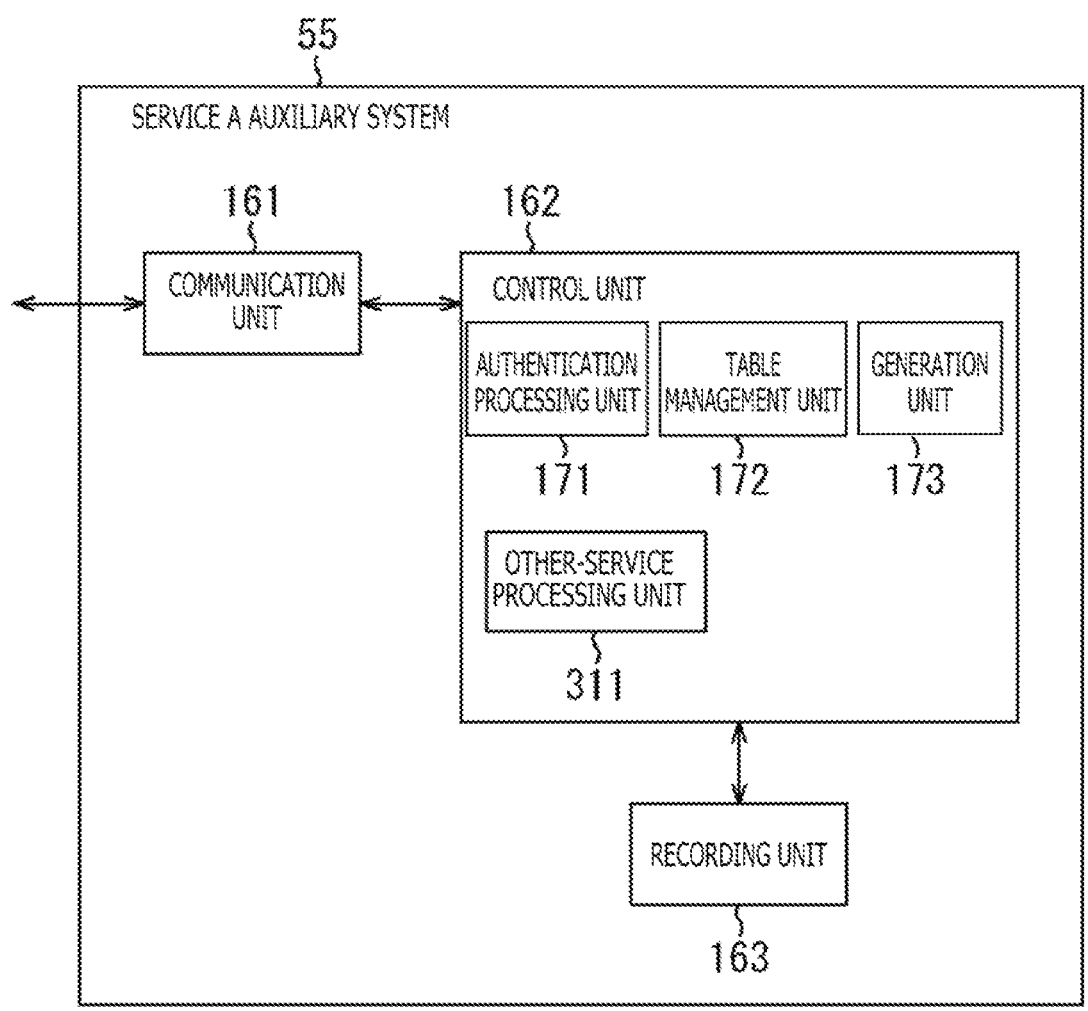
FIG. 24 is a view depicting an example of a configuration of a service A auxiliary system.

Further, the service A auxiliary system 55 depicted in FIG. 21 is configured, for example, in such a manner as depicted in FIG. 24. It is to be noted that, in FIG. 24, portions corresponding to those in the case in FIG. 5 are denoted by the same reference characters, and description of the same is omitted.

The service A auxiliary system 55 depicted in FIG. 24 includes a communication unit 161, a control unit 162, and a recording unit 163.

Further, the control unit 162 includes an other-service processing unit 311 in addition to an authentication processing unit 171, a table management unit 172, and a generation unit 173. The other-service processing unit 311 performs a process relating to access of a service different from the service A to the service A.

Figure 25:
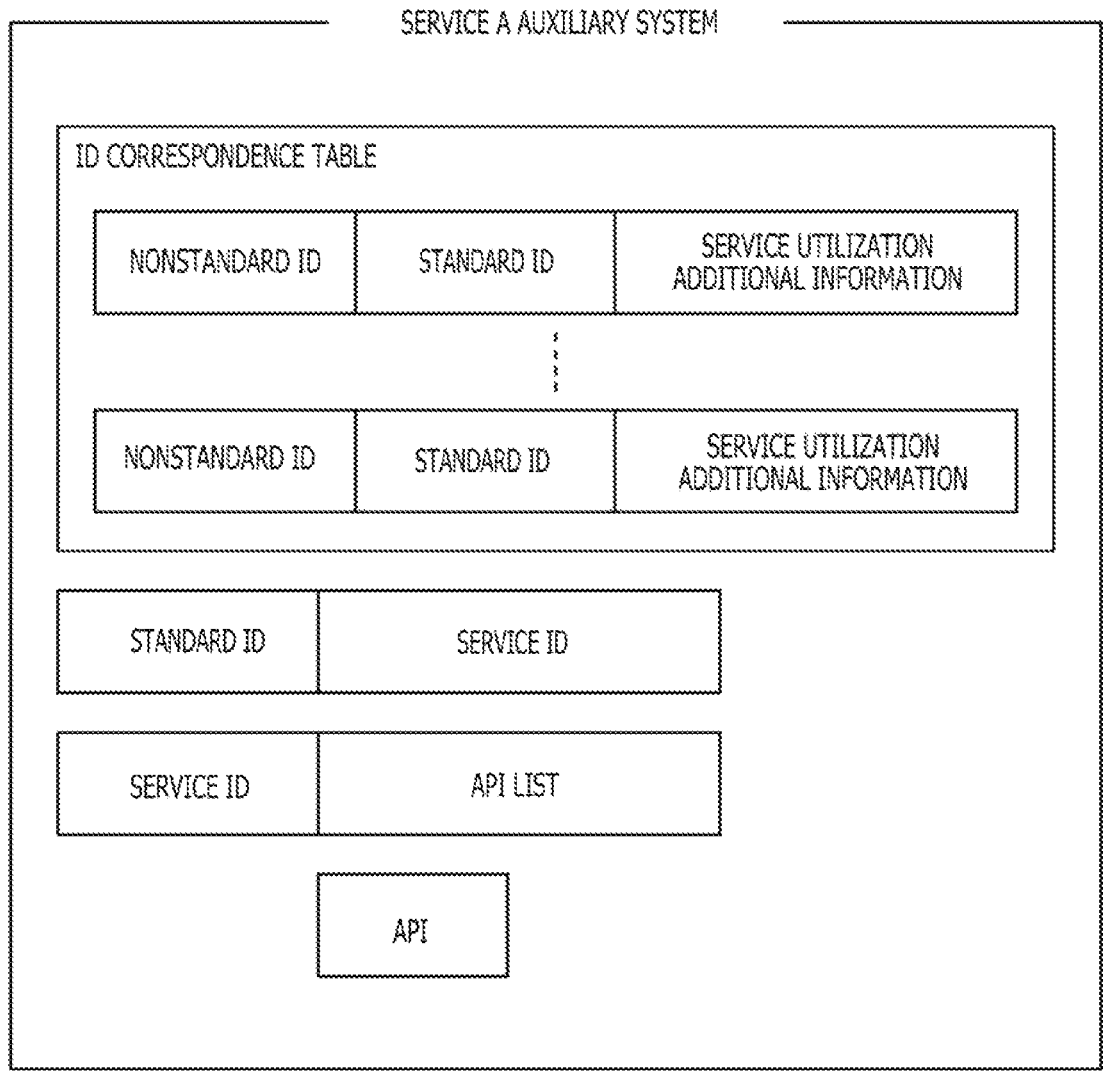
FIG. 25 is a view illustrating information managed by the service A auxiliary system.

Furthermore, in the recording unit 163, various kinds of information such as an ID correspondence table are recorded, for example, as depicted in FIG. 25.

In this example, an ID correspondence table is recorded similarly as in the example depicted in FIG. 6. Further, in the example depicted in FIG. 25, a standard ID and a service ID are recorded in an associated relationship with each other and a service ID and an API list are recorded in an associated relationship with each other.

Here, the service ID is information indicative of each service such as, for example, the service B, and other-service access permission information is configured from a standard ID and a service ID associated with each other. In this example, where a standard ID and a service ID are recorded in an associated relationship with each other, it is indicated that, as regards a user specified by the standard ID, a service indicated by the service ID is permitted to access the service A.

It is to be noted that, while, as information for specifying a user, a standard ID is associated with a service ID here, otherwise a nonstandard ID and a service ID may be recorded in an associated relationship with each other.

Further, also information indicative of whether or not access is permitted by a user may be recorded in an associated relationship with a standard ID and a service ID. Furthermore, the other-service access permission information may be any information if it indicates access permission of another service to the service A.

Furthermore, in the example depicted in FIG. 25, an API list is recorded in an associated relationship with a service ID in the recording unit 163. This API list is list information indicative of a list of APIs permitted by the service A to services specified by service IDs. Further, in the recording unit 163, also an API for requesting execution of a predetermined process for providing the service A, which can be executed by the service A auxiliary system 55 is recorded.

It is to be noted that, while description here is given of an example in which, upon provision of the service A, also service utilization additional information is utilized, the service utilization additional information need not necessarily be utilized.

<Process Upon Service Provision Utilizing Service Collaboration>

Subsequently, operation of the service provision system depicted in FIG. 21 is described.

First, the service A nonstandard IC card 201 is registered into the service A auxiliary system 55 similarly as in the first embodiment described hereinabove. In particular, the process described hereinabove with reference to FIG. 7 is performed for the service A nonstandard IC card 201 to record the ID correspondence table of the service A nonstandard IC card 201 into the service A auxiliary system 55.

Further, if the user operates the user terminal apparatus 202 to permit access of the service B to the service A upon utilization of the service B using the service A nonstandard IC card 201, then a service ID indicative of the service B and the standard ID of the user are recorded in an associated relationship as other-service access permission information into the service A auxiliary system 55.

Furthermore, in the service A auxiliary system 55, a service ID indicative of the service B and a list of APIs permitted to the service B are recorded in an associated relationship by registration in advance of the service B.

If such a state as just described is entered, then it becomes possible for the user to use the service A nonstandard IC card 201 to receive provision of the service B collaborating with the service A. In the following, a process of the service provision system performed in such a case as just described is described.

First, a service utilization process by the service B client system 203 is described with reference to a flow chart of FIG. 26.

In the case where the user intends to receive provision of the service B using the service A nonstandard IC card 201, the user would hold the service A nonstandard IC card 201 over the IC card reader 221 of the service B client system 203.

Consequently, at step S531, the IC card reader 221 acquires the nonstandard ID and the authentication information from the service A nonstandard IC card 201 and supplies them to the read-write controlling unit 252 under the control of the read-write controlling unit 252.

The read-write controlling unit 252 supplies the nonstandard ID and the authentication information supplied from the IC card reader 221 to the communication unit 251 through the control unit 253.

At step S532, the communication unit 251 transmits the nonstandard ID and the authentication information to the service B cloud server 204 through the communication network 56.

Consequently, the service B cloud server 204 transmits the nonstandard ID and the authentication information to the service A auxiliary system 55 so as to be authenticated.

At this time, in the case where the service A nonstandard IC card 201 is not authenticated, or in the case where the nonstandard ID is not registered in the ID correspondence table, response information that a service cannot be utilized is transmitted from the service A auxiliary system 55 through the service B cloud server 204.

On the other hand, also in the case in which authentication or the like results in success, in the case where access of the service B to the service A is not permitted by the other-service access permission information, response information that access is not permitted is transmitted from the service A auxiliary system 55 through the service B cloud server 204.

At step S533, the control unit 253 decides whether or not the service A nonstandard IC card 201 is a usable card. For example, in the case where response information that the service cannot be utilized is transmitted from the service B cloud server 204, it is decided that the service A nonstandard IC card 201 is not a usable card.

In the case where it is decided at step S533 that the service A nonstandard IC card 201 is not a usable card, the communication unit 251 receives, at step S534, the response information transmitted from the service B cloud server 204 through the communication network 56 and representing that the service cannot be utilized and supplies the response information to the control unit 253.

At step S535, the control unit 253 supplies the response information supplied from the communication unit 251 and representing that a service cannot be utilized to the display unit 256 so as to be displayed, and the service utilization process comes to an end.

On the other hand, in the case where it is decided at step S533 that the service A nonstandard IC card 201 is a usable card, the control unit 253 decides at step S536 whether or not access of the service B to the service A is permitted. For example, in the case where response information that the access is not permitted is transmitted from the service B cloud server 204, it is decided that the access is not permitted.

In the case where it is decided at step S536 that the access is not permitted, the communication unit 251 receives, at step S537, response information transmitted from the service B cloud server 204 through the communication network 56 and representing that the access is not permitted and supplies the response information to the control unit 253.

At step S538, the control unit 253 supplies the response information supplied from the communication unit 251 and representing that the access is not permitted to the display unit 256 so as to be displayed, and the service utilization process comes to an end.

On the other hand, in the case where the service A nonstandard IC card 201 is decided as a usable card and besides also access to the access of the service B to the service A is permitted, in short, in the case where it is decided at step S536 that the access is permitted, the processing advances to step S539. In this case, the service B is provided to the user by the service B cloud server 204.

At step S539, the client apparatus 222 executes a process for receiving provision of the service, and the service utilization process comes to an end.

In particular, for example, the communication unit 251 receives display data for information display for providing the service B, transmitted from the service B cloud server 204, and supplies the display data to the control unit 253, and the control unit 253 supplies the display data to the display unit 256 such that the display unit 256 displays the information.

The service B client system 203 acquires the nonstandard ID and the authentication information from the service A nonstandard IC card 201 and transmits them to the service B cloud server 204 in such a manner as described above. Consequently, the user can receive provision of the service B collaborating with the service A and the convenience can be improved.

Figure 26:
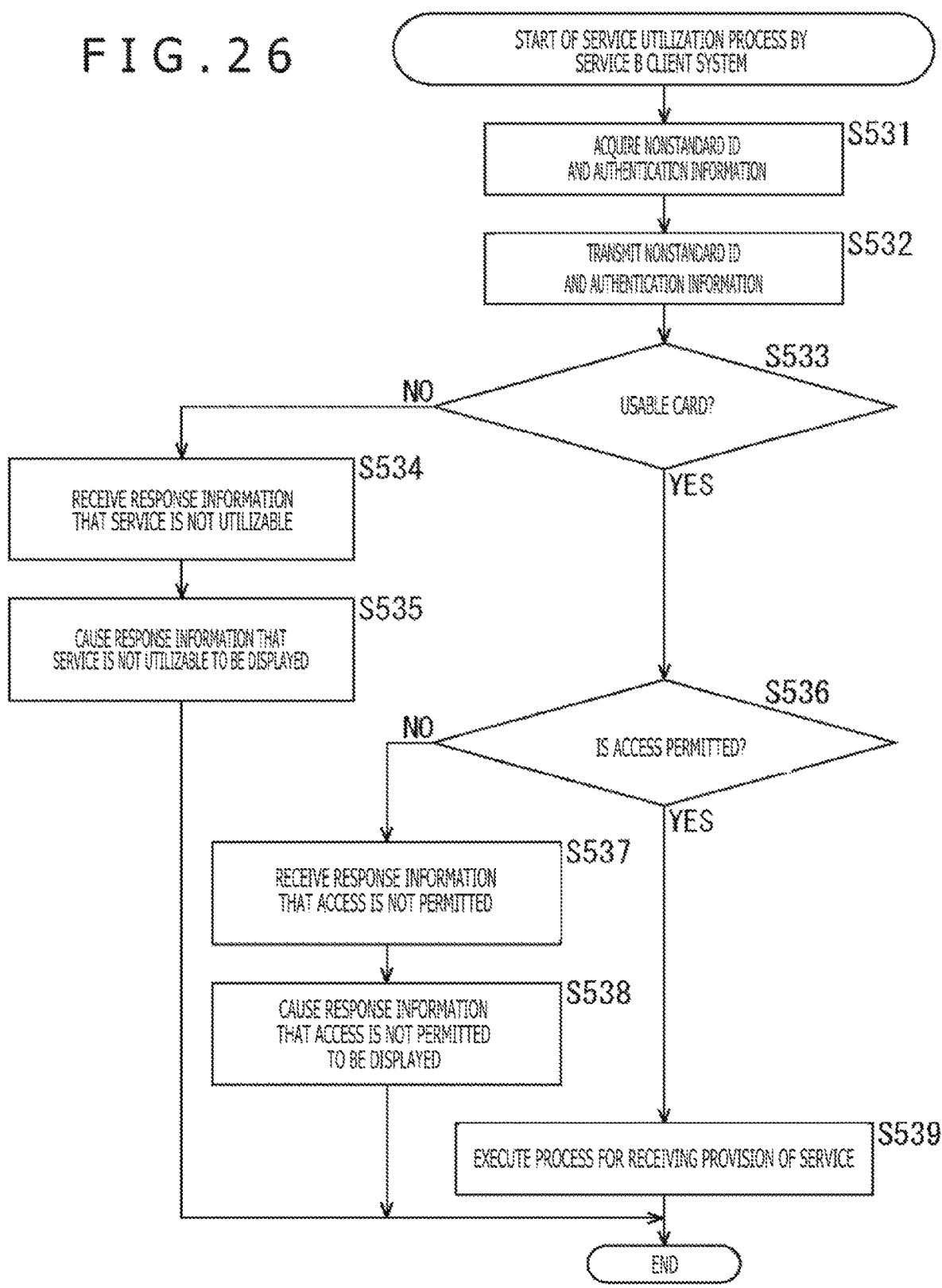
FIG. 26 is a flow chart illustrating a service utilization process.

Subsequently, a process that is performed by the service B cloud server 204 when the service utilization process described hereinabove with reference to FIG. 26 is performed is described. In particular, the service provision process by the service B cloud server 204 is described below with reference to a flow chart of FIG. 27.

If a nonstandard ID and authentication information are transmitted from the service B client system 203 by the process at step S532 of FIG. 26, then the communication unit 281 receives the nonstandard ID and the authentication information transmitted thereto and supplies them to the control unit 282 at step S571.

Further, at this time, the control unit 282 authenticates the service A nonstandard IC card 201 on the basis of the authentication information as occasion demands.

At step S572, the control unit 282 decodes the service ID recorded in the recording unit 283.

For example, in the recording unit 283, a service ID acquired from the service A auxiliary system 55 in advance and indicative of the service B and a public key are recorded, and the service ID is in a form encrypted with a secret key by the service A auxiliary system 55. In short, the service ID encrypted with the secrete key is recorded as a certificate of the service B in the recording unit 283.

The control unit 282 acquires the encrypted service ID recorded in the recording unit 283 in this manner and the public key and decrypts the service ID with the acquired public key. The control unit 282 supplies the service ID obtained by the decryption and the nonstandard ID and the authentication information received at step S571 to the communication unit 281.

At step S573, the communication unit 281 transmits the nonstandard ID, the authentication information, and the service ID supplied from the control unit 282 to the service A auxiliary system 55 through the communication network 56. It is to be noted that the nonstandard ID and so forth may otherwise be transmitted to the service A auxiliary system 55 through the service A cloud server 54.

After the nonstandard ID, the authentication information, and the service ID are transmitted to the service A auxiliary system 55, the service A auxiliary system 55 performs authentication or confirmation of access permission as described above and transmits response information.

At step S574, the control unit 282 decides whether or not the service A nonstandard IC card 201 is a usable card. For example, in the case where response information that a service cannot be utilized is transmitted from the service A auxiliary system 55, it is decided that the service A nonstandard IC card 201 is not a usable card.

In the case where it is decided at step S574 that the service A nonstandard IC card 201 is not a usable card, the communication unit 281 receives, at step S575, the response information transmitted from the service A auxiliary system 55 through the communication network 56 and representing that a service cannot be utilized and supplies the response information to the control unit 282. Then, the control unit 282 that receives the supply of the response information supplies the response information to the communication unit 281.

At step S576, the communication unit 281 transmits the response information supplied from the control unit 282 and representing that a service cannot be utilized to the service B client system 203 through the communication network 56, and the service provision process comes to an end. In this case, in FIG. 26, the process at step S534 is performed.

On the other hand, in the case where it is decided at step S574 that the service A nonstandard IC card 201 is a usable card, the control unit 282 decides at step S577 whether or not the access of the service B to the service A is permitted. For example, in the case where response information that the access is not permitted is transmitted from the service A auxiliary system 55, it is decided that the access is not permitted.

In the case where it is decided at step S577 that the access is not permitted, the communication unit 281 receives, at step S578, response information transmitted from the service A auxiliary system 55 through the communication network 56 and representing that the access is not permitted and supplies the response information to the control unit 282. Further, the control unit 282 that receives the supply of the response information supplies the response information to the communication unit 281.

At step S579, the communication unit 281 transmits the response information supplied from the control unit 282 and representing that the access is not permitted to the service B client system 203 through the communication network 56, and the service provision process comes to an end. In this case, in FIG. 26, the process at step S537 is performed.

It is to be noted that, in the case where the access of the service B to the service A is not permitted, the service B may be provided within a range within which access to the service A is not required.

On the other hand, in the case where it is decided at step S577 that the access is permitted, the processing advances to step S580. In this case, from the service A auxiliary system 55, a list of APIs that can be utilized by the service B cloud server 204 is transmitted together with the response information that the access is permitted.

At step S580, the communication unit 281 receives the response information that the access is permitted and the API list transmitted from the service A auxiliary system 55 through the communication network 56 and supplies them to the control unit 282.

Consequently, the control unit 282 selects, from within the API list supplied from the communication unit 281, an API that is required upon service provision to the user. Further, the control unit 282 generates a process request for calling a necessary API such as information indicative of the selected API (program), namely, a process request for requesting execution of the API, in response to a result of the selection, and supplies the process request to the communication unit 281. Consequently, a provision request of information to be acquired from the service A cloud server 54, which is required, for example, upon provision of the service B, is generated as the process request.

At step S581, the communication unit 281 transmits the process request supplied from the control unit 282 to the service A auxiliary system 55 through the communication network 56. It is to be noted that the process request may otherwise be transmitted directly to the service A cloud server 54.

When the process request is transmitted, the service A cloud server 54 executes a process according to the process request, and a result of the execution of the process is transmitted from the service A cloud server 54 to the service B cloud server 204. The execution result of the process is information obtained, for example, by extracting part of medication history information recorded in the service A cloud server 54 or the like.

At step S582, the communication unit 281 receives the execution result of the process transmitted from the service A cloud server 54 and supplies the execution result to the control unit 282. It is to be noted that the execution result of the process may otherwise be received from the service A cloud server 54 through the service A auxiliary system 55.

At step S583, the service provision unit 291 executes a process for providing a service to the user using the execution result of the process supplied from the communication unit 281 and the nonstandard ID received at step S571, and the service provision process comes to an end.

In particular, for example, the service provision unit 291 generates display data for displaying the execution result of the process supplied from the communication unit 281, information relating to the user recorded in an associated relationship with the nonstandard ID in the recording unit 283 or the like, and supplies the display data to the communication unit 281. Then, the communication unit 281 transmits the display data supplied from the service provision unit 291 to the service B client system 203 through the communication network 56.

The service B cloud server 204 provides the service B to the user suitably in collaboration with the service A cloud server 54 in such a manner as described above. Consequently, a new service can be provided to the user, and the convenience can be improved.

Figure 27:
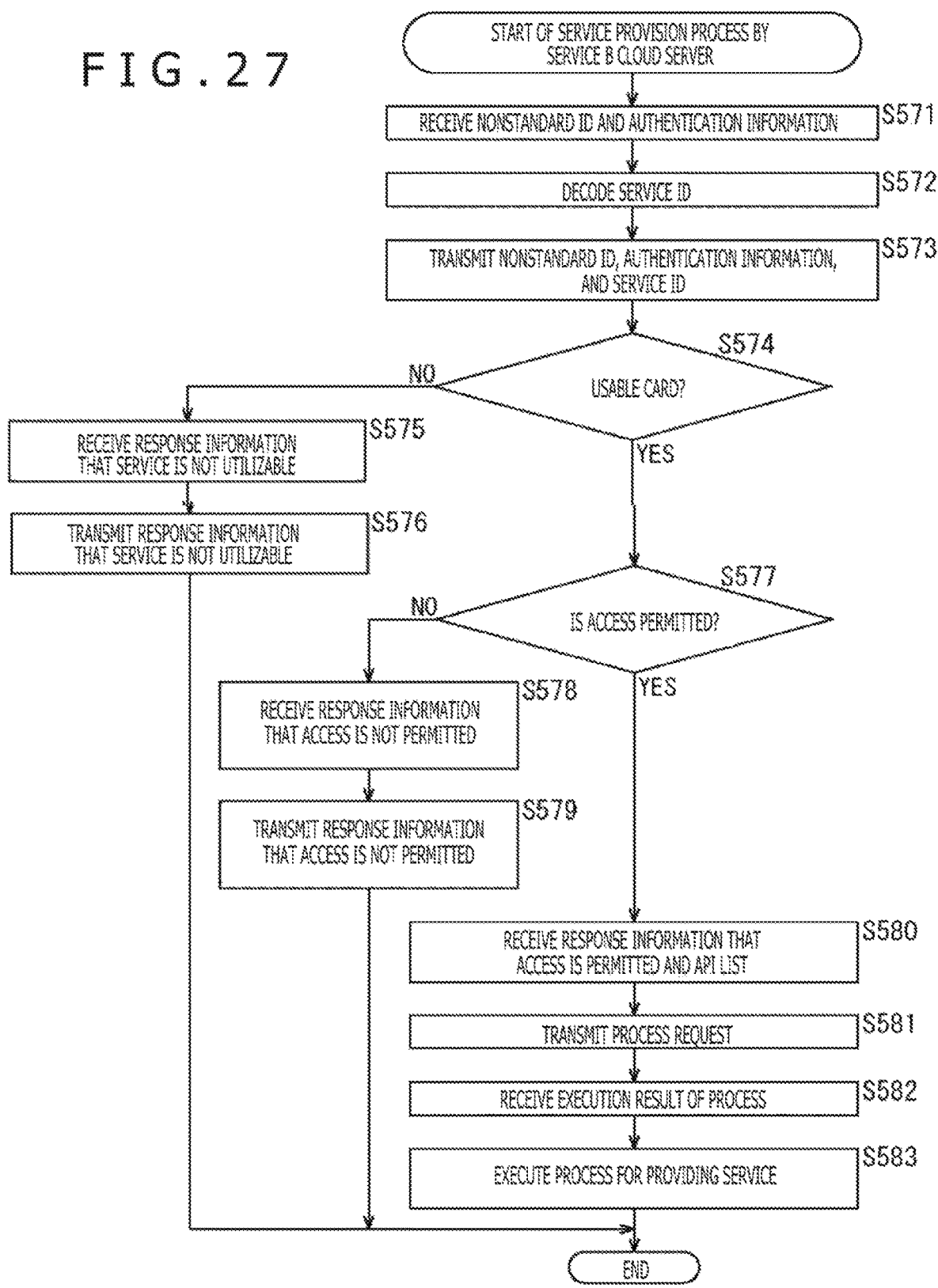
FIG. 27 is a flow chart illustrating a service provision process.

Furthermore, a process performed by the service A auxiliary system 55 and the service A cloud server 54 when the service provision process described hereinabove with reference to FIG. 27 is performed is described.

In particular, in the following, a collaboration service provision auxiliary process by the service A auxiliary system 55 and a collaboration service provision process by the service A cloud server 54 are described with reference to a flow chart of FIG. 28.

At step S611, the communication unit 161 of the service A auxiliary system 55 receives a nonstandard ID, authentication information, and a service ID transmitted thereto from the service B cloud server 204 by the process at step S573 of FIG. 27 and supplies them to the control unit 162.

Consequently, an authentication process is performed thereafter at step S612. It is to be noted that, since the process at step S612 is similar to the process at step S112 of FIG. 9, description of it is omitted.

At step S613, the table management unit 172 searches for the nonstandard ID supplied from the communication unit 161 from within the ID correspondence table recorded in the recording unit 163.

At step S614, the control unit 162 decides from a result of the authentication process at step S612 and a result of the search at step S613 whether or not the service A nonstandard IC card 201 is a card that is usable by the service A.

For example, in the case where it is decided at step S612 that the service A nonstandard IC card 201 is a legitimate one and besides the nonstandard ID is recorded (registered) in the ID correspondence table at step S613, then the service A nonstandard IC card 201 is decided as a usable card.

In the case where it is decided at step S614 that the service A nonstandard IC card 201 is not a usable card, the control unit 162 generates response information that a service cannot be utilized and supplies the response information to the communication unit 161, and the processing advances to step S615.

At step S615, the communication unit 161 transmits the response information supplied from the control unit 162 and representing that a service cannot be utilized to the service B cloud server 204 through the communication network 56, and the collaboration service provision auxiliary process comes to an end. In this case, in the service B cloud server 204, the process at step S575 of FIG. 27 is performed.

In contrast, in the case where it is decided at step S614 that the service A nonstandard IC card 201 is a usable card, the table management unit 172 reads out, at step S616, a standard ID associated with the nonstandard ID received at step S611 from the ID correspondence table on the basis of a result of the search at step S613.

At step S617, the control unit 162 searches for the service ID received at step S611 and recorded in an associated relationship with the standard ID obtained at step S616 as other-service access permission information recorded in the recording unit 163.

At step S618, the control unit 162 decides on the basis of a result of the search at step S617 whether or not access of the service B cloud server 204 to the service A cloud server 54 is permitted. In other words, it is decided whether or not access of the service B to the service A is permitted.

For example, in the case where other-service access permission information including the standard ID obtained at step S616 and the service ID received at step S611 is recorded in the recording unit 163, in short, in the case where the service ID is found out as a result of the search at step S617, it is decided that the access is permitted.

In the case where it is decided at step S618 that the access is not permitted, the control unit 162 generates response information that the access is not permitted and supplies the response information to the communication unit 161, and the processing advances to step S619.

At step S619, the communication unit 161 transmits the response information supplied from the control unit 162 and representing that the access is not permitted to the service B cloud server 204 through the communication network 56, and the collaboration service provision auxiliary process comes to an end. In this case, in the service B cloud server 204, the process at step S578 of FIG. 27 is performed.

In contrast, in the case where it is decided at step S618 that the access is permitted, the control unit 162 generates response information that the access is permitted and supplies the response information to the communication unit 161, and the processing advances to step S620.

At step S620, the other-service processing unit 311 reads out an API list recorded in an associated relationship with the service ID received at step S611 from the recording unit 163 and supplies the API list to the communication unit 161.

At step S621, the communication unit 161 transmits the response information supplied from the control unit 162 and representing that the access is permitted and the API list, both supplied from the control unit 162 to the service B cloud server 204 through the communication network 56.

Consequently, in the service B cloud server 204, the process at step S580 of FIG. 27 is performed and the process at step S581 is executed, and a process request is transmitted to the service B cloud server 204.

At step S622, the communication unit 161 receives the process request transmitted from the service B cloud server 204 and supplies the process request to the control unit 162.

Consequently, the other-service processing unit 311 executes, at step S623, a process according to the process request supplied from the communication unit 161 using the standard ID obtained at step S616. In particular, the other-service processing unit 311 executes the API recorded in the recording unit 163 in response to the process request to control execution of processes at later steps S624 and S625.

At step S624, the table management unit 172 of the control unit 162 acquires, on the basis of the standard ID obtained at step S616, service utilization additional information recorded in an associated relationship with the standard ID from the ID correspondence table of the recording unit 163 in response to the request of the other-service processing unit 311.

Consequently, the other-service processing unit 311 generates a process execution request for requesting execution of a process according to the process request from the service B cloud server 204 based on the standard ID and the service utilization additional information and supplies the process execution request and the service utilization additional information to the communication unit 161.

At step S625, the communication unit 161 transmits the standard ID, the service utilization additional information, and the process execution request supplied from the other-service processing unit 311 to the service A cloud server 54 through the communication network 56 and instructs the service A cloud server 54 to access the service B cloud server 204, and the collaboration service provision auxiliary process comes to an end.

Further, after the standard ID, the service utilization additional information, and the process execution request are transmitted, a collaboration service provision process is performed in the service A cloud server 54.

In particular, at step S651, the communication unit 121 of the service A cloud server 54 receives the standard ID, the service utilization additional information, and the process execution request transmitted thereto from the service A auxiliary system 55 and supplies them to the control unit 122.

At step S652, the service provision unit 131 executes a process according to the process execution request on the basis of the standard ID and the service utilization additional information supplied thereto from the communication unit 121.

In particular, for example, the service provision unit 131 reads out part of medication history information recorded in an associated relationship with the standard ID from the recording unit 123 in response to the process execution request and supplies the read out medication history information and part of the service utilization additional information as an execution result of the process to the communication unit 121.

At step S653, the communication unit 121 transmits the execution result of the process supplied from the service provision unit 131 to the service B cloud server 204 designated by the service A auxiliary system 55 under the control of the service provision unit 131, and the collaboration service provision process comes to an end. Consequently, in the service B cloud server 204, the process at step S582 of FIG. 27 is performed.

In this manner, the service A auxiliary system 55 performs an authentication process on the basis of authentication information and confirms access permission on the basis of other-service access permission information recorded in advance. Consequently, collaboration with another service is made possible while the security is assured sufficiently, and the convenience can be improved.

<Example of Application of Service Provision System>

Figure 29:
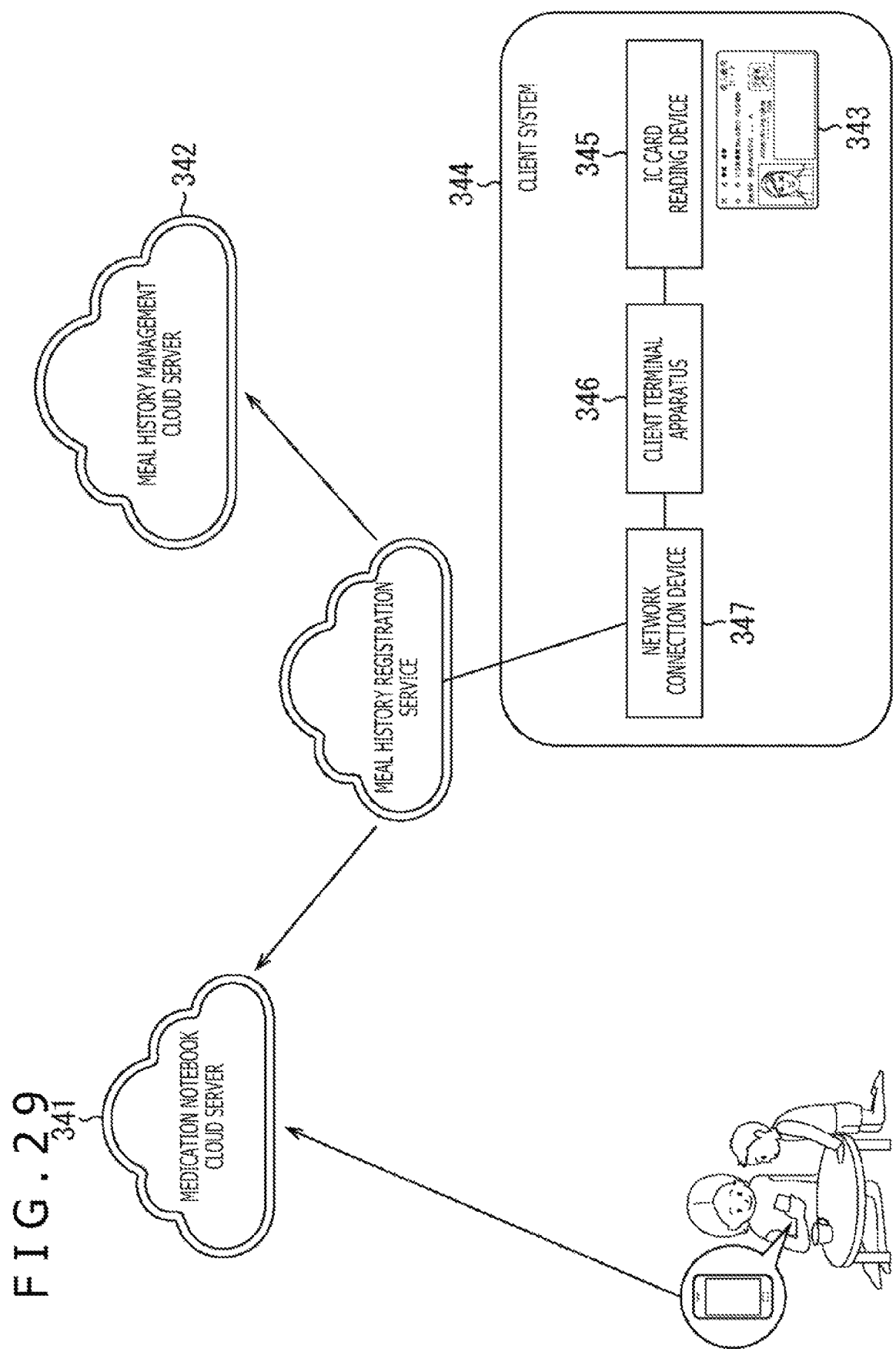
FIG. 29 is a view illustrating an example of application of the service provision system.
Figure 30:
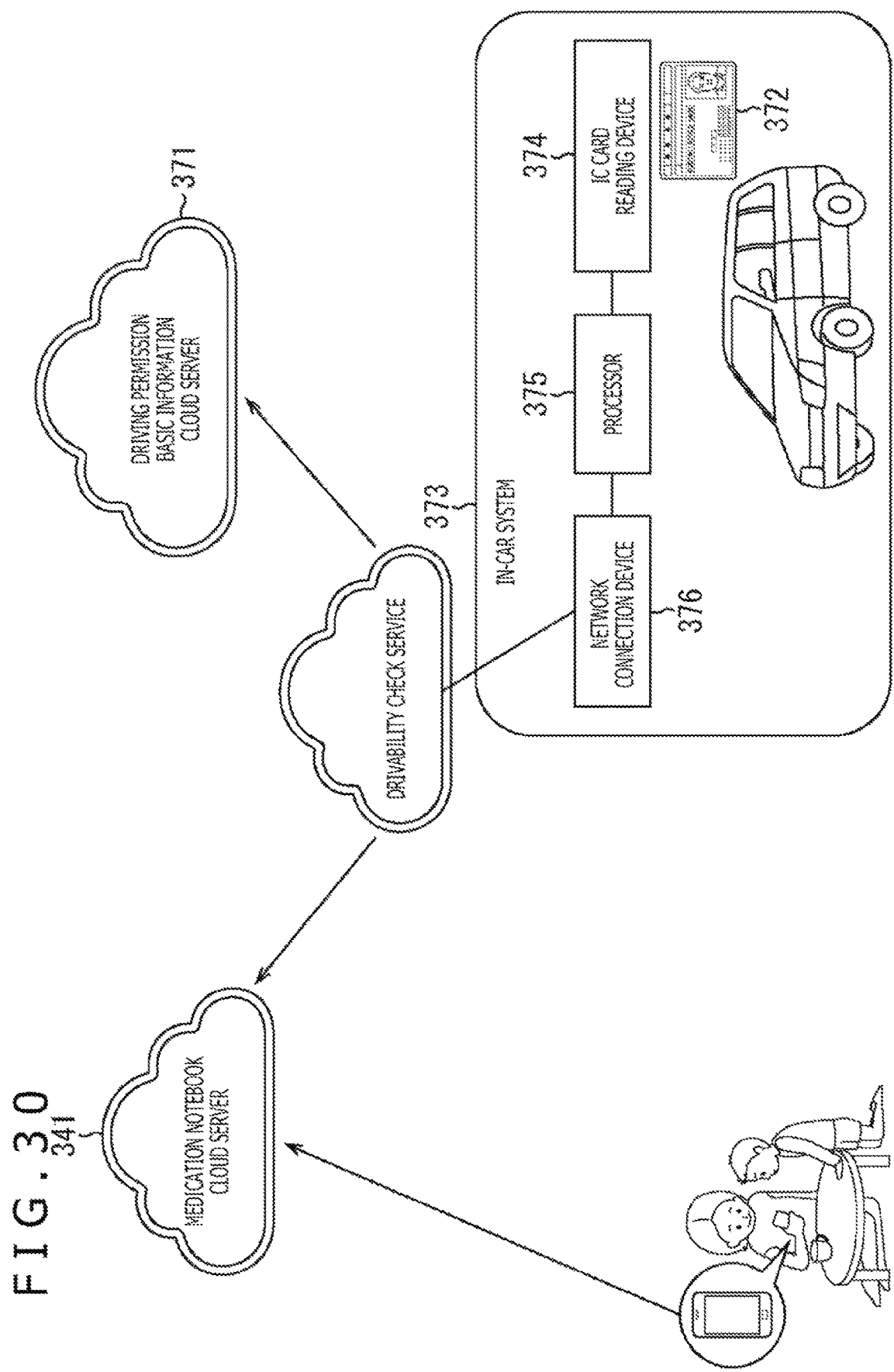
FIG. 30 is a view illustrating an example of application of the service provision system.

The service provision system described in the foregoing description of the second embodiment can be applied to such examples as depicted in FIGS. 29 and 30.

For example, the example depicted in FIG. 29 is an example in which a service relating to browsing, search and so forth of a medication notebook provided by a medication notebook cloud server 341 and a service relating to management of the meal history of a user whose is a patient of a nursing home or the like provided by a meal history management cloud server 342 collaborate with each other.

In this example, a user possesses a My Number card 343 and uses the My Number card 343 to utilize a meal history registration service provided by the meal history management cloud server 342 in a client system 344 provided in the nursing home or the like.

Further, the My Number card 343 owned by the user is registered as a nonstandard IC card also in the medication notebook cloud server 341, and the user can utilize a service provided by the medication notebook cloud server 341 utilizing the My Number card 343. Furthermore, in the medication notebook cloud server 341, access to the meal history management cloud server 342 in regard to the user is permitted by the other-service access permission information described hereinabove.

The client system 344 includes, for example, an IC card reading device 345, a client terminal apparatus 346, and a network connection device 347.

For example, in the case where the user utilizes the meal history registration service, the user would hold the My Number card 343 over the IC card reading device 345 such that the IC card reading device 345 reads out the ID information and the authentication information of the user from the My Number card 343 and supplies them to the client terminal apparatus 346. Here, the ID information of the user is, for example, the My Number or the like.

The client terminal apparatus 346 generates meal information catered currently to the user in response to an input of an employee or the like of a nursing home and records the meal information and the ID information of the user into a recording unit of the client terminal apparatus 346 itself. Further, the client terminal apparatus 346 transmits the meal information and the ID information of the user to the meal history management cloud server 342 through the network connection device 347 such that they are registered as a meal history into the meal history management cloud server 342.

Further, at this time, the meal history management cloud server 342 accesses the medication notebook cloud server 341 utilizing the ID information or the authentication information of the user and requests, regarding the meal substance to be catered currently, information of a meal that should not be taken in simultaneously with a medicine currently taken by the user or having been prescribed in the past to the user, and allergy history information of the user.

Consequently, the medication notebook cloud server 341 supplies, after it performs an authentication process and so forth by the ID information or the authentication information of the user or the other-service access permission information, information of meals that should not be taken in and allergy history information of the user to the meal history management cloud server 342 in response to the request of the meal history management cloud server 342.

Then, the meal history management cloud server 342 decides, from the information of the meals that should not be taken in and the allergy history information of the user acquired in this manner, whether or not there is a problem in the meal to be currently catered to the user. Then, if it is decided that there is a program in the meal substance to be catered, then the meal history management cloud server 342 causes the client terminal apparatus 346 to display a warning.

In this manner, according to the present technology, the medication notebook cloud server 341 and the meal history management cloud server 342 can collaborate with each other to provide a service to a user. In this example, the medication notebook cloud server 341 corresponds to the service A cloud server 54 and the service A auxiliary system 55 depicted in FIG. 21, and the meal history management cloud server 342 corresponds to the service B cloud server 204 depicted in FIG. 21.

Further, for example, the example depicted in FIG. 30 is an example in which a service relating to browsing, search and so forth of a medication notebook provided by the medication notebook cloud server 341 and a service relating to management of driving permission basic information or confirmation of drivability provided by a driving permission basic information cloud server 371 collaborate with each other. It is to be noted that, in FIG. 30, portions corresponding to those in the case of FIG. 29 are denoted by the same reference characters, and description of the same is omitted.

In this example, the user owns a driver's license 372 and uses the driver's license 372 to utilize a drivability check service provided by the driving permission basic information cloud server 371 in an in-car system 373 provided in a passenger car of the user itself.

It is to be noted that, although the drivability check service may be provided by an apparatus different from the driving permission basic information cloud server 371, it is assumed here that it is provided by the driving permission basic information cloud server 371. For example, in the case where the drivability check service is provided by some other apparatus, the drivability check service collaborates not only with the medication notebook cloud server 341 but also with the driving permission basic information cloud server 371 to perform service provision.

Further, the driver's license 372 owned by the user is registered as a nonstandard IC card also in the medication notebook cloud server 341, and the user can utilize the driver's license 372 to utilize a service provided by the medication notebook cloud server 341. Further, in the medication notebook cloud server 341, access to the driving permission basic information cloud server 371 regarding the user is permitted by the other-service access permission information described above.

The in-car system 373 includes, for example, an IC card reading device 374, a processor 375, and a network connection device 376.

For example, in the case where the user utilizes the drivability check service, the user would hold the driver's license 372 over the IC card reading device 374 upon starting of driving of the passenger car (vehicle). Consequently, the IC card reading device 374 reads out the ID information and the authentication information of the user from the driver's license 372 and supplies them to the processor 375. Here, the ID information of the user is, for example, a license number or the like.

The processor 375 transmits the ID information and the authentication information of the user to the driving permission basic information cloud server 371 through the network connection device 376 and requests confirmation of drivability of the vehicle by the user.

In response to this, the driving permission basic information cloud server 371 suitably performs an authentication process on the basis of the received ID information or authentication information of the user and reads out the driving permission basic information of the user recorded by the user itself in an associated relationship with the ID information. This driving permission basic information is information regarding permission of driving by the user managed, for example, by the administration.

Further, at this time, the driving permission basic information cloud server 371 accesses the medication notebook cloud server 341 utilizing the ID information or the authentication information of the user and requests drivability information indicating that driving is inhibited, driving is to be noticed, driving is possible or the like in regard to a medicine being currently taken in by the user or prescribed in the past to the user.

Consequently, the medication notebook cloud server 341 first performs an authentication process or the like from the ID information or the authentication information of the user or the other-service access permission information and then supplies the drivability information to the driving permission basic information cloud server 371 in response to a request of the driving permission basic information cloud server 371.

Then, the driving permission basic information cloud server 371 supplies, from the drivability information obtained in this manner and the driving permission basic information, information whether driving is permitted to the user, whether driving is inhibited, or that notice is required although driving is permitted as a confirmation result of the drivability to the in-car system 373.

The processor 375 controls the vehicle in response to a confirmation result of the drivability. For example, in the case where it is confirmed that driving is inhibited, the processor 375 performs such control as to inhibit starting of the engine, in the case where notice is required for driving, to restrict the highest speed or sudden acceleration upon traveling or to lower the threshold value with which a brake assist function is to be activated.

In this manner, according to the present technology, the medication notebook cloud server 341 and the driving permission basic information cloud server 371 can collaborate with each other to provide a service to a user. In this example, the medication notebook cloud server 341 corresponds to the service A cloud server 54 and the service A auxiliary system 55 depicted in FIG. 21, and the driving permission basic information cloud server 371 corresponds to the service B cloud server 204 depicted in FIG. 21.

Third Embodiment

<Example of Configuration of Service Provision System>

Incidentally, in the description of the second embodiment, an example is described in which services collaborate with each other to perform service provision to a user.

Further, when service collaboration is to be performed, for example, if a common contrivance necessary for service collaboration is extracted and used as a platform, then it is possible to reduce the introduction cost of a service provider when service collaboration is performed.

In particular, by managing, for example, an authentication process of ID information for each ID type, an ID reading out process of ID information, an API list for other-services, other-service access permission information, access information to other-service management information and so forth by the platform, service providers can combine those processes to implement individual service collaboration.

Further, also in the case where such a contrivance as can set other-service access permission information is required, by generating an access destination of a user terminal apparatus for setting in the platform, a service provider need not uniquely prepare an access destination of the user terminal apparatus any more.

Figure 31:
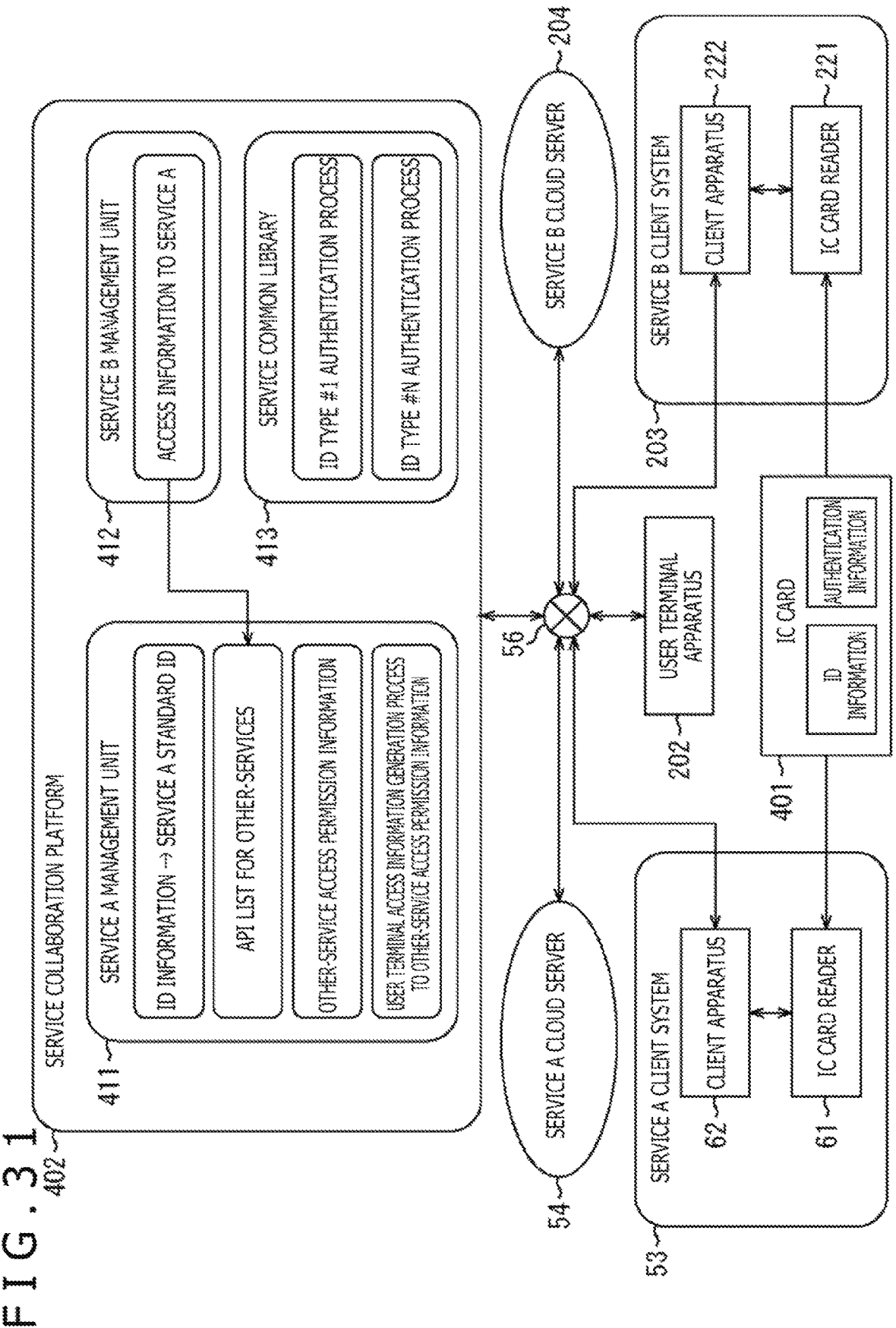
FIG. 31 is a view depicting an example of a configuration of the service provision system.

Therefore, in the present technology, a platform is provided in a service provision system, for example, as depicted in FIG. 31 to make it possible to perform service collaboration more simply, in short, at a reduced cost. It is to be noted that, in FIG. 31, portions corresponding to those in the case in FIG. 21 are denoted by the same reference characters, and description of the same is omitted suitably.

In the service provision system depicted in FIG. 31, the service A and the service B collaborate with each other to provide a service to a user.

In the example of FIG. 31, the service provision system includes an IC card 401, a user terminal apparatus 202, a service A client system 53, a service A cloud server 54, a service B client system 203, a service B cloud server 204, and a service collaboration platform 402.

Further, in the service provision system, the user terminal apparatus 202, the service A client system 53, the service A cloud server 54, the service B client system 203, the service B cloud server 204, and the service collaboration platform 402 are connected to each other through a communication network 56.

In this example, the user will utilize the IC card 401 to receive provision of the service A or the service B. The IC card 401 has recorded therein at least ID information and authentication information for uniquely identifying the user. The ID information and the authentication information correspond to the nonstandard ID and the authentication information recorded in the service A nonstandard IC card 201 depicted in FIG. 21.

It is to be noted that the IC card 401 need not be a card for exclusive use for the service A or the service B.

Further, when the ID information is to be read out from the IC card 401 upon service utilization, a card of which type the IC card 401 is such as a driver's license is specified from the communication format with the IC card 401, for example, from the format of polling, the structure of information or identification information recorded in the IC card 401 and so forth. Then, service provision is performed using the ID type information indicative of the type of the IC card 401, namely, of the type of the ID information, and the ID information. It is to be noted that the ID type information may be recorded otherwise in the IC card 401.

The service collaboration platform 402 has a service A management unit 411 for performing information management and so forth in regard to the service A, a service B management unit 412 for performing information management and so forth in regard to the service B, and a service common library 413 for performing a process common to the individual services.

The service A management unit 411 performs an ID reading out process of the service A standard ID when the service A is to be utilized, which has been read out from the IC card 401 and corresponds to ID information of the type indicated by the ID type information. Here, the service A standard ID corresponds to the standard ID of the service A described above.

Further, the service A management unit 411 performs also management of an API for some different service regarding the service A, namely, in the present example, for the service B, an API list, and other-service access permission information. Here, the other-service access permission information can be set for each of services different from the service A such as the service B.

Further, the API managed by the service A management unit 411 is a program for implementing (executing) a process for requesting execution of a process for providing the service A to the service A cloud server 54 similarly as in the case in the second embodiment described hereinabove.

Furthermore, the service A management unit 411 performs also a process for generating user terminal access information indicative of an access destination of the user terminal apparatus 202 when the user sets other-service access permission information. The user terminal access information is, for example, a URL (Unified Resource Locator) or the like.

This user terminal access information is supplied to the user terminal apparatus 202 by some method. For example, the user terminal access information may be supplied directly from the service collaboration platform 402 to the user terminal apparatus 202 or may be supplied from the service collaboration platform 402 to the user terminal apparatus 202 through the service A cloud server 54 or the service A client system 53. Alternatively, the user terminal access information may be recorded in a service for exclusive use for the service A in advance such that the user terminal access information is supplied from the server to the user terminal apparatus 202.

The user terminal apparatus 202 can access an access destination indicated by the acquired user terminal access information to set access permission to the service A for each service, for example, on a web page or the like. The method for setting of access permission to the service A by the user terminal apparatus 202, in short, for setting of other-service access permission information, is similar to that in the case of the second embodiment described hereinabove. In particular, the service A management unit 411 generates and records other-service access information in response to access from the user terminal apparatus 202, namely, in response to a result of an input of the user or the like.

It is to be noted that, also in this example, not the user terminal apparatus 202 but some other apparatus such as the service A client system 53 may set access permission of each service to the service A.

The service B management unit 412 manages information required for access from the service B to the service A as access information to the service A. In particular, the access information is information necessary for the service B management unit 412 to access information managed by the service A management unit 411.

For example, the access information is a certificate of a service ID or the like encrypted with a secrete key, which is acquired from the service A management unit 411 in advance and indicates the service B, and a public key, or a pointer for information such as an API list or the like managed by the service A management unit 411 or the like.

The service common library 413 is configured from common library information common to individual services such as a public key or the like that is used to authenticate ID information for each ID type, namely, to authenticate the IC card 401, and such information is used to perform an authentication process of the ID information for each ID type, in short, of the IC card 401.

It is to be noted that description here is given of a case in which access from the service B to the service A is performed upon utilization of the service B as an example. Therefore, more particularly, also the service A management unit 411 performs management of access information to the service B and so forth, and also the service B management unit 412 performs management of an API list for other-services or other-service access permission information, an ID reading out process of ID information and so forth.

For example, in the case where the user utilizes the IC card 401 to receive provision of the service B collaborating with the service A, after an authentication process is performed on the basis of the service common library 413, access to the service A is performed on the basis of the access information to the service A. Then, access permission to the service A is confirmed by the service A management unit 411, and thereafter, collaboration of the service A and the service B is performed.

<Example of Configuration of Service Collaboration Platform>

Figure 32:
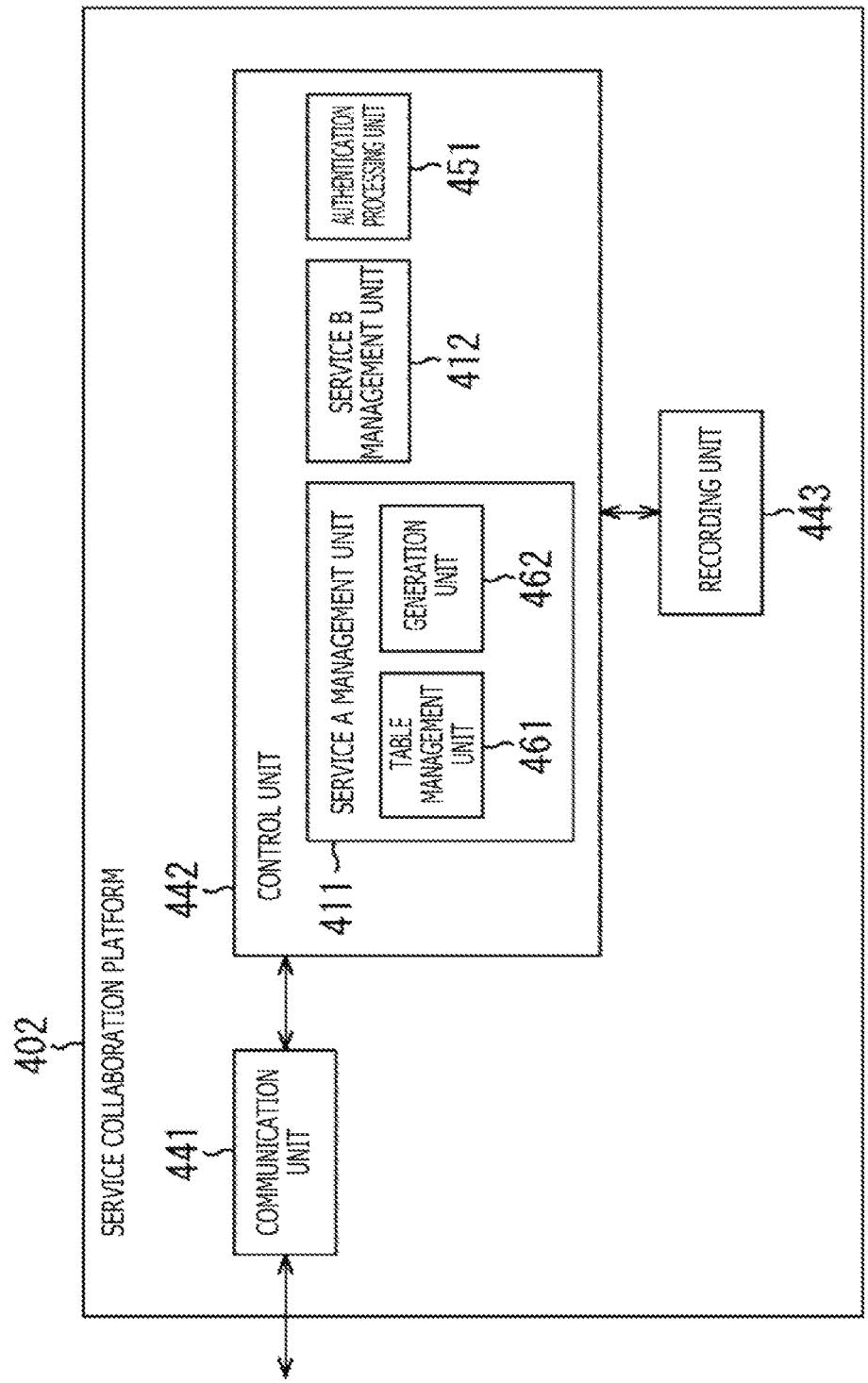
FIG. 32 is a view depicting an example of a configuration of a service collaboration platform.

Furthermore, the service collaboration platform 402 depicted in FIG. 31 is configured, for example, in such a manner as depicted in FIG. 32. It is to be noted that, in FIG. 32, portions corresponding to those in the case in FIG. 31 are denoted by the same reference characters, and description of the same is omitted. Further, the service collaboration platform 402 may be configured from a single information processing apparatus or may be configured from a plurality of apparatus.

The service collaboration platform 402 depicted in FIG. 32 includes a communication unit 441, a control unit 442, and a recording unit 443.

It is to be noted that the communication unit 441 to the recording unit 443 are basically similar to the communication unit 161 to the recording unit 163 described hereinabove with reference to FIG. 24 individually, and therefore, description of them is omitted suitably.

The communication unit 441 acquires various kinds of information or supplies various kinds of information through the communication network 56.

Further, the control unit 442 includes a service A management unit 411, a service B management unit 412, and an authentication processing unit 451. The authentication processing unit 451 performs an authentication process of the IC card 401 on the basis of information recorded in the recording unit 443 as the service common library 413 depicted in FIG. 31.

The service A management unit 411 generates user terminal access information using information relating to the user as occasion demands. Further, the service A management unit 411 includes a table management unit 461 and a generation unit 462. The table management unit 461 and the generation unit 462 correspond to the table management unit 172 and the generation unit 173 depicted in FIG. 24, respectively.

Figure 33:
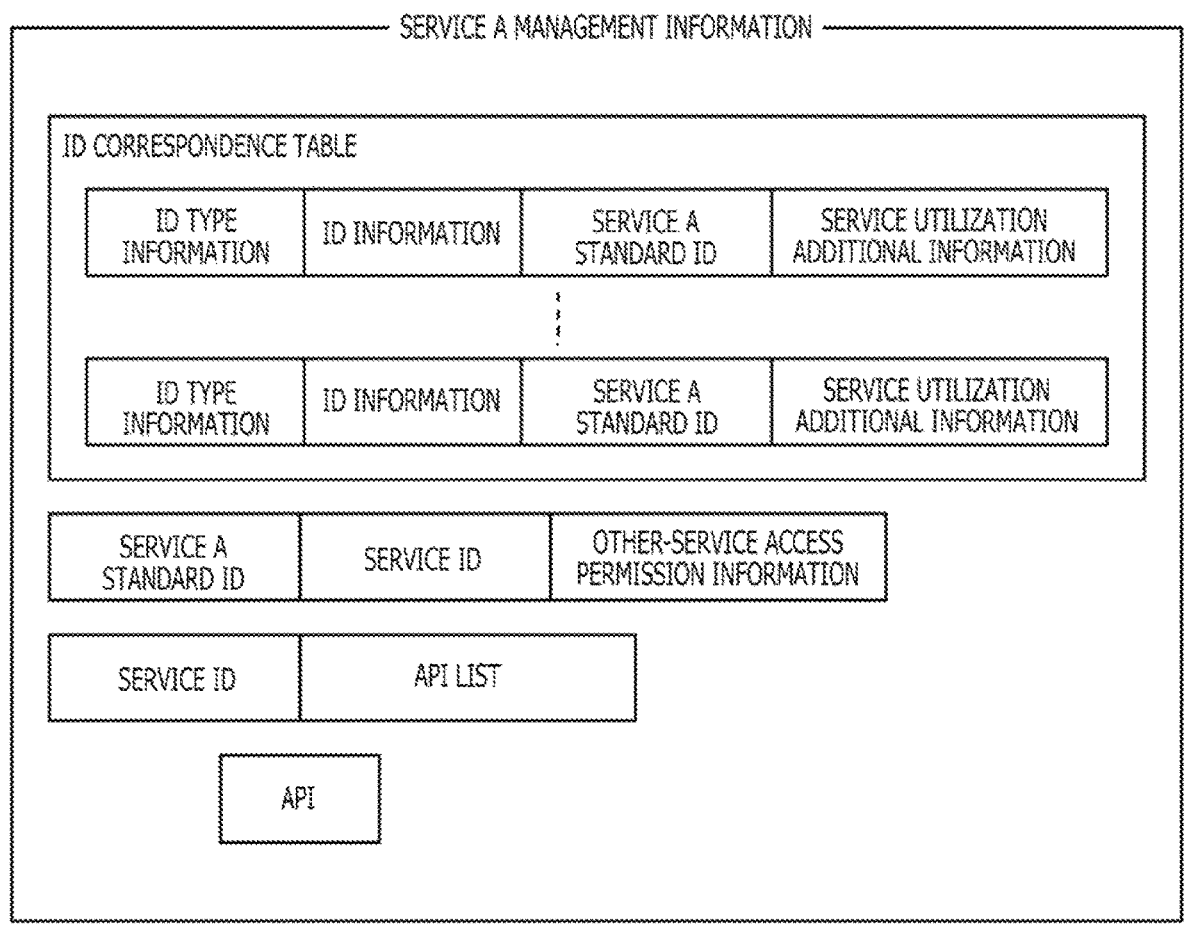
FIG. 33 is a view illustrating information managed by the service collaboration platform.

Furthermore, the recording unit 443 has recorded therein information depicted in FIG. 33 as service A management information relating to the service A managed by the service A management unit 411.

In particular, as the service A management information, an ID correspondence table, other-service access permission information, an API list, and an API of the service A are recorded.

In the ID correspondence table, service A standard IDs, ID type information, ID information, and service utilization additional information are recorded (registered) in an associated relationship with each other.

Further, the other-service access permission information is recorded in an associated relationship with the service A standard IDs and the service IDs. Furthermore, the API lists are recorded in an associated relationship with the service IDs.

In this example, the other-service access permission information is information indicative of whether or not a user indicated by the service A standard ID associated therewith permits access of the service indicated by the service ID associated therewith to the service A. Accordingly, each user can set whether or not access to the service A is to be permitted for each service.

In addition, as the service A management information, also an API for requesting execution of a predetermined process for providing the service A, which can be executed by the service A management unit 411, is recorded.

It is to be noted that, as the service A management information, user terminal access information may be recorded. Further, while description here is given of an example in which, upon provision of the service A, also service utilization additional information is utilized, the service utilization additional information need not necessarily be utilized.

<Process Upon Registration of IC Card>

Subsequently, operation of the service provision system depicted in FIG. 31 is described.

First, a process upon registration of the IC card 401 into the service collaboration platform 402 is described. Especially, a process by which registration of the IC card 401 regarding the service A is performed is described here.

Figure 34:
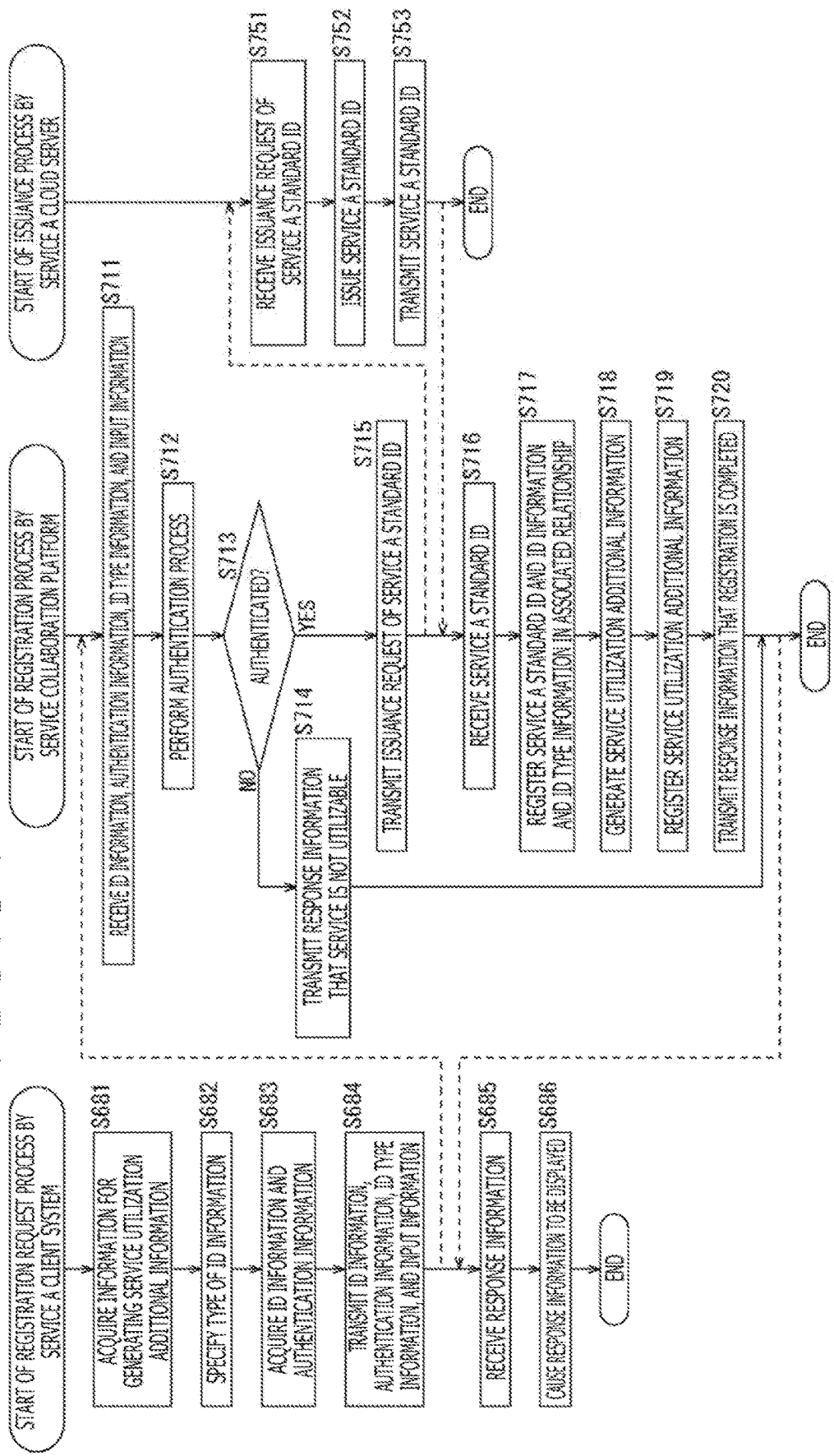
FIG. 34 is a flow chart illustrating a registration request process, a registration process, and an issuance process.

In the following, a registration request process by the service A client system 53, a registration process by the service collaboration platform 402 and an issuance process by the service A cloud server 54 are described with reference to a flow chart of FIG. 34.

For example, in the case where it is intended to register the IC card 401, the user would go to a pharmacy or the like in which the service A client system 53 is installed and requests registration. An employee or the like of the pharmacy or the like who receives the request will operate the inputting unit 94 of the client apparatus 62 to input information necessary for generation of service utilization additional information.

Consequently, at step S681, the control unit 93 acquires information for generating service utilization additional information, which is inputted by the employee or the like, in response to the signal supplied from the inputting unit 94 as input information.

After the information for generating service utilization additional information is inputted, the user would hold the IC card 401 possessed thereby over the IC card reader 61.

Consequently, at step S682, the IC card reader 61 performs communication with the IC card 401 under the control of the read-write controlling unit 92, and the read-write controlling unit 92 specifies the type of the ID information from the format of the communication, the data structure of the information in the IC card 401 and so forth.

At step S683, the IC card reader 61 acquires ID information and authentication information from the IC card 401 under the control of the read-write controlling unit 92 and supplies the acquired information to the read-write controlling unit 92.

The read-write controlling unit 92 supplies the ID information and the authentication information supplied from the IC card reader 61 and the ID type information indicative of the type specified at step S682 to the communication unit 91 through the control unit 93. Further, the control unit 93 supplies the acquired input information to the communication unit 91.

At step S684, the communication unit 91 transmits the ID information, the authentication information, the ID type information, and the input information to the service collaboration platform 402 through the communication network 56.

After the standard ID, the authentication information, the ID type information, and the input information are transmitted in this manner, at step S711, the communication unit 441 of the service collaboration platform 402 receives the ID information, the authentication information, the ID type information, and the input information transmitted from the client apparatus 62 and supplies them to the control unit 442.

At step S712, the authentication processing unit 451 of the control unit 442 performs an authentication process of the IC card 401 on the basis of the received authentication information. It is to be noted that, since the authentication process performed at step S712 is similar to the process at step S22 of FIG. 7, description of it is omitted. However, in this case, necessary information is read out from the service common library 413 on the basis of the ID type information, and an authentication process is performed.

At step S713, the authentication processing unit 451 decides whether or not the IC card 401 is authenticated.

In the case where it is decided at step S713 that the IC card 401 is not authenticated, the service A management unit 411 generates response information that a service cannot be utilized with the IC card 401. Then, the service A management unit 411 supplies the generated response information to the communication unit 441, and the processing advances to step S714.

At step S714, the communication unit 441 transmits the response information supplied from the service A management unit 411 and representing that a service cannot be utilized to the client apparatus 62 through the communication network 56, and the registration comes to an end.

In contrast, in the case where it is decided at step S713 that the IC card 401 is authenticated, the service A management unit 411 supplies an issuance request of a service A standard ID to the communication unit 441, and the processing advances to step S715.

At step S715, the communication unit 441 transmits the issuance request supplied from the service A management unit 411 to the service A cloud server 54 through the communication network 56.

Consequently, processes at steps S751 to S753 are executed in the service A cloud server 54, and the issuance process comes to an end. In the issuance process, a service A standard ID is issued, and the service A standard ID is transmitted to the service collaboration platform 402.

It is to be noted that, since the processes at steps S751 to S753 are similar to the processes at steps S51 to S53 of FIG. 7 individually, description of them is omitted. However, at steps S751 to S753, not a standard ID but a service A standard ID is issued.

At step S716, the communication unit 441 of the service collaboration platform 402 receives the service A standard ID transmitted from the service A cloud server 54 and supplies it to the service A management unit 411.

At step S717, the table management unit 461 of the service A management unit 411 registers the ID information and the ID type information received at step S711 and the service A standard ID received at step S716 in an associated relationship with each other.

In particular, the table management unit 461 performs registration by generating an ID correspondence table including ID information, ID type information, and service A standard IDs associated with each other and supplying the ID correspondence table to the recording unit 443 so as to be recorded into the recording unit 443.

At step S718, the generation unit 462 of the service A management unit 411 generates service utilization additional information on the basis of the input information received at step S711. It is to be noted that, in the process at step S718, a process similar to the process at step S28 of FIG. 7 is performed.

At step S719, the table management unit 461 of the service A management unit 411 registers the generated service utilization additional information. In particular, the table management unit 461 supplies the service utilization additional information to the recording unit 443, by which the service utilization additional information is recorded in an associated relationship with the service A standard ID received at step S716 into the ID correspondence table.

Further, the service A management unit 411 generates response information representing that registration of the IC card 401 is completed and supplies the response information to the communication unit 441.

At step S720, the communication unit 441 transmits the response information that registration is completed to the service A client system 53 through the communication network 56, and the registration process comes to an end.

Further, if the process at step S714 or S720 is performed to transmit the response information, then processes at steps S685 and S686 are performed thereafter in the service A client system 53, and the registration request process comes to an end. It is to be noted that, since the processes are similar to the processes at steps S14 and S15 of FIG. 7, description of them is omitted.

In this manner, in the service provision system, after authentication of the IC card 401 is performed, a service A standard ID is issued newly to the user, and the service A standard ID and the ID information and the ID type information for specifying the IC card 401, namely, the user, are recorded in an associated relationship with each other and also service utilization additional information is recorded.

Consequently, it becomes possible for the user to utilize the service A using the IC card 401, and the convenience can be improved.

<Process Upon Service Provision Utilizing Service Collaboration>

Further, the user can receive provision of the service B collaborating with the service A using the IC card 401. In the following, a process of the service provision system performed in such a case as just described is described.

First, a service utilization process by the service B client system 203 is described with reference to a flow chart of FIG. 35.

In the case where the user intends to receive provision of the service B using the IC card 401, the user would hold the IC card 401 over the IC card reader 221 of the service B client system 203.

Consequently, at step S781, the IC card reader 221 performs communication with the IC card 401 under the control of the read-write controlling unit 252, and the read-write controlling unit 252 specifies the type of the ID information from the format of the communication, the data structure of information in the IC card 401 or the like.

At step S782, the IC card reader 221 acquires the ID information and the authentication information from the IC card 401 under the control of the read-write controlling unit 252 and supplies them to the read-write controlling unit 252.

The read-write controlling unit 252 supplies the ID information and the authentication information supplied from the IC card reader 221 and the ID type information indicative of the type specified at step S781 to the communication unit 251 through the control unit 253.

At step S783, the communication unit 251 transmits the ID information, the authentication information, and the ID type information to the service B cloud server 204 through the communication network 56.

After the ID information, the authentication information, and the ID type information are transmitted, processes at steps S784 to S790 are performed, and the service utilization process comes to an end. However, the processes at steps S784 to S790 are similar to the processes at steps S533 to S539 of FIG. 26 individually, description of them is omitted.

The service B client system 203 acquires the ID information and the authentication information from the IC card 401 and transmits them together with the ID type information to the service B cloud server 204 in such a manner as described. Consequently, the user can receive provision of the service B collaborating with the service A, and the convenience can be improved.

Figure 35:
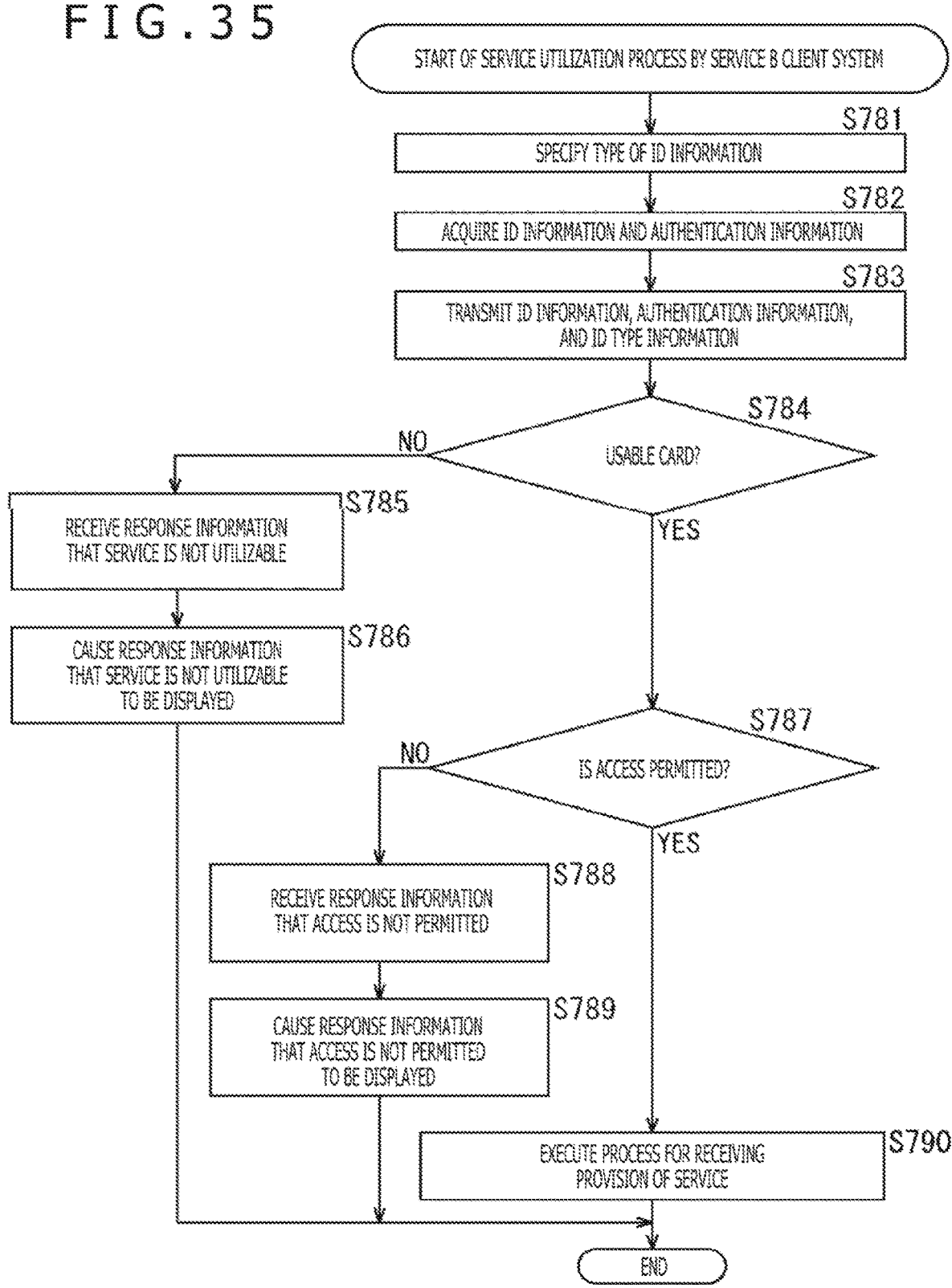
FIG. 35 is a flow chart illustrating a service utilization process.

Subsequently, a process performed by the service B cloud server 204 when the service utilization process described hereinabove with reference to FIG. 35 is performed is described. In particular, the service provision process by the service B cloud server 204 is described below with reference to a flow chart of FIG. 36.

After ID information, authentication information, and ID type information are transmitted from the service B client system 203 by the process at step S783 of FIG. 35, at step S821, the communication unit 281 receives the ID information, the authentication information, and the ID type information transmitted thereto and supplies them to the control unit 282.

Further, the control unit 282 supplies the received ID information, authentication information, and ID type information to the communication unit 281. Furthermore, at this time, the control unit 282 authenticates the IC card 401 on the basis of the authentication information as occasion demands.

At step S822, the communication unit 281 transmits the ID information, the authentication information, and the ID type information supplied thereto from the control unit 282 to the service collaboration platform 402 through the communication network 56.

After the ID information, the authentication information, and the ID type information are transmitted, processes at steps S823 to S832 are performed, and the service provision process comes to an end. However, since the processes at steps S823 to S832 are similar to the processes at steps S574 to S583 of FIG. 27 individually, description of them is omitted. However, at steps S823 to S830, transfer of the individual information with the service collaboration platform 402 is performed.

The service B cloud server 204 suitably collaborates with the service A cloud server 54 to provide the service B to a user in such a manner as described above. Consequently, a new service can be provided to the user, and the convenience can be improved.

Figure 36:
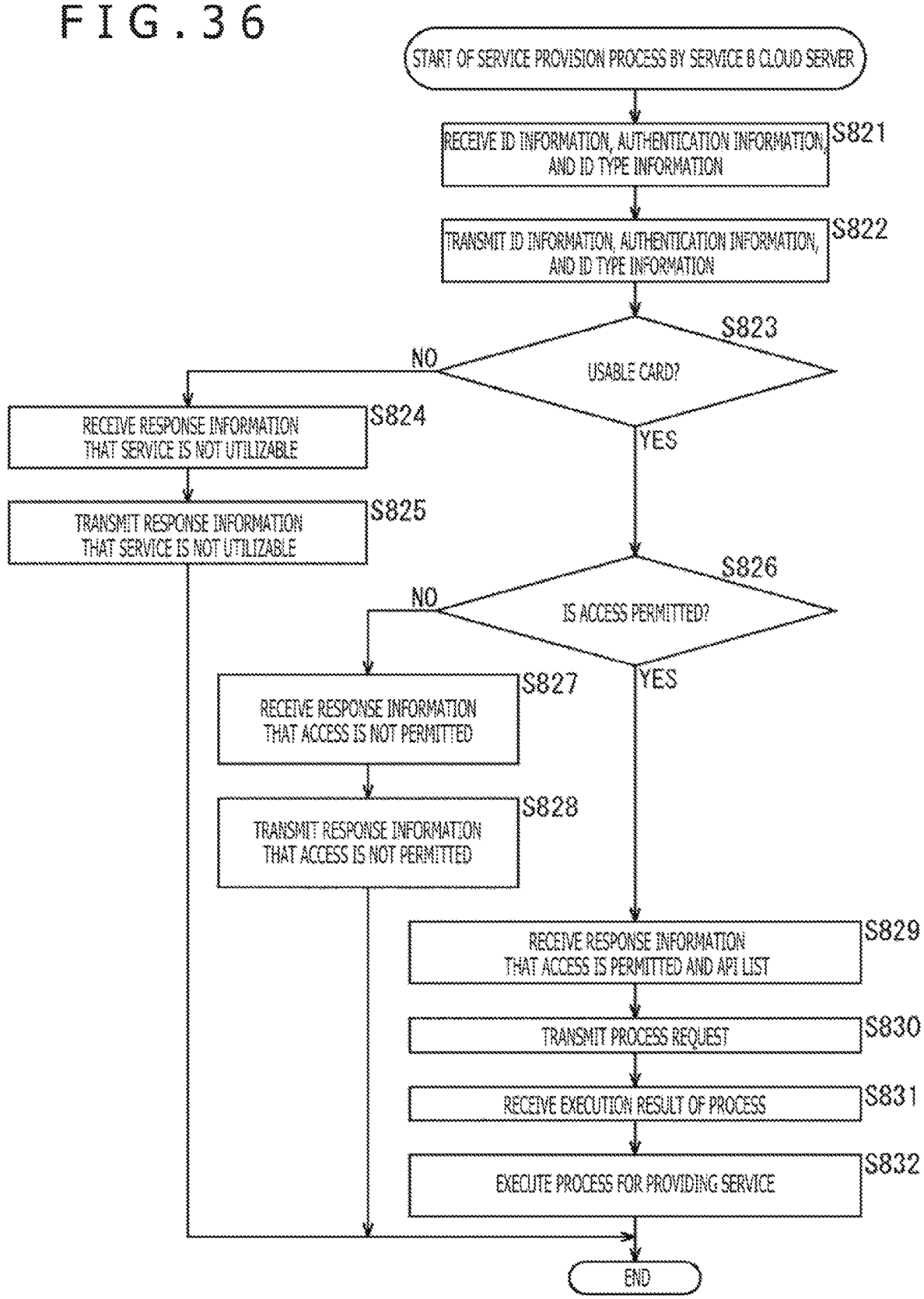
FIG. 36 is a flow chart illustrating a service provision process.

Furthermore, a process performed by the service collaboration platform 402 and the service A cloud server 54 when the service provision process described hereinabove with reference to FIG. 36 is performed is described.

Figure 37:
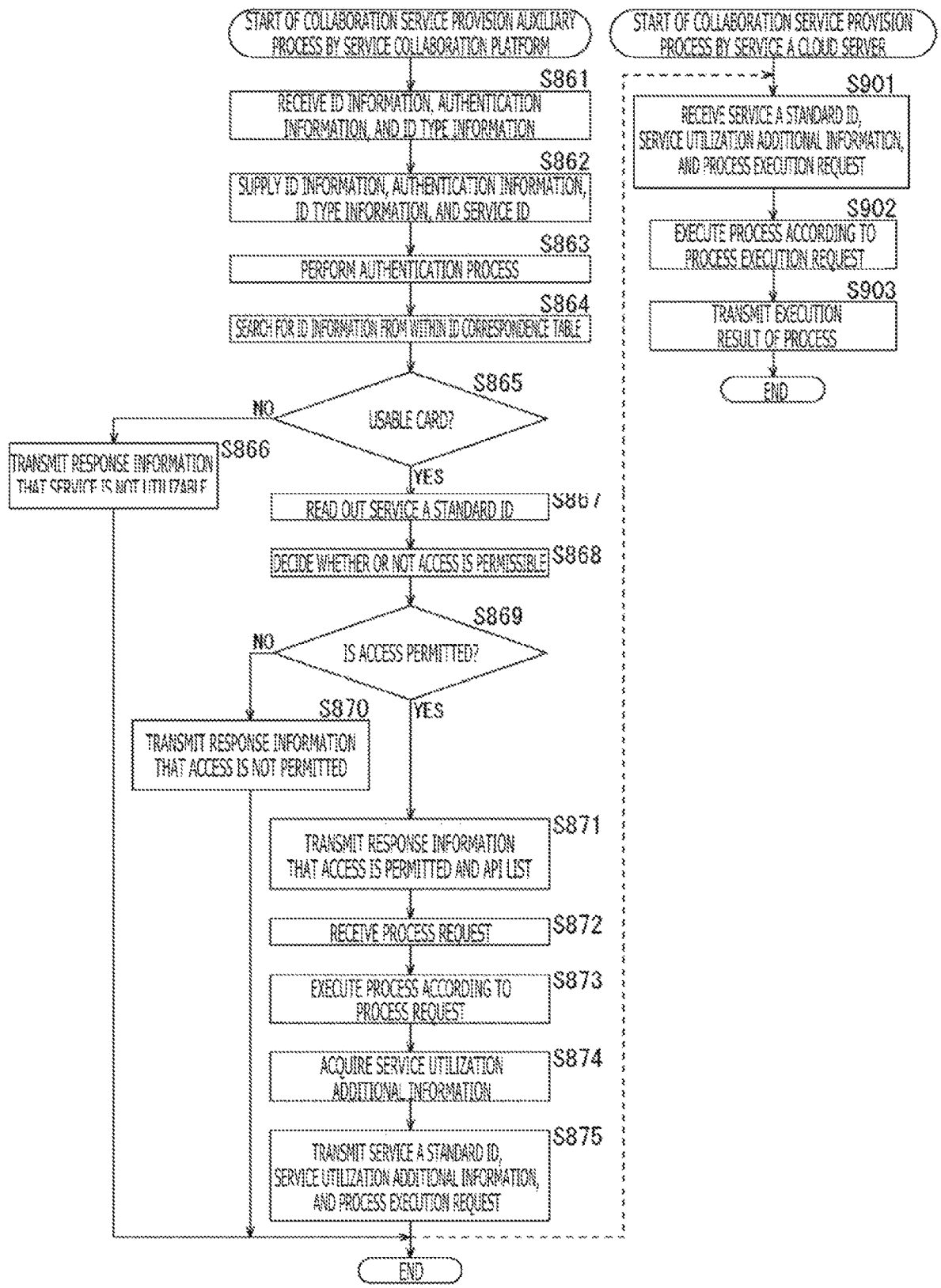
FIG. 37 is a flow chart illustrating a collaboration service provision auxiliary process and a collaboration service provision process.

In particular, a collaboration service provision auxiliary process by the service collaboration platform 402 and a collaboration service provision process by the service A cloud server 54 are described below with reference to a flow chart of FIG. 37.

At step S861, the communication unit 441 of the service collaboration platform 402 receives ID information, authentication information, and ID type information transmitted thereto from the service B cloud server 204 by the process at step S822 of FIG. 36 and supplies them to the service B management unit 412 of the control unit 442.

At step S862, the service B management unit 412 refers to the access information recorded in the recording unit 443 to supply the ID information, the authentication information, and the ID type information supplied from the communication unit 441 and a service ID to the service A management unit 411.

In particular, the service B management unit 412 supplies, together with a request for access to the service A, namely, to the service A management information, based on the access information, the ID information, the authentication information, the ID type information, and the service ID to the service A management unit 411.

More particularly, for example, the service B management unit 412 acquires the service ID and the public key recorded as access information to the service A in the recording unit 443 and decodes the service ID with the public key to obtain a service ID indicative of the service B. Here, the service ID recorded as the access information is, for example, in a form encrypted using a secrete key in advance by the service A management unit 411.

Consequently, the service A management unit 411 executes a process according to the request of the service B management unit 412. In particular, the service A management unit 411 suitably controls the associated components such that processes at succeeding steps S863 to S875 are executed.

At step S863, the authentication processing unit 451 performs an authentication process. It is to be noted that, since the process at step S863 is similar to the process at step S112 of FIG. 9, description of it is omitted.

At step S863, the ID type information and the authentication information are supplied from the service A management unit 411 to the authentication processing unit 451 and execution of an authentication process is requested, and the service common library 413 and the authentication information are used on the basis of the ID type information to perform an authentication process.

At step S864, the table management unit 461 of the service A management unit 411 searches for a combination of the ID information and the ID type information supplied from the communication unit 441 from within the ID correspondence table recorded as the service A management information in the recording unit 443.

At step S865, the service A management unit 411 decides from a result of the authentication process at step S863 and a result of the search at step S864 whether or not the IC card 401 is a card usable in the service A.

For example, in the case where the IC card 401 is authenticated as a legitimate one at step S863 and besides the combination of the ID information and the ID type information is recorded (registered) in the ID correspondence table at step S864, the IC card 401 is decides as a usable card.

In the case where it is decided at step S865 that the IC card 401 is not a usable card, the service A management unit 411 generates response information that a service cannot be utilized and supplies the response information to the communication unit 441, and the processing advances to step S866.

At step S866, the communication unit 441 transmits the response information supplied from the service A management unit 411 and representing that a service cannot be utilized to the service B cloud server 204 through the communication network 56, and the collaboration service provision auxiliary process comes to an end. In this case, in the service B cloud server 204, a process at step S824 of FIG. 36 is performed.

On the other hand, in the case where it is decided at step S865 that the IC card 401 is a usable card, the table management unit 461 reads out, at step S867, a service A standard ID associated with the ID information and the ID type information from the ID correspondence table on the basis of a result of the search at step S864.

At step S868, the service A management unit 411 specifies, on the basis of the other-service access permission information recorded as the service A management information in the recording unit 443, whether or not access of the user to the service A upon utilization of the service B is permissible. In other words, whether or not access of the service B cloud server 204 to the service A cloud server 54 is permissible is specified.

In particular, the service A management unit 411 specifies permissibility of access on the basis of the other-service access permission information recorded in the recording unit 443 in an associated relationship with the service A standard ID obtained at step S867 and the service ID received at step S862.

At step S869, the service A management unit 411 decides, on the basis of a result of the specification at step S868, whether or not access of the service B cloud server 204 to the service A cloud server 54 is permitted.

In the case where it is decided at step S869 that access is not permitted, the service A management unit 411 generates response information that access is not permitted to the communication unit 441, and the processing advances to step S870.

At step S870, the communication unit 441 transmits the response information supplied from the service A management unit 411 and representing that access is not permitted to the service B cloud server 204 through the communication network 56, and the collaboration service provision auxiliary process comes to an end. In this case, in the service B cloud server 204, the process at step S827 of FIG. 36 is performed.

In contrast, in the case where it is decided at step S869 that access is permitted, the service A management unit 411 generates response information that access is permitted and reads out the API list that is recorded as the service A management information in an associated relationship with the service ID indicative of the service B in the recording unit 443. Then, the service A management unit 411 supplies the response information and the API list to the communication unit 441, and the processing advances to step S871.

At step S871, the communication unit 441 transmits the response information, which represents that access is permitted, and the API list both supplied from the service A management unit 411 to the service B cloud server 204 through the communication network 56.

Consequently, in the service B cloud server 204, the process at step S829 of FIG. 36 is performed and the process at step S830 is performed, and a process request is transmitted to the service B cloud server 204.

At step S872, the communication unit 441 receives the process request transmitted from the service B cloud server 204 and supplies it to the service A management unit 411.

Consequently, at step S873, the service A management unit 411 executes a process according to the process request supplied from the communication unit 441 using the service A standard ID obtained at step S867. In particular, by executing the API in response to the process request, the service A management unit 411 controls execution of the processes at succeeding steps S874 and S875.

It is to be noted that the transmission of an API list from the service A management unit 411 and the supply of a process request to the service A management unit 411 described above may be performed by transfer of information through the service B management unit 412.

At step S874, the table management unit 461 of the service A management unit 411 acquires, on the basis of the service A standard ID obtained at step S867, service utilization additional information recorded in an associated relationship with the service A standard ID from the ID correspondence table of the recording unit 443.

Further, the service A management unit 411 generates a process execution request for requesting execution of a process according to the process request from the service B cloud server 204 based on the service A standard ID and the service utilization additional information, and supplies the process execution request, the service A standard ID, and the service utilization additional information to the communication unit 441.

At step S875, the communication unit 441 transmits the service A standard ID, the service utilization additional information, and the process execution request supplied from the service A management unit 411 to the service A cloud server 54 through the communication network 56 and instructs the service A cloud server 54 to access the service B cloud server 204, and the collaboration service provision auxiliary process comes to an end.

Further, after the service A standard ID, the service utilization additional information, and the process execution request are transmitted, a collaboration service provision process is performed in the service A cloud server 54.

In particular, processes at steps S901 to S903 are performed to execute the requested process, and a result of execution of the process is transmitted to the service B cloud server 204 and the collaboration service provision process comes to an end. Consequently, in the service B cloud server 204, the process at step S831 of FIG. 36 is performed.

Figure 28:
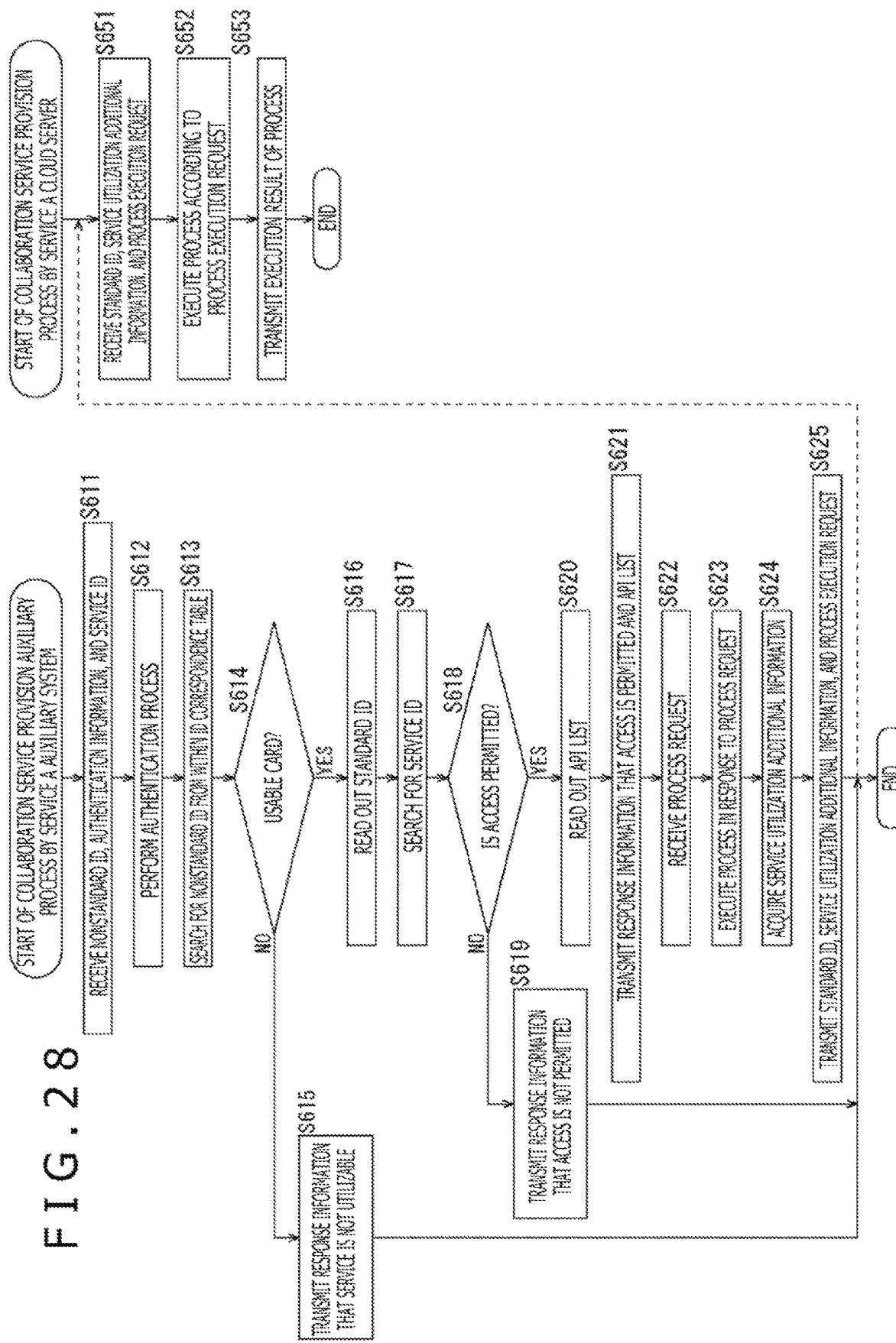
FIG. 28 is a flow chart illustrating a collaboration service provision auxiliary process and a collaboration service provision process.

It is to be noted that the processes at steps S901 to 903 are similar to the processes at steps S651 to S653 of FIG. 28 individually, and therefore, description of them is omitted. However, at steps S901 to S903, not the standard ID but the service A standard ID is used.

The service collaboration platform 402 performs an authentication process on the basis of authentication information and confirms access permission on the basis of other-service access permission information recorded in advance in such a manner as described above. Consequently, while the security is assured sufficiently, collaboration with another service becomes possible, and the convenience can be improved. Besides, by managing information relating to the service A or the service B by the service collaboration platform 402, the introduction cost of a service provider can be reduced.

Further, also the service provision system described in connection with the third embodiment can be applied to the system utilization example described hereinabove, for example, with reference to FIG. 29 or FIG. 30.

Furthermore, while, in the description of the embodiments described hereinabove, principally a service for browsing medication history information is described, the information that is managed by each cloud server such as the service A cloud server 54 or the like and is utilized for a service such as browsing is not limited to the medication history information but may be any information.

Further, while, in the description of the embodiments described hereinabove, an example is described in which authentication information is recoded in IC cards such as the service A IC card 51 or the other-service IC card 52 and the authentication information is utilized to perform an authentication process, the authentication process may not be performed especially. In particular, for example, in the example depicted in FIG. 2, a mutual authentication process using authentication information between the service A IC card 51 or the other-service IC card 52 and the service A client system 53, the service A cloud server 54, or the service A auxiliary system 55 may not be performed. In this case, authentication information may not be recorded in the IC cards.

Incidentally, while the series of processes described hereinabove can be executed by hardware, it can otherwise be executed by software. In the case where the series of processes is executed by software, a program that constructs the software is installed into a computer. Here, in the computer, a computer incorporated in hardware for exclusive use, a personal computer, for example, for universal use that can execute various functions by installing various programs and so forth are included.

FIG. 38 is a block diagram depicting an example of a hardware configuration of a computer that executes the series of processes described hereinabove by a program.

In the computer, a CPU (Central Processing Unit) 501, a ROM (Read Only Memory) 502, and a RAM (Random Access Memory) 503 are connected to each other by a bus 504.

To the bus 504, an input/output interface 505 is connected further. To the input/output interface 505, an inputting unit 506, an outputting unit 507, a recording unit 508, a communication unit 509, and a drive 510 are connected.

The inputting unit 506 is configured, for example, from a keyboard, a mouse, a microphone, an image pickup element and so forth. The outputting unit 507 is configured, for example, from a display, a speaker and so forth. The recording unit 508 is configured from a hard disk, a nonvolatile memory or the like. The communication unit 509 is configured from a network interface or the like. The drive 510 drives a removable recording medium 511 such as a magnetic disk, an optical disk, a magneto-optical disk, a semiconductor memory or the like.

In the computer configured in such a manner as described above, the CPU 501 loads a program stored, for example, in the recording unit 508 into the RAM 503 through the input/output interface 505 and the bus 504 and executes the program to perform the series of processes described hereinabove.

The program to be executed by the computer (CPU 501) can be recorded into and provided, for example, as a removable recording medium 511 as a package medium or the like. Further, the program can be provided through a wired or wireless transmission medium such as a local area network, the Internet, or a digital satellite broadcast.

In the computer, the program can be installed into the recording unit 508 through the input/output interface 505 by loading a removable recording medium 511 into the drive 510. Further, the program can be received through a wired or wireless transmission medium by the communication unit 509 and installed into the recording unit 508. Alternatively, the program can be installed into the ROM 502 or the recording unit 508 in advance.

It is to be noted that the program executed by the computer may be a program by which the processes are performed in a time series in accordance with the order described in the present specification or may be a program by which the processes are performed in parallel or at necessary timings such as when the program is called or the like.

Further, the embodiments of the present technology are not limited to the embodiments described hereinabove but can be altered in various manners without departing from the subject matter of the present technology.

For example, the present technology can assume a configuration of cloud computing by which one function is shared and jointly processed by a plurality of apparatus through a network.

Further, the steps described in connection with the flow charts described hereinabove can be executed by a single apparatus or can be shared and executed by a plurality of apparatus.

Furthermore, where a plurality of processes are included in one step, the plurality of processes included in the one step can be executed by a single apparatus or can be shared and executed by a plurality of apparatus.

Furthermore, the present technology can take also the following configuration.

(1)

An ID acquisition terminal apparatus connected to a medication history information management apparatus and an intermediate information management apparatus through a communication network, the ID acquisition terminal apparatus including:

a communication unit that transmits and receives information;

an acquisition unit that acquires ID information and service utilization additional information; and a control unit that controls the communication unit and the acquisition unit, in which, in the case where a standard ID as the ID information and first service utilization additional information are acquired by the acquisition unit, the control unit executes a process for transmitting the standard ID and the first service utilization additional information from the communication unit to the medication history information management apparatus, but, in the case where a nonstandard ID as the ID information and second service utilization additional information are acquired by the acquisition unit, the control unit executes a process for transmitting the nonstandard ID from the communication unit to the intermediate information management apparatus, a process for receiving the standard ID associated with the nonstandard ID and third service utilization additional information from the intermediate information management apparatus by the communication unit, and a process for transmitting the standard ID, the second service utilization additional information, and the third service utilization additional information from the communication unit.

(2)

The ID acquisition terminal apparatus according to (1), in which,
in the case where the nonstandard ID and the third service utilization additional information are acquired by the acquisition unit,
the control unit performs a process for transmitting the nonstandard ID and the third service utilization additional information to the intermediate information management apparatus.

(3)

The ID acquisition terminal apparatus according to (1) or (2), in which
the acquisition unit acquires the standard ID or the nonstandard ID and the service utilization additional information from an IC card.

(4)

An ID acquisition method by an ID acquisition terminal apparatus that is connected to a medication history information management apparatus and an intermediate information management apparatus through a communication network and includes
a communication unit that transmits and receives information,
an acquisition unit that acquires ID information and service utilization additional information, and
a control unit that controls the communication unit and the acquisition unit, the ID acquisition method including the steps of:
in the case where a standard ID as the ID information and first service utilization additional information are acquired by the acquisition unit,
by the control unit, executing a process for transmitting the standard ID and the first service utilization additional information from the communication unit to the medication history information management apparatus, but;
in the case where a nonstandard ID as the ID information and second service utilization additional information are acquired by the acquisition unit,
by the control unit, executing
a process for transmitting the nonstandard ID from the communication unit to the intermediate information management apparatus,
a process for receiving the standard ID associated with the nonstandard ID and third service utilization additional information from the intermediate information management apparatus by the communication unit, and
a process for transmitting the standard ID, the second service utilization additional information, and the third service utilization additional information from the communication unit.

(5)

A program for causing a computer to function as an ID acquisition terminal apparatus that is connected to a medication history information management apparatus and an intermediate information management apparatus through a communication network and includes
a communication unit that transmits and receives information,
an acquisition unit that acquires ID information and service utilization additional information, and
a control unit that controls the communication unit and the acquisition unit, the program including:
in the case where a standard ID as the ID information and first service utilization additional information are acquired by the acquisition unit,
by the control unit, executing a process for transmitting the standard ID and the first service utilization additional information from the communication unit to the medication history information management apparatus, but;
in the case where a nonstandard ID as the ID information and second service utilization additional information are acquired by the acquisition unit,
by the control unit, executing
a process for transmitting the nonstandard ID from the communication unit to the intermediate information management apparatus,
a process for receiving the standard ID associated with the nonstandard ID and third service utilization additional information from the intermediate information management apparatus by the communication unit, and
a process for transmitting the standard ID, the second service utilization additional information, and the third service utilization additional information from the communication unit.

(6)

An information processing apparatus including:
an acquisition unit that acquires nonstandard ID information different from ID information, which is used upon provision of a given service, and authentication information;
an authentication processing unit that performs an authentication process of the nonstandard ID information with the authentication information;
a recording unit that records the nonstandard ID information, the ID information, and service utilization additional information that is used upon provision of the service in an associated relationship with each other; and
a management unit that acquires the ID information and the service utilization additional information associated with the nonstandard ID information from the recording unit.

(7)

The information processing apparatus according to (6), in which
the acquisition unit acquires information for obtaining the service utilization additional information that is newer, and
the management unit updates the service utilization additional information recorded in the recording unit based on the information for obtaining the service utilization additional information that is newer.

(8)

The information processing apparatus according to (6), in which
the acquisition unit acquires the ID information and the service utilization additional information, and
the management unit specifies a newer one from between the service utilization additional information acquired by the acquisition unit and the service utilization additional information recorded in the recording unit and either updates the service utilization additional information recorded in the recording unit or controls update of the ID information by the acquisition unit and the service utilization additional information of an acquisition source of the service utilization additional information.

(9)

The information processing apparatus according to (6), in which
the recording unit records the nonstandard ID information, the ID information, and service utilization additional information difference information for obtaining part of the service utilization additional information in an associated relationship with each other,
the acquisition unit acquires the nonstandard ID information, the authentication information, and service utilization additional information corresponding information for obtaining part of the service utilization additional information upon provision of the service, and the information processing apparatus further includes a control unit that generates the service utilization additional information based on the service utilization additional information difference information and the service utilization additional information corresponding information.

(10)

The information processing apparatus according to (6), in which, in the case where part of the nonstandard ID information recorded in an acquisition source of the nonstandard ID information by the acquisition unit changes by reissuance, the management unit compares the nonstandard ID information acquired by the acquisition unit and the nonstandard ID information recorded in the recording unit with each other and updates the nonstandard ID information recorded in the recording unit in response to a result of the comparison.

(11)

An information processing method including the steps of:

acquiring nonstandard ID information different from ID information, which is used upon provision of a given service, and authentication information;

performing an authentication process of the nonstandard ID information with the authentication information; and acquiring, from a recording unit that records the nonstandard ID information, the ID information, and service utilization additional information that is used upon provision of the service in an associated relationship with each other, the ID information and the service utilization additional information associated with the nonstandard ID information.

(12)

A program for causing a computer to execute a process, including the steps of:

acquiring nonstandard ID information different from ID information, which is used upon provision of a given service, and authentication information;

performing an authentication process of the nonstandard ID information with the authentication information; and acquiring, from a recording unit that records the nonstandard ID information, the ID information, and service utilization additional information that is used upon provision of the service in an associated relationship with each other, the ID information and the service utilization additional information associated with the nonstandard ID information.

(13)

An information processing apparatus including:

an acquisition unit that acquires nonstandard ID information different from ID information that is used upon provision of a given service from an other-service provision apparatus that provides a different service different from the given service;

a management unit that reads out the ID information recorded in an associated relationship with the nonstandard ID information; and a process execution unit that executes, in the case where execution of a process for providing the given service permitted to the different service is requested from the other-service provision apparatus, a process according to the request using the ID information.

(14)

The information processing apparatus according to (13), in which the acquisition unit acquires authentication information together with the nonstandard ID information from the other-service provision apparatus, and the information processing apparatus further includes an authentication processing unit that performs an authentication process of the nonstandard ID information with the authentication information.

(15)

The information processing apparatus according to (13) or (14), further including:

a recording unit that records other-service access permission information set by a user and indicative of whether or not access of the different service to the given service is to be permitted; and a control unit that permits the access of the other-service provision apparatus based on the other-service access permission information.

(16)

An information processing method including the steps of:

acquiring nonstandard ID information different from ID information that is used upon provision of a given service from an other-service provision apparatus that provides a different service different from the given service;

reading out the ID information recorded in an associated relationship with the nonstandard ID information; and executing, in the case where execution of a process for providing the given service permitted to the different service is requested from the other-service provision apparatus, a process according to the request using the ID information.

(17)

An information processing apparatus including:

an acquisition unit that acquires nonstandard ID information different from ID information to be used upon provision of a given service from an other-service provision apparatus that provides a different service different from the given service;

an other-service management unit that manages access information for allowing the different service to access the given service; and a service management unit that reads out, in the case where the nonstandard ID information acquired by the acquisition unit is supplied to the service management unit together with a request for access to the given service based on the access information from the service management unit, the ID information recorded in an associated relationship with the nonstandard ID information and executes, using the ID information, a process according to a request for execution of a process for providing the given service permitted to the different service.

(18)

The information processing apparatus according to (17), in which the acquisition unit acquires authentication information together with the nonstandard ID information from the other-service provision apparatus, and the information processing apparatus further includes an authentication processing unit that performs an authentication process of the nonstandard ID information based on library information common to the individual services and the authentication information.

(19)

The information processing apparatus according to (17) or (18), in which the service management unit manages other-service access permission information set by a user and indicative of whether or not access of the different service to the given service is permitted and permits access to the other-service provision apparatus based on the other-service access permission information.

(20)

An information processing method for an information processing apparatus that includes
an acquisition unit that acquires nonstandard ID information different from ID information to be used upon provision of a given service from an other-service provision apparatus that provides a different service different from the given service,
an other-service management unit that manages access information for allowing the different service to access the given service, and
a service management unit that reads out, in the case where the nonstandard ID information acquired by the acquisition unit is supplied to the service management unit together with a request for access to the given service based on the access information from the service management unit, the ID information recorded in an associated relationship with the nonstandard ID information and executes, using the ID information, a process according to a request for execution of a process for providing the given service permitted to the different service, the information processing method including the steps of:
by the acquisition unit, acquiring the nonstandard ID information from the other-service provision apparatus;
by the other-service management unit, requesting access to the given service based on the access information to the service management unit and supplying the nonstandard ID information acquired by the acquisition unit to the service management unit; and
by the service management unit, reading out the ID information recorded in an associated relationship with the nonstandard ID information and executing, using the ID information, a process according to a request from the other-service provision apparatus for executing a process for providing the given service permitted to the different service.

REFERENCE SIGNS LIST

51 Service A IC card, 52 Other-service IC card, 53 Service A client system, 54 Service A cloud server, 55 Service A auxiliary system, 62 Client apparatus, 161 Communication unit, 162 Control unit, 163 Recording unit, 171 Authentication processing unit, 172 Table management unit, 173 Generation unit, 201 Service A nonstandard IC card, 203 Service B client system, 204 Service B cloud server, 401 IC card, 402 Service collaboration platform

The invention claimed is:

1. An ID acquisition terminal apparatus connected to a medication history information management apparatus and an intermediate information management apparatus through a communication network, the ID acquisition terminal apparatus comprising:
circuitry configured to:
acquire ID information and service utilization additional information;
in a case where a standard ID as the ID information and first service utilization additional information are acquired control transmission of the standard ID and the first service utilization additional information to the medication history information management apparatus;
in a case where a nonstandard ID as the ID information and second service utilization additional information are acquired, control transmission of the nonstandard ID to the intermediate information management apparatus;
control reception of the standard ID associated with the nonstandard ID and third service utilization additional information from the intermediate information management apparatus; and
control transmission of the standard ID, the second service utilization additional information, and the third service utilization additional information.

2. The ID acquisition terminal apparatus according to claim 1, wherein
in a case where the nonstandard ID and the third service utilization additional information are acquired, the circuitry is further configured to control transmission of the nonstandard ID and the third service utilization additional information to the intermediate information management apparatus.

3. The ID acquisition terminal apparatus according to claim 1, wherein the circuitry is further configured to acquire one of the standard ID or the nonstandard ID and the service utilization additional information from an IC card.

4. An ID acquisition method, comprising:
in an ID acquisition terminal apparatus that is connected to a medication history information management apparatus and an intermediate information management apparatus through a communication network:
acquiring ID information and service utilization additional information;
in a case where a standard ID as the ID information and first service utilization additional information are acquired, transmitting the standard ID and the first service utilization additional information to the medication history information management apparatus;
in a case where a nonstandard ID as the ID information and second service utilization additional information are acquired, transmitting the nonstandard ID to the intermediate information management apparatus;
receiving the standard ID associated with the nonstandard ID and third service utilization additional information from the intermediate information management apparatus; and
transmitting the standard ID, the second service utilization additional information, and the third service utilization additional information.

5. A non-transitory computer-readable medium having stored thereon, computer-executable instructions which, when executed by a computer, cause the computer to execute operations, the operations comprising:
acquiring ID information and service utilization additional information;
in a case where a standard ID as the ID information and first service utilization additional information are acquired, transmitting the standard ID and the first service utilization additional information to a medication history information management apparatus;
in a case where a nonstandard ID as the ID information and second service utilization additional information are acquired, transmitting the nonstandard ID to an intermediate information management apparatus;
receiving the standard ID associated with the nonstandard ID and third service utilization additional information from the intermediate information management apparatus; and transmitting the standard ID, the second service utilization additional information, and the third service utilization additional information.

6. An information processing apparatus, comprising:
circuitry configured to:
  acquire nonstandard ID information that is different from ID information, and authentication information, wherein the ID information is used for provision of a specific service;
  execute an authentication process of the nonstandard ID information with the authentication information;
  record the nonstandard ID information in association with the ID information and service utilization additional information that is used for the provision of the specific service;
  acquire the recorded ID information and the recorded service utilization additional information associated with the recorded nonstandard ID information;
  in a case where a part of the nonstandard ID information recorded in an acquisition source of the nonstandard ID information changes by reissuance, compare the acquired nonstandard ID information and the recorded nonstandard ID information; and
  update the recorded nonstandard ID information based on a result of the comparison.

7. The information processing apparatus according to claim 6, wherein the circuitry is further configured to:
  acquire information to obtain the service utilization additional information that is newer; and
  update the service utilization additional information based on the information to obtain the service utilization additional information that is newer.

8. The information processing apparatus according to claim 6, wherein the circuitry is further configured to
  acquire the ID information and the service utilization additional information;
  determine a newer one from between the acquired service utilization additional information and the recorded service utilization additional information; and
  update one of the recorded service utilization additional information or the ID information and acquired the service utilization additional information of an acquisition source of the acquired service utilization additional information.

9. The information processing apparatus according to claim 6, wherein the circuitry is further configured to:
  record the nonstandard ID information in association with the ID information and service utilization additional information difference information to obtain a part of the service utilization additional information;
  acquire the nonstandard ID information, the authentication information, and service utilization additional information corresponding information to obtain the part of the service utilization additional information; and
  generate the service utilization additional information based on the service utilization additional information difference information and the service utilization additional information corresponding information.

10. An information processing method, comprising:
  acquiring nonstandard ID information that is different from ID information, and authentication information, wherein the ID information is used for provision of a specific service;
  executing an authentication process of the nonstandard ID information with the authentication information;
  recording the nonstandard ID information in association with the ID information and service utilization additional information that is used for the provision of the specific service;
  acquiring the recorded ID information and the recorded service utilization additional information associated with the recorded nonstandard ID information;
  in a case where a part of the nonstandard ID information recorded in an acquisition source of the nonstandard ID information changes by reissuance, comparing the acquired nonstandard ID information and the recorded nonstandard ID information; and
  updating the recorded nonstandard ID information based on a result of the comparison.

11. A non-transitory computer-readable medium having stored thereon, computer-executable instructions which, when executed by a computer, cause the computer to execute operations, the operations comprising:
  acquiring nonstandard ID information that is different from ID information, and authentication information, wherein the ID information is used for provision of a specific service;
  executing an authentication process of the nonstandard ID information with the authentication information;
  recording the nonstandard ID information in association with the ID information and service utilization additional information that is used for the provision of the specific service;
  acquiring the recorded ID information and the recorded service utilization additional information associated with the recorded nonstandard ID information;
  in a case where a part of the nonstandard ID information recorded in an acquisition source of the nonstandard ID information changes by reissuance, comparing the acquired nonstandard ID information and the recorded nonstandard ID information; and
  updating the recorded nonstandard ID information based on a result of the comparison.

12. An information processing apparatus, comprising:
circuitry configured to:
  acquire nonstandard ID information that is different from ID information, wherein
    the ID information is used for provision of a specific service from an other-service provision apparatus that provides a different service different from the specific service, and
    the nonstandard ID information is recorded in an associated relationship with the ID information;
  read the ID information recorded in the associated relationship with the nonstandard ID information;
  in a case where execution of a process to provide the specific service permitted to the different service is requested from the other-service provision apparatus, execute the process based on a request that uses the ID information;
  in a case where a part of the nonstandard ID information recorded in an acquisition source of the nonstandard ID information changes by reissuance, compare the acquired nonstandard ID information and the recorded nonstandard ID information; and
  update the recorded nonstandard ID information based on a result of the comparison.

13. The information processing apparatus according to claim 12, wherein the circuitry is further configured to:
  acquire authentication information and the nonstandard ID information from the other-service provision apparatus; and execute an authentication process of the nonstandard ID information with the authentication information.

14. The information processing apparatus according to claim 12, wherein the circuitry is further configured to:
   record other-service access permission information set based on a user input, the other-service access permission information indicative of whether or not access of the different service to the specific service is to be permitted; and
   permit access of the other-service provision apparatus based on the other-service access permission information.

15. An information processing method, comprising:
   acquiring nonstandard ID information that is different from ID information, wherein
      the ID information is used for provision of a specific service from an other-service provision apparatus that provides a different service different from the specific service, and
      the nonstandard ID information is recorded in an associated relationship with the ID information;
   reading the ID information recorded in the associated relationship with the nonstandard ID information;
   executing, in a case where execution of a process for providing the specific service permitted to the different service is requested from the other-service provision apparatus, the process based on a request using the ID information;
   in a case where a part of the nonstandard ID information in an acquisition source of the nonstandard ID information changes by reissuance, comparing the acquired nonstandard ID information and the recorded nonstandard ID information; and
   updating the recorded nonstandard ID information based on a result of the comparison.

16. An information processing apparatus, comprising:
   circuitry configured to:
      acquire nonstandard ID information that is different from ID information, wherein
         the ID information is used for provision of a specific service from an other-service provision apparatus that provides a different service different from the specific service, and
         the nonstandard ID information is recorded in an associated relationship with the ID information;
      manage access information to allow the different service to access the specific service;
      read, in a case where the acquired nonstandard ID information is supplied together with a request for access to the specific service based on the access information, the ID information recorded in the associated relationship with the nonstandard ID information;
      execute, using the ID information, a process based on a request for execution of the process to provide the specific service permitted to the different service;
      in a case where a part of the nonstandard ID information recorded in an acquisition source of the nonstandard ID information changes by reissuance, compare the acquired nonstandard ID information and the recorded nonstandard ID information; and
      update the recorded nonstandard ID information based on a result of the comparison.

17. The information processing apparatus according to claim 16, wherein the circuitry is further configured to:
   acquire authentication information and the nonstandard ID information from the other-service provision apparatus; and
   execute an authentication process of the nonstandard ID information based on library information common to individual services and the authentication information.

18. The information processing apparatus according to claim 16, wherein the circuitry is further configured to:
   manage other-service access permission information set based on a user input, the other-service access permission information indicative of whether access of the different service to the specific service is permitted; and
   permit access to the other-service provision apparatus based on the other-service access permission information.

19. An information processing method, comprising:
   acquiring nonstandard ID information that is different from ID information, wherein
      the ID information is used for provision of a specific service from an other-service provision apparatus that provides a different service different from the specific service, and
      the nonstandard ID information is recorded in an associated relationship with the ID information;
   managing access information for allowing the different service to access the specific service;
   reading, in a case where the nonstandard ID information is supplied together with a request for access to the specific service based on the access information, the ID information recorded in the associated relationship with the nonstandard ID information;
   executing, using the ID information, a process based on a request for execution of the process for providing the specific service permitted to the different service;
   in a case where a part of the nonstandard ID information recorded in an acquisition source of the nonstandard ID information changes by reissuance, comparing the acquired nonstandard ID information and the recorded nonstandard ID information; and
   updating the recorded nonstandard ID information based on a result of the comparison.

* * * * *